(12) United States Patent
Kawano et al.

(10) Patent No.: US 6,248,740 B1
(45) Date of Patent: Jun. 19, 2001

(54) CONDENSED PYRIDAZINE DERIVATIVES, THEIR PRODUCTION AND USE

(75) Inventors: Yasuhiko Kawano, Suita; Hideaki Nagaya, Toyonaka; Michiyo Gyoten, Daito, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/284,362

(22) PCT Filed: Apr. 23, 1998

(86) PCT No.: PCT/JP98/01869

§ 371 Date: Apr. 14, 1999

§ 102(e) Date: Apr. 14, 1999

(87) PCT Pub. No.: WO98/49167

PCT Pub. Date: Nov. 5, 1998

(30) Foreign Application Priority Data

Apr. 25, 1997 (JP) .................................... 9-109914
Feb. 27, 1998 (JP) ................................. 10-046688

(51) Int. Cl.⁷ ..................... C07D 403/04; C07D 403/06; C07D 403/12; A61K 31/5025; A61P 11/06
(52) U.S. Cl. ........................................ 514/248; 544/236
(58) Field of Search ............................. 544/236; 514/248

(56) References Cited

U.S. PATENT DOCUMENTS 3,878,217 * 4/1975 Carr et al. ................. 260/293.64

FOREIGN PATENT DOCUMENTS

| 381132 | 8/1990 | (EP) . |
| 440119 | 8/1991 | (EP) . |
| 444549 | 9/1991 | (EP) . |
| 0548923A2 | 6/1993 | (EP) . |
| 548923 | * 6/1993 | (EP) . |
| 562439 | * 9/1993 | (EP) . |
| 0562439A1 | 9/1993 | (EP) . |
| 562440 | 9/1993 | (EP) . |
| 620224 | 10/1994 | (EP) . |
| 632040 | * 1/1995 | (EP) . |
| 0632040A1 | 1/1995 | (EP) . |
| 648491 | 4/1995 | (EP) . |
| WO96/08496 | 3/1996 | (WO) . |
| WO96/23798 | 8/1996 | (WO) . |

* cited by examiner

Primary Examiner—Mark L. Berch
Assistant Examiner—Thomas C McKenzie
(74) Attorney, Agent, or Firm—Philippe Y. Riesen; Mark Chao

(57) ABSTRACT

The present invention provides a compound represented by the formula:

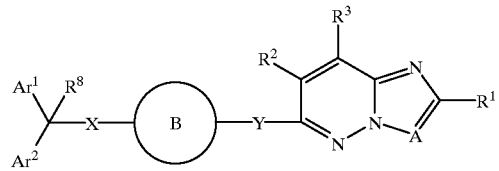

wherein $Ar^1$ and $Ar^2$ are independently an aromatic group which may be substituted, and $Ar^1$ and $Ar^2$ may form a condensed cyclic group with an adjacent carbon atom; ring B is a nitrogen-containing heterocycle which may be substituted; X and Y are the same or different and are independently a bond, an oxygen atom, S(O)p (p is an integer of 0 ot 2), $NR^4$ wherein $R^4$ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or $CR^7$ wherein $R^7$ is a hydrogen atom, a halogen atom, a hydrocarbon which may be substituted, an acyl group or a hydroxy group which may be substituted; $R^1$, $R^2$ and $R^3$ are the same or different and are independently a hydrogen atom, a halogen atom, a hydrocarbon group which may be substituted, an acyl group or a hydroxy group which may be substituted; $R^8$ is a hydrogen atom, a hydroxy group which may be substituted by a lower alkyl or a carboxyl group, or a salt thereof, which exhibits excellent anti-histaminic or eosinophil chemotaxis-inhibiting activities and is useful in treatment or prevention of asthma, allergic conjunctivitis, allergic rhinitis, chronic urticaria or atopic dermatitis.

33 Claims, No Drawings

CONDENSED PYRIDAZINE DERIVATIVES, THEIR PRODUCTION AND USE

This application is the National Stage of International Patent Application Ser. No. PCT/JP98/01869, filed Apr. 23, 1998.

TECHNICAL FIELD

The present invention relates to novel condensed pyridazine derivatives exhibiting an excellent anti-allergic, anti-histaminic, anti-inflammatory or eosinophil chemotaxis-inhibiting activity, or other activities, and useful as an agent for treating or preventing atopic dermatitis, allergic rhinitis, bronchial asthma, allergic conjunctivitis, chronic urticaria, etc., a method for producing them, and a pharmaceutical composition containing them.

BACKGROUND ART

Many condensed pyridazine derivatives are currently synthesized as drugs for a variety of diseases. For example, U.S. Pat. No. 3,915,968 discloses a compound represented by the formula:

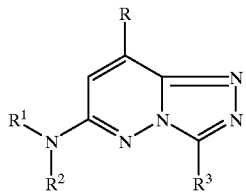

wherein R and $R^3$ independently represent a hydrogen atom or a lower alkyl group (at least one of R and $R^3$ is a lower alkyl group); $R^1$ and $R^2$ represent a heterocyclic group selected from the group consisting of pyrrolidine, piperidine, piperazine and morpholine taken together with the adjacent nitrogen atom; or a salt thereof. U.S. Pat. No. 4,136,182 discloses that a compound represented by the formula:

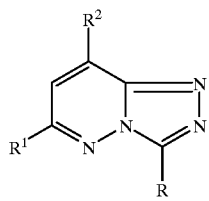

wherein R represents a hydrogen atom, a phenyl group or a lower alkylcarbonylamino group; $R^1$ represents morpholino or piperidino; $R^2$ represents a hydrogen atom or a lower alkyl group (at least one of R and $R^2$ is a group other than a hydrogen atom; when R is a phenyl group, $R^1$ is morpholino and $R^2$ is a lower alkyl group); or a salt thereof, is useful as a bronchodilator for mitigating bronchial spasms. Also, Japanese Patent Unexamined Publication No. 279447/1995 discloses that a compound represented by the formula:

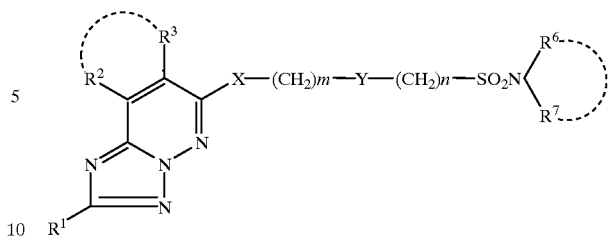

wherein $R^1$ represents a hydrogen atom, a lower alkyl group that may be substituted, or a halogen atom; $R^2$ and $R^3$ independently represent a hydrogen atom or a lower alkyl group which may be substituted, or may form a 5- to 7-membered ring with the adjacent —C=C—; X represents an oxygen atom or $S(O)_p$ (p represents an integer from 0 to 2);

Y represents a group represented by the formula:

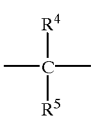

($R^4$ and $R^5$ independently represent a hydrogen atom or a lower alkyl group which may be substituted) or a divalent group derived from a 3- to 7-membered homocycle or heterocycle which may be substituted; $R^6$ and $R^7$ independently represent a hydrogen atom, a lower alkyl group which may be substituted, a cycloalkyl group which may be substituted, or an aryl group that may be substituted, or may form a nitrogen-containing heterocyclic group which may be substituted, with the adjacent nitrogen atom; m represents an integer from 0 to 4, and n represents an integer from 0 to 4; or a salt thereof; and, as an example synthetic product, a compound of the formula:

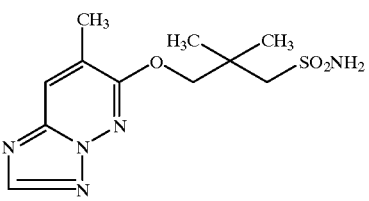

exhibits anti-asthmatic, anti-PAF, anti-inflammatory and anti-allergic activities. Furthermore, Japanese Patent Unexamined Publication No. 279446/1995 describes a compound represented by the formula:

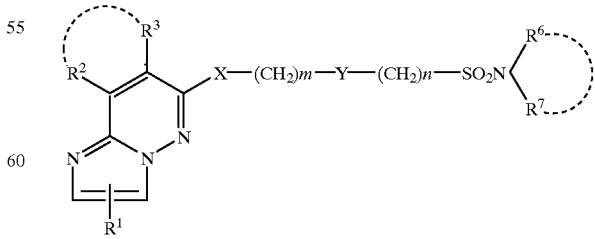

wherein $R^1$ represents a hydrogen atom, a lower alkyl group which may be substituted, or a halogen atom; $R^2$ and $R^3$ independently represent a hydrogen atom or a lower alkyl group which may be substituted (provided that either of $R^2$ and $R^3$ is a hydrogen atom, the other represents a lower alkyl group which may be substituted), or may form a 5- to 7-membered ring taken together with the adjacent —C═C—; X represents an oxygen atom or $S(O)_p$ (p represents an integer from 0 to 2); Y represents a group represented by the formula:

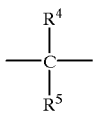

($R^4$ and $R^5$ independently represent a hydrogen atom or a lower alkyl group which may be substituted) or a divalent group derived from a 3- to 7-membered homocycle or heterocycle which may be substituted; $R^6$ and $R^7$ independently represent a hydrogen atom, a lower alkyl group which may be substituted, a cycloalkyl group which may be substituted, or an aryl group which may be substituted, or may form a nitrogen-containing heterocyclic group which may be substituted, taken together with the adjacent nitrogen atom; m represents an integer from 0 to 4, and n represents an integer from 0 to 4; or a salt thereof; and discloses that these compounds possess anti-allergic, anti-inflammatory and anti-PAF (platelet activating factor) activities to suppress bronchial spasms and bronchial contraction, therefore could be utilized as effective anti-asthmatic agents.

On the other hand, as compounds exhibiting anti-allergic or anti-histaminic activities, there may be mentioned, for example, terfenadine (The Merck Index, 12th edition, 9307) and ebastine (The Merck Index, 12th edition, 3534), which are already in clinical use.

There is demand for the development of novel compounds more satisfactory than conventional anti-allergic agents, anti-histaminic, anti-inflammatory agents etc., in terms of action efficacy, sustained action, safety etc.

Through various extensive investigations, the present inventors produced for the first time novel condensed pyridazine compounds represented by the formula:

(I)

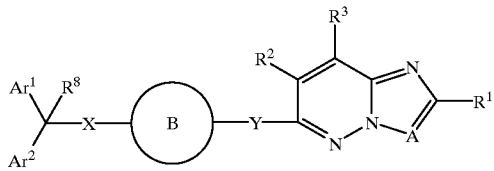

wherein $Ar^1$ and $Ar^2$ are independently an aromatic group which may be substituted, and $Ar^1$ and $Ar^2$ may form a condensed cyclic group with an adjacent carbon atom; ring B is a nitrogen-containing heterocycle may be substituted; X and Y are the same or different and are independently a bond, an oxygen atom, $S(O)_p$ (p is an integer from 0 to 2), $NR^4$ wherein $R^4$ is a hydrogen atom or a lower alkyl group, or a divalent linear lower hydrocarbon group which may contain 1 to 3 hetero atoms and the bivalent linear lower hydrocarbon group may be substituted; A is a nitrogen atom or $CR^7$ ($R^7$ is a hydrogen atom, a halogen atom, a hydrocarbon group which may be substituted, an acyl group or a hydroxy group which may be substituted; $R^1$, $R^2$ and $R^3$ are the same or different and are independently a hydrogen atom, a halogen atom, a hydrocarbon group which may be substituted, an acyl group or a hydroxy group which may be substituted; $R^8$ is a hydrogen atom, a hydroxy group which may be substituted by lower alkyl, or a carboxyl group; or a salt thereof, and found that these compounds, owing to their unique chemical structure characterized by the presence of substitutional piperidine or piperazine via a spacer from the 6-position of the [1,2,4]triazolo[1,5-b]pyridazine or imidazo[1,2-b]pyridazine skeleton, exhibits unexpectedly excellent anti-allergic, anti-histaminic, anti-inflammatory, and eosinophil chemotaxis-inhibiting activities, with excellent sustained activity and safety, and that it serves as an agent for treating or preventing atopic dermatitis, allergic rhinitis, bronchial asthma, allergic conjunctivitis, chronic urticaria, etc., on the basis of these pharmacological activities. The inventors conducted further investigations based on these findings, and developed the present invention.

DISCLOSURE OF INVENTION

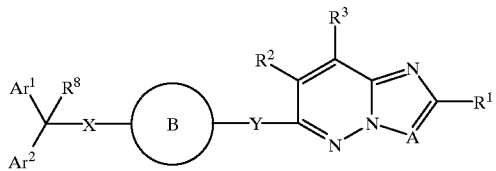

The present invention provides:
(1) A compound represented by the formula:
wherein $Ar^1$ and $Ar^2$ are independently an aromatic group which may be substituted, and $Ar^1$ and $Ar^2$ may form a condensed cyclic group with an adjacent carbon atom; ring B is a nitrogen-containing heterocycle which may be substituted; X and Y are the same or different and are independently a bond, an oxygen atom, S(O)p (p is an integer of 0 ot 2), $NR^4$ wherein $R^4$ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or $CR^7$ wherein $R^7$ is a hydrogen atom, a halogen atom, a hydrocarbon which may be substituted, an acyl group or a hydroxy group which may be substituted; $R^1$, $R^2$ and $R^3$ are the same or different and are independently a hydrogen atom, a halogen atom, a hydrocarbon group which may be substituted, an acyl group or a hydroxy group which may be substituted; $R^8$ is a hydrogen atom, a hydroxy group which may be substituted by lower alkyl or a carboxyl group, or a salt thereof,
(2) The compound as defined in (1) wherein $Ar^1$ and $Ar^2$ are independently (i) a $C_{6-14}$ aromatic hydrocarbon group, (ii) a 5 to 8 membered aromatic heterocyclic group containing 1 to 4 hetero atoms selected from a nitrogen atom, a sulfur atom and an oxygen atom other than carbon atoms or (iii) a group removed a hydrogen atom from a condensed ring formed by the 5 to 8 membered aromatic heterocyclic group and the $C_{6-14}$ aromatic hydrocarbon group, and the $C_{6-14}$ aromatic hydrocarbon group, the 5 to 8 membered aromatic heterocyclic group and the group formed by the 5 to 8 membered aromatic heterocyclic group and the $C_{6-14}$ aromatic hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo; and $Ar^1$, $Ar^2$ and the adjacent carbon atom may form a condensed cyclic group represented by the formula:

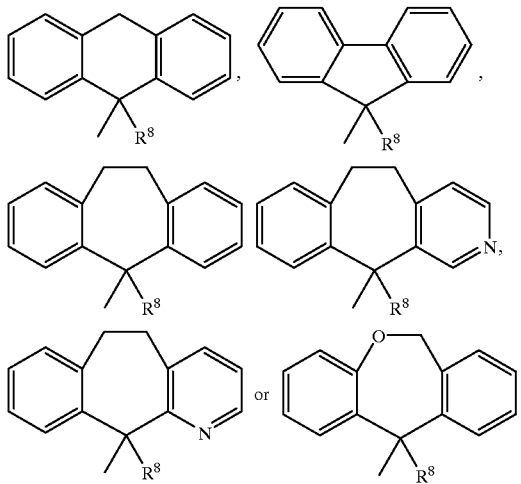

wherein $R^8$ is a hydrogen atom, a hydroxy group which may be substituted by $C_{1-6}$ alkyl or a carboxyl group, and the condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii ) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo;

the ring B is a 3 to 13 membered nitrogen-containing heteroycle containing at least one nitrogen atom which may contain 1 to 3 hetero atoms selected by a nitrogen atom, an oxygen atom and a sulfur atom, and the 3 to 13 membered nitrogen-containing heterocycle may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo;

X and Y are the same or different and are independently (a) a bond, (b) an oxygen atom, (c) S(O)p wherein p is an integer of 0 to 2, (d) $NR^4$ wherein $R^4$ is a hydrogen atom or a linear or branched $C_{1-6}$ alkyl group or (e) a bivalent linear $C_{1-6}$ hydrocarbon group which may contain 1 to 3 hetero atoms selected by an oxygen atom and a sulfur atom, and the bivalent linear $C_{1-6}$ hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo;

A is a nitrogen atom or $CR^7$ wherein $R^7$ is
(a) a hydrogen atom,
(b) a halogen atom,
(c) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo,
(d) an acyl group represented by the formula: —(C=O)—$R^9$, —$SO_2$—$R^9$, —SO—$R^9$, —(C=O)$NR^{10}R^9$, —(C=O)O—$R^9$, —(C=S)O—$R^9$ or —(C=S)$NR^{10}R^9$ wherein $R^9$ is (a') a hydrogen atom, (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo or (c') a group represented by the formula: $-OR^{11}$ wherein $R^{11}$ is (a'') a hydrogen atom or (b'') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo, $R^{10}$ is a hydrogen atom or a $C_{1-6}$ alkyl group, or (e) a group represented by the formula: $-OR^{12}$ wherein $R^{12}$ is (a') a hydrogen atom or (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo;

$R^1$, $R^2$ and $R^3$ are the same or different and are independently
(a) a hydrogen atom,
(b) a halogen atom,
(c) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (Xxvii) $C_{7-16}$ aralkyloxy and (xxviii) oxo,
(d) an acyl group represented by the formula: $-(C=O)-R^{13}$, $-SO_2-R^{13}$, $-SO-R^{13}$, $-(C=O)NR^{14}R^{13}$, $-(C=O)O-R^{13}$, $-(C=S)O-R^{13}$ or $-(C=S)NR^{14}R^{13}$ wherein $R^{13}$ is (a') a hydrogen atom, (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo or (c') a group represented by the formula: $-OR^{15}$ wherein $R^{15}$ is (a'') a hydrogen atom or (b'') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo, $R^{14}$ is a hydrogen atom or a $C_{1-6}$ alkyl group; or
(e) a group represented by the formula: $-OR^{16}$ wherein $R^{16}$ is (a') a hydrogen atom or (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (Viii) $C_{3-6}$ cycloalkyl, (ix) $C_{1-6}$ alkoxy which may be substituted by 1 to 3 halogen atoms, mono- or di-$C_{1-6}$ alkylamino or $C_{16}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyloxy and (xxviii) oxo;
$R^8$ is a hydrogen atom, a hydroxy group which may be substituted by $C_{1-6}$ alkyl or a carboxyl group, (3) The compound as defined in (1) wherein $Ar^1$ and $Ar^2$ are independently an aromatic hydrocarbon group which may be substituted, (4) The compound as defined in (1) wherein $Ar^1$ and $Ar^2$ are independently a phenyl group which may be substituted, (5) The compound as defined in (1) wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms, (6) The compound as defined in (1) wherein the ring B is a ring represented by the formula:

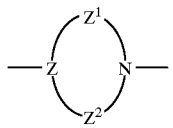

wherein Z is a nitrogen atom or a methyne group; $Z^1$ and $Z^2$ are independently a linear $C_{1-4}$ alkylene group which may be substituted by hydroxy, oxo or $C_{1-6}$ alkyl, (7) The compound as defined in (6) wherein $Z^1$ and $Z^2$ are independently a linear $C_{1-2}$ alkylene group, (8) The compound as defined in (1) wherein X is a bond, an oxygen atom or NH, (9) The compound as defined in (1) wherein X is a bond or an oxygen atom,

(10) The compound as defined in (1) wherein Y is a group represented by the formula:

—(CH$_2$)m—Y$^1$—(CH$_2$)n-Y$^2$— wherein $Y^1$ and $Y^2$ are the same or different and are independently a bond, an oxygen atom, S(O)p wherein p is an integer of 0 to 2, $NR^4$ wherein $R^4$ is a hydrogen atom or a lower alkyl group, a carbonyl group, a carbonyloxy group or a group represented by the formula:

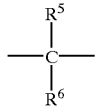

wherein $R^5$ and $R^6$ are the same or different and are independently a hydroxy group or a $C_{1-4}$ alkyl group; m and n are an integer of 0 to 4, and sum of m and n is not more than 6,

(11) The compound as defined in (1) wherein Y is
(i) a $C_{1-6}$ alkylene group,
(ii) —(CH$_2$)p$^1$O—,
(iii) —(CH$_2$)p$^1$NH—,
(iv) —(CH$_2$)p$^1$S—,
(v) —(CH$_2$)q$^1$CH(OH)(CH$_2$)q$^2$O—,
(vi) —(CH$_2$)q$^1$CH(OH)(CH$_2$)q$^2$NH—,
(vii) —(CH$_2$)q$^1$CH(OH)(CH$_2$)q$^2$S—,
(viii) —(CH$_2$)p$^1$CONH—,
(ix) —COO(CH$_2$)p$^1$O—,
(x) —COO(CH$_2$)p$^1$NH—,
(xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein $p^1$ is an integer of 1 to 6, $q^1$ and $q^2$ are an integer of 1 to 3,

(12) The compound as defined in (1) wherein $R^1$, $R^2$, $R^3$ and $R^7$ are the same or different and are independently (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group or (v) a carboxyl group,

(13) The compound as defined in (1) wherein $R^1$ is (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) a $C_{3-6}$ cycloalkyl group which may be substituted by $C_{1-6}$ alkoxy-carbonyl,

(14) The compound as defined in (1) wherein $R^2$ is a hydrogen atom, a $C_{1-6}$ alkyl group, a $C_{1-6}$ alkoxy-carbonyl group or a carboxyl group,

(15) The compound as defined in (1) wherein $R^3$ is a hydrogen atom,

(16) The compound as defined in (1) wherein $R^7$ is a hydrogen atom, a halogen atom, a $C_{1-6}$ alkyl group, a $C_{1-6}$ alkoxy-carbonyl group or a carboxyl group,

(17) The compound as defined in (1) wherein $R^8$ is a hydrogen atom or a hydroxy group,

(18) The compound as defined in (1) wherein A is a nitrogen atom,

(19) The compound as defined in (1) wherein A is $CR^{7'}$ wherein $R^{7'}$ is a hydrogen atom, a halogen atom, a $C_{1-6}$ alkyl group, a $C_{1-6}$ alkoxy-carbonyl group or a carboxyl group,

(20) The compound as defined in (1) wherein A is CH,

(21) The compound as defined in (1) wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms; the ring B is a ring represented by the formula:

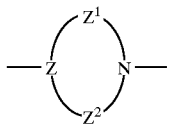

wherein Z is a nitrogen atom or a methyne group; $Z^1$ and $Z^2$ are independently a linear $C_{1-4}$ alkylene group which may be substituted by hydroxy, oxo or $C_{1-6}$ alkyl; X is a bond, an oxygen atom or NH; Y is
(i) a $C_{1-6}$ alkylene group,
(ii) —(CH$_2$)p$^1$O—,
(iii) —(CH$_2$)p$^1$NH—,
(iv) —(CH$_2$)p$^1$S—,
(v) —(CH$_2$)q$^1$CH(OH)(CH$_2$)q$^2$O—,
(vi) —(CH$_2$)q$^1$CH(OH)(CH$_2$)q$^2$NH—,
(vii) —(CH$_2$)q$^1$CH(OH)(CH$_2$)q$^2$S—,
(viii) —(CH$_2$)p$^1$CONH—,
(ix) —COO(CH$_2$)p$^1$O—,
(x) —COO(CH$_2$)p$^1$NH—,
(xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^1$ is (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) a $C_{3-6}$ cycloalkyl group which may be substituted by $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group,

(22) The compound as defined in (1) wherein $Ar^1$ and $Ar^2$ are independently a phenyl group; the ring B is a ring represented by the formula:

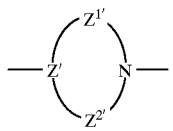

wherein Z' is a methyne group; $Z^{1'}$ and $Z^{2'}$ are independently an ethylene group; X is an oxygen atom or NH; Y is —$(CH_2)p^1NH$— wherein $p^1$ is an integer of 1 to 6; A is $CR^{7''}$ wherein $R^{7''}$ is a hydrogen atom or a $C_{1-6}$ alkyl group; $R^1$ is (i) a hydrogen atom, (ii) a $C_{1-6}$ alkyl group which may be substituted by carboxyl or $C_{1-6}$ alkoxy-carbonyl or (iii) a carbamoyl group which may be substituted by a $C_{1-6}$ alkyl group optionally having $C_{1-6}$ alkoxy-carbonyl; $R^2$ is a hydrogen atom; $R^3$ is a hydrogen atom; $R^8$ is a hydrogen atom,

(23) Ethyl 2-[6-[3-[4-(diphenylmethoxy)piperidino]propylamino]imidazo[1,2-b]pyridazin-2-yl]-2-methylpropionate or a difumarate thereof,

(24) 2-[6-[3-[4-(diphenylmethoxy)piperidino]propylamino] imidazo[1,2-b]pyridazin-2-yl]-2-methylpropionic acid or a salt thereof,

(25) Ethyl N-[6-[3-[4-(diphenylmethoxy)piperidino]propylamino]imidazo[1,2-b]pyridazine-2-carbonyl]glycinate or a salt thereof,

(26) Ethyl 2-[6-[3-[4-(diphenylmethoxy)piperidino]propylamino]-3-methylimidazo[1,2-b]pyridazin-2-yl]-2-methylpropionate or a dihydrochloride thereof,

(27) Ethyl 2-[6-[3-[4-(diphenylmethylamino)piperidino] propylamino]imidazo[1,2-b]pyridazin-2-yl]-2-methylpropionate or a salt thereof,

(28) A method for producing a compound as defined in (1), or a salt thereof which comprises reacting a compound represented by the formula:

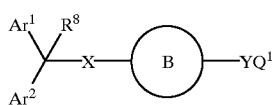

wherein $Q^1$ is a leaving group, and other symbols are same as defined in (1), or a salt thereof with a compound represented by the formula:

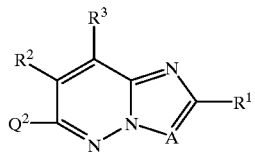

wherein $Q^2$ is a leaving group, and other symbols are same as defined in (1), or a salt thereof,

(29) A pharmaceutical composition which comprises the compound as defined in (1), or a salt thereof,

(30) An anti-histaminic agent or an eosinophil chemotaxis-inhibiting agent which comprises the compound as defined in (1), or a salt thereof,

(31) An anti-allergic agent which comprises the compound as defined in (1), or a salt thereof,

(32) An agent for treating or preventing asthma, allergic conjunctivitis, allergic rhinitis, chronic urticaria or atopic dermatitis,

(33) A method for suppressing a histamine or an eosinophil chemotaxis which comprises administering an effective amount of the compound as defined in (1) or a salt thereof to mammals,

(34) A method for treating or preventing allergic diseases which comprises administering an effective amount of the compound as defined in (1) or a salt thereof to mammals,

(35) A method for treating or preventing asthma, allergic conjunctivitis, allergic rhinitis, chronic urticaria or atopic dermatitis comprising administering an effective amount of the compound as defined in (1) or a salt thereof to mammals,

(36) Use of the compound as defined in (1) or a salt thereof for preparing an anti-histaminic agent or an eosinophil chemotaxis-inhibiting agent,

(37) Use of the compound as defined in (1) or a salt thereof for preparing an anti-allergic agent, and

(38) Use of the compound as defined in (1) or a salt thereof for preparing an agent for treating or preventing asthma, allergic conjunctivitis, allergic rhinitis, chronic urticaria or atopic dermatitis.

And, when the compound (I) or a salt thereof has asymmetric carbons, the present invention includes stereoisomers or racemates. The compound (I) or a salt thereof may be hydrades or unhydrades.

DETAILED DESCRIPTION

In the above mentioned formula (I), $Ar^1$ and $Ar^2$ are independently an aromatic group which may be substituted, and $Ar^1$ and $Ar^2$ may form a condensed cyclic ring with an adjacent carbon atom.

Examples of the aromatic group represented by $Ar^1$ and $Ar^2$ are (i) a single cyclic or condensed cyclic aromatic hydrocarbon group, preferably $C_{6-14}$ single cyclic or condensed cyclic aromatic hydrocarbon group such as $C_{6-14}$ aryl group (e.g. phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl, 9-phenanthryl, etc.), more preferably phenyl, tolyl, xylyl, biphenyl, 1-naphthyl, 2-naphthyl, particularly phenyl, etc., (ii) a single cyclic group (preferably 5 to 8 membered single cyclic group) containing more than 1 (for example 1 to 4, preferably 1 to 3) and one or more than two kinds of hetero atoms selected from a nitrogen atom, a sulfur atom and an oxygen atom other than carbon atoms, or a condensed aromatic heterocyclic group thereof, preferably an aromatic hetero ring removed a hydrogen atom from, such as thiophene, benzo[b]thiophene, benzo[b]furan, benzimidazole, benzoxazole, benzothiazole, benzisothiazole, naphtho[2,3-b]thiophene, thianthrene, furan, isoindolylzine, xanthene, phenoxathiin, pyrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine, naphthylidine, quinoxaline, quinazoline, cinnoline, carbazole, β-carboline, phenanthridine, acridine, phenazine, isothiazole, phenothiazine, isoxazole, furaxan, phenoxazine and isochroman, preferably pyridine, thiophene, furan, more preferably pyridine, and (iii) a group removed a hydrogen atom from the condensed ring formed by the above mentioned ring (preferably the single ring as mentioned above) and one or few (preferably 1 or 2, more preferably 1) aromatic ring (for example the above mentioned aromatic hydrocarbon group, more preferably benzene ring, etc.), and so on.

More preferable examples of the aromatic ring represented by $Ar^1$ and $Ar^2$ are phenyl, etc.

Examples of the substituents of the aromatic ring represented by $Ar^1$ and $Ar^2$ are (i) a halogen atom (e.g. fluorine, chlorine, bromine, iodine),
(ii) lower alkylenedioxy (e.g. $C_{1-3}$ alkylenedioxy such as methylenedioxy, ethylenedioxy),
(iii) nitro,
(iv) cyano,
(v) optionally halogenated lower alkyl,
(vi) optionally halogenated lower alkenyl,
(vii) optionally halogenated lower alkynyl,
(viii) lower cycloalkyl (e.g. $C_{3-6}$ cycloalkyl such as cyclopropyl, cyclobuthyl, cyclopenthyl, cyclohexyl),
(ix) optionally halogenated lower alkoxy,
(x) optionally halogenated lower alkylthio,
(xi) hydroxy,
(xii) amino,
(xiii) mono-lower alkylamino (e.g. mono-$C_{1-6}$ alkylamino such as methylamino, ethylamino, propylamino, isopropylamino, buthylamino),
(xiv) di-lower alkylamino (e.g. di-$C_{1-6}$ alkylamino such as dimethylamino, diethylamino, dipropylamino, dibuthylamino),
(xv) 5 or 6 membered cyclic amino (e.g. morpholino, pyperadin-1-yl, pyperidino, pyroridin-1-yl),
(xvi) lower alkylcarbonyl (e.g. $C_{1-6}$ alkylcarbonyl such as formyl, acetyl, propionyl),
(xvii) carboxyl,
(xviii) lower alkoxy-carbonyl (e.g. $C_{1-6}$ alkoxy-carbonyl such as methoxycarbonyl, ethoxycarbonyl, propoxycarbonyl, butoxycarbonyl),
(xix) carbamoyl;
(xx) mono-lower alkyl-carbamoyl (e.g. mono-$C_{1-6}$alkyl-carbamoyl such as methylcarbamoyl, ethylcarbamoyl),
(xxi) di-lower alkyl-carbamoyl (e.g. di-$C_{1-6}$ alkyl-carbamoyl such as dimethylcarbamoyl, diethylcarbamoyl),
(xxii) aryl-carbamoyl (e.g. $C_{6-10}$ aryl-carbamoyl such as phenylcarbamoyl, naphthylcarbamoyl),
(xxiii) sulfo,
(xxiv) lower alkyl sulfonyl (e.g. $C_{1-6}$ alkyl sulfonyl such as methylsulfonyl, ethylsulfonyl),
(xxv) aryl (e.g. $C_{6-10}$ aryl such as phenyl, naphtyl) or
(xxvi) aryloxy (e.g. $C_{6-10}$ aryloxy such as phenyloxy, naphthyloxy).
(xxvii) aralkyloxy group (e.g. $C_{7-16}$ aralkyloxy such as benzyloxy),
(xxviii) oxo, and so on.

Examples of the optionally halogenated lower alkyl are lower alkyls (e.g. $C_{1-6}$ alkyl such as methyl, ethyl, propyl, isopropyl, butyl, isobutyl, sec-butyl, tert-butyl, penthyl, hexyl) optionally substituted by 1 to 3 halogen atoms (e.g. fluorine, chlorine, bromine, iodine) and so on. Specific examples of the optionally halogenated lower alkyl are methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, penthyl, isopentyl, neopentyl, 5,5,5-trifluoropentyl, hexyl, 6,6,6-trifluorohexyl and so on.

Examples of the optionally halogenated lower alkenyl are lower alkenyls (e.g. $C_{2-6}$ alkenyl such as vinyl, propenyl, isopropenyl, 2-buten-1-yl, 4-penthen-1-yl, 5-hexen-1-yl) optionally substituted by 1 to 3 halogen atoms (e.g. fluorine, chlorine, bromine, iodine) and so on.

Examples of the optionally halogenated lower alkynyl are lower alkynyls (e.g. $C_{2-6}$ alkynyl such as 2-butyn-1-yl, 4-pentyn-1-yl, 5-hexyn-1-yl) optionally substituted by 1 to 3 halogen atoms (e.g. fluorine, chlorine, bromine, iodine) and so on.

Examples of the optionally halogenated lower alkoxy are lower alkoxys (e.g. $C_{1-6}$ alkoxy such as methoxy, ethoxy, propoxy, isopropoxy, n-butoxy, isobutoxy, sec-butoxy, tert-butoxy) optionally substituted by 1 to 3 halogen atoms (e.g. fluorine, chlorine, bromine, iodine), mono- or di-lower alkylamino (e.g. mono- or di-$C_{1-6}$ alkylamino such as methylamino, dimethylamino, ethylamino, dimethylamino) or lower alkoxy-carbonyl (e.g. $C_{1-6}$ alkoxy-carbonyl such as methoxycarbonyl, ethoxycarbonyl) and so on.

Examples of the optionally halogenated lower alkylthio are lower alkylthios (e.g. $C_{1-6}$ alkylthio such as methylthio, ethylthio, n-propylthio, isopropylthio, n-butylthio, isobutylthio, sec-butylthio, tert-butylthio) optionally substituted by 1 to 3 halogen atoms (e.g. fluorine, chlorine, bromine, iodine) and so on. Specific examples of the optionally halogenated lower alkylthio are methylthio, difluoromethylthio, trifluoromethylthio, ethylthio, propylthio, isopropylthio, butylthio, 4,4,4-trifluorobutylthio, penthylthio, hexylthio and so on.

Specific examples of the condensed ring formed by $Ar^1$, $Ar^2$ and the adjacent carbon atom are a condensed ring represented by the formula:

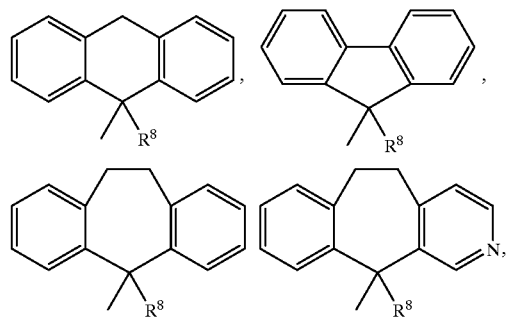

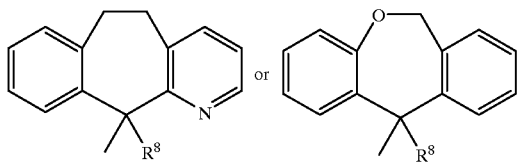

wherein $R^8$ is same as defined above.

Preferable examples of $Ar^1$ and $Ar^2$ are the same or different and are independently an aromatic hydrocarbon group (preferably $C_{6-14}$ aromatic hydrocarbon group) which may be substituted, and a benzene ring which may be substituted is more preferred.

More preferable examples of $Ar^1$ and $Ar^2$ are independently (i) a benzene ring which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms, and so on.

In the above mentioned formula (I), the ring B represents a nitrogen-containing heterocycle which may be substituted.

Examples of the nitrogen-containing heterocycle represented by the ring B are a 3 to 13 membered nitrogen-containing heterocycle containing at least one nitrogen atom which may contain 1 to 3 hetero atoms selected by a nitrogen atom, an oxygen atom and a sulfur atom, and so on.

In the above mentioned formula (I), examples of the ring B are a bivalent group removed one hydrogen atom from the nitrogen atom and others atom of the ring B, respectively. Specific examples are a 3 to 9 membered (preferably 3 to 6 membered) nitrogen atom-containing heterocyclic group such as

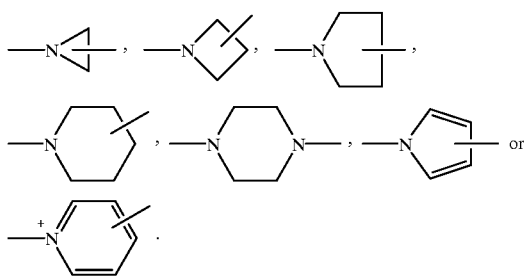

Examples of the substituents of the nitrogen atom-containing heterocycle represented by the ring B are the substituents of the aromatic group represented by $Ar^1$ and $Ar^2$ as mentioned above, and so on.

Specific preferable examples of the ring B are a ring represented by the formula:

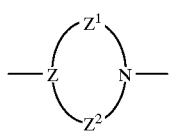

wherein Z is a nitrogen atom or a methyne group, $Z^1$ and $Z^2$ are independently a linear $C_{1-4}$ alkylene group which may be substituted by hydroxy, oxo or $C_{1-6}$ alkyl, and so on.

Examples of the $C_{1-6}$ alkyl group are a linear or branched $C_{1-6}$ alkyl group such as methyl, ethyl, propyl, isopropyl, butyl, isobutyl, sec-butyl, tert-butyl, pentyl, hexyl and so on.

Examples of the linear $C_{1-4}$ alkylene group are a linear $C_{1-4}$ alkylene group such as methylene, ethylene, propylene, butylene and so on.

Examples of the linear $C_{1-4}$ alkylene group which may be substituted by hydroxy, oxo or $C_{1-6}$ alkyl are an unsubstituted linear $C_{1-4}$ alkylene group, and an unsubstituted linear $C_{1-2}$ alkylene group is more preferred.

More preferable examples of the ring B are piperidine, piperazine and so on.

In the above mentioned formula, X and Y are the same or different and are independently a bond, an oxygen atom, $S(O)p$ (p is an integer of 0 to 2), $NR^4$ wherein $R^4$ is a hydrogen atom or a lower alkyl group, or a bivalent linear lower hydrocarbon group which may contain 1 to 3 hetero atoms and the bivalent linear lower hydrocarbon group may have substituents.

Examples of the lower alkyl group represented by $R^4$ are a linear or branched $C_{1-6}$ alkyl group such as methyl, ethyl, propyl, isopropyl, butyl, isobutyl, sec-butyl, tert-butyl, pentyl, hexyl and so on.

Examples of the bivalent linear lower hydrocarbon group represented by X and Y are a group which is formed by removing each one hydrogen atom (sum two hydrogen atoms) bonded to same or different carbon atom from a lower ($C_{1-6}$) hydrocarbon, and which may optionally contain hetero atoms selected from an oxygen atom and a sulfur atom in the hydrocarbon chain.

Specific examples of the bivalent linear lower hydrocarbon group are
(i) $C_{1-6}$ alkylene group such as —$CH_2$—, —$(CH_2)_2$—, —$(CH_2)_3$—, —$(CH_2)_4$—, —$(CH_2)_5$— and —$(CH_2)_6$—,
(ii) $C_{2-6}$ alkenylene group such as —CH=CH—, —CH=CH—$CH_2$—, —$CH_2$—CH=CH—$CH_2$, —$(CH_2)_2$—CH=CH—$CH_2$, —$(CH_2)_2$—CH=CH—$(CH_2)_2$— and —$(CH_2)_3$—CH=CH—$CH_2$—,
(iii) $C_{2-6}$ alkynylene such as —C≡C—, —C≡C—$CH_2$—, —$CH_2$—C≡C—$CH_2$—, —$(CH_2)_2$—C≡C—$CH_2$—, —$(CH_2)_2$—C≡C—$(CH_2)_2$— and —$(CH_2)_3$—C≡C—$CH_2$—, and so on.

Examples of the substituents of the bivalent linear lower hydrocarbon group which may contain 1 to 3 hetero atoms represented by X and Y are the substituents of the aromatic group which may be substituted represented by the above mentioned $Ar^1$ and $Ar^2$, and hydroxy or oxo is particularly preferred.

Preferable examples of X are a bond, an oxygen atom or NH, and a bond or an oxygen atom is more preferred.

Preferable examples of Y are a group represented by the formula:

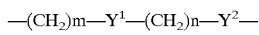
—$(CH_2)m$—$Y^1$—$(CH_2)n$—$Y^2$— wherein $Y^1$ and $Y^2$ are the same or different and are independently a bond, an oxygen atom, $S(O)p$ wherein p is same as defined above, $NR^4$ wherein $R^4$ is same as defined above, a carbonyl group, a carbonyloxy group or a group represented by the formula:

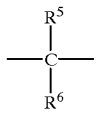

wherein $R^5$ and $R^6$ are the same or different and are independently a hydroxy group or a $C_{1-4}$ alkyl group; m and n are independently an integer of 0 to 4, and sum of m and n is not more than 6, and so on.

Examples of the $C_{1-4}$ alkyl group represented by $R^5$ and $R^6$ are a linear or branched $C_{1-4}$ alkyl group such as methyl, ethyl, propyl, isopropyl, butyl, isobutyl, sec-butyl, tert-butyl and so on.

More preferable examples of Y are
(i) a $C_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3, and so on.

Of them, a bond, —$(CH_2)_2$—O—, —$(CH_2)_3$—O—, —$(CH_2)_4$—O—, —$(CH_2)_6$—O—, —$(CH_2)_2$—NH—, —$(CH_2)_3$—NH—, —$(CH_2)_4$—NH—, —$(CH_2)_3$—S—, —$CH_2$—CH(OH)—$CH_2$—O—, —$(CH_2)_2$—CO—NH—, —$CH_2$—CO—NH—, —CO—O—$(CH_2)_2$—O—, —CO—O—$(CH_2)_3$—O—, —$(CH_2)_6$—NH—, —$(CH_2)_6$—S—, —$(CH_2)_6$—O—, —$(CH_2)_2$—O—$(CH_2)_2$—O—, —$(CH_2)_2$—O—$(CH_2)_2$—S—, etc. are preferred.

In the above mentioned formula (I), A is a nitrogen atom or $CR^7$ wherein $R^7$ is a hydrogen atom, a halogen atom, a hydrocarbon group which may be substituted, an acyl group or a hydroxy group which may be substituted.

Examples of the halogen atom represented by $R^7$ are fluorine, chlorine, bromine or iodine.

Examples of the hydrocarbon group represented by $R^7$ is a group removed one hydrogen atom from the hydrocarbon compound and so on. Specific examples are a linear and cyclic hydrocarbon group such as alkyl group, alkenyl group, alkynyl group, cycloalkyl group, aryl group, aralkyl group and so on. Of them, $C_{1-16}$ chain (linear or branched) or cyclic hydrocarbon group, and more preferable examples are (a) alkyl group, preferably lower alkyl group (e.g. $C_{1-6}$ alkyl group such as methyl, ethyl, propyl, isopropyl, butyl, isobutyl, sec-butyl, tert-butyl, penthyl, hexyl),
(b) alkenyl group, preferably lower alkenyl group (e.g. $C_{2-6}$ alkenyl such as vinyl, allyl, isopropenyl, butenyl, isobutenyl, sec-butenyl),
(c) alkynyl group, preferably lower alkynyl (e.g. $C_{2-6}$ alkynyl such as propargyl, ethynyl, butynyl, 1-hexynyl),
(d) cycloalkyl group, preferably lower cycloalkyl (e.g. $C_{3-6}$ cycloalkyl such as cyclopropyl, cyclobutyl, cyclopenthyl, cyclohexyl which may condense with a benzene ring optionally having 1 to 3 lower alkoxys (e.g. $C_{1-6}$ alkoxy such as methoxy)),
(e) aryl group (e.g. $C_{6-14}$ aryl group such as phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl or 9-phenanthryl, preferably phenyl),
(f) aralkyl group (e.g. $C_{7-16}$ aralkyl group such as benzyl, phenetyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl or 5-phenylpentyl, preferably benzyl).

Examples of the substituents of the hydrocarbon group represented by $R^7$ are the substituents of the aromatic group represented by the above mentioned $Ar^1$ and $Ar^2$.

Examples of the acyl group represented by $R^7$ are —(C=O)—$R^9$, —$SO_2$—$R^9$, —SO—$R^9$, —(C=O)NR$^{10}$R$^9$, —(C=O)O—$R^9$, —(C=S)O—$R^9$ or —(C=S)NR$^{10}$R$^9$ wherein $R^9$ is a hydrogen atom, a hydrocarbon group which may be substituted or a hydroxy group which may be substituted; and $R^{10}$ is a hydrogen atom or a lower alkyl group (e.g. a $C_{1-6}$ alkyl group such as methyl, ethyl, propyl, isopropyl, butyl, isobutyl, tert-butyl, pentyl, hexyl and so on, preferably a $C_{1-3}$ alkyl such as methyl, ethyl, propyl, isopropyl and so on).

Of them, —(C=O)—$R^9$, —$SO_2$—$R^9$, —SO—$R^9$, —(C=O)NR$^{10}$R$^9$, —(C=O)O—$R^9$ are preferred, and —(C=O)—$R^9$ is more preferred.

Examples of the hydrocarbon group represented by $R^9$ is a group removed one hydrogen atom from the hydrocarbon compound. Specific examples are chained (linear or branched) or cyclic hydrocarbon group such as alkyl group, alkenyl group, alkynyl group, cycloalkyl group, aryl group, aralkyl group and so on. Specifically, the hydrocarbon group represented by the above mentioned $R^7$, etc. are used. Of them, $C_{1-16}$ linear or cyclic hydrocarbon group, etc. are preferred and a lower ($C_{1-6}$) alkyl group, etc. are more preferred.

Examples of the substituents of the hydrocarbon group represented by $R^9$ are same substituents of the aromatic group represented by the above mentioned $Ar^1$ and $Ar^2$, and so on.

Examples of the hydroxy group which may be substituted represented by $R^7$ are (i) a hydroxy group or (ii) a hydroxy group substituted by one group such as the above mentioned hydrocarbon group which may be substituted instead of a hydrogen atom of the hydroxy group.

Preferable examples of $R^7$ are (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group, (v) a carboxyl group and so on, and particularly a hydrogen atom, a halogen atom, a $C_{1-6}$ alkyl group, a $C_{1-6}$ alkoxy-carbonyl group and a carboxyl group are preferred.

Preferable examples of A are a nitrogen atom, $CR^{7'}$ wherein $R^{7'}$ is a hydrogen atom, a halogen atom, a $C_{1-6}$ alkyl group, a $C_{1-6}$ alkoxy-carbonyl group or a carboxyl group, and particularly a nitrogen atom and CH are preferred.

In the above mentioned formula (I), $R^1$, $R^2$ and $R^3$ are the same or different and are independently a hydrogen atom, a halogen atom, a hydrocarbon group which may be substituted, an acyl group or a hydroxy group which may be substituted.

Examples of the halogen atom represented by $R^1$, $R^2$ and $R^3$ are fluorine, chlorine, bromine, iodine and so on.

Examples of the hydrocarbon group represented by $R^1$, $R^2$ and $R^3$ are the hydrocarbon group represented by $R^7$ and so on.

Examples of the acyl group represented by $R^1$, $R^2$ and $R^3$ are the acyl group represented by $R^7$ and so on.

Examples of the hydroxy group which may be substituted represented by $R^1$, $R^2$ and $R^3$ are the hydroxy group which may be substituted represented by $R^7$ and so on.

Preferable examples of $R^1$, $R^2$ and $R^3$ are the same or different and are independently (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group, (v) a carboxyl group, (vi) a $C_{6-14}$ aryl group (preferably phenyl) and so on, and (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group and (v) a carboxyl group are more preferred.

More preferable examples of $R^1$ is (i) a hydrogen atom, (ii) a $C^{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group may be substituted by a $C_{1-6}$ alkyl group optionally having carboxyl or $C_{1-6}$ alkoxy-carbonyl or (viii) $C_{3-6}$ cycloalkyl group which may be substituted by $C_{1-6}$ alkoxy-carbonyl, and so on.

Preferable examples of $R^2$ are a hydrogen atom, a $C_{1-6}$ alkyl group, a $C_{1-6}$ alkoxy-carbonyl group, a carboxyl group, and so on.

Preferable examples of $R^3$ are a hydrogen atom, and so on.

In the above mention formula (I), $R^8$ is a hydrogen atom or a hydroxy group which may be substituted by lower alkyl.

Examples of the lower alkyl represented by $R^8$ are a $C_{1-6}$ alkyl group such as methyl, ethyl, propyl, isopropyl, butyl, isobutyl, sec-butyl, tert-butyl, pentyl, hexyl and so on.

Preferable examples of $R^8$ are a hydrogen atom, a hydroxyl group and so on, and particularly a hydrogen atom is more preferred.

Preferable examples of the compound (I) of the present invention are a compound wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms; the ring B is a ring represented by the formula:

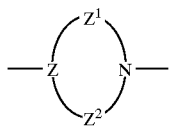

wherein Z is a nitrogen atom or a methyne group; $Z^1$ and $Z^2$ is independently a linear $C_{1-4}$ alkylene group which may be substituted by hydroxy, oxo or $C_{1-6}$ alkyl; X is a bond, an oxygen atom or NH; Y is
(i) a $C_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O (CH_2)q^2NH$— or
(xiv) —$(CH_2)q^1O(CH_2)q^2S$— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^1$ is (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) $C_{3-6}$ cycloalkyl group which may be substituted by $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group, and so on.

Particularly, a compound wherein $Ar^1$ and $Ar^2$ are a phenyl group; the ring B is a ring represented by the formula:

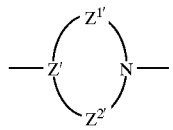

wherein $Z'$ is a methyne group; $Z^{1'}$ and $Z^{2'}$ are an ethylene group; X is an oxygen atom or NH; Y is —$(CH_2)p^1NH$— wherein $p^1$ is an integer of 1 to 6; A is $CR^{7''}$ wherein $R^{7''}$ is a hydrogen atom or a $C_{1-6}$ alkyl group; $R^1$ is (i) a hydrogen atom, (ii) a $C_{1-6}$ alkyl group which may be substituted by carboxyl or $C_{1-6}$ alkoxy-carbonyl or (iii) a $C_{1-6}$ alkoxy group which may be substituted by a $C_{1-6}$ alkyl group optionally having $C_{1-6}$ alkoxy-carbonyl; $R^2$ is a hydrogen atom; $R^3$ is a hydrogen atom; $R^8$ is a hydrogen atom, etc. are more preferred.

More specific examples of the compound of the present invention are

Ethyl 2-[6-[3-[4-(diphenylmethoxy)piperidino]propylamino]imidazo[1,2-b]pyridazin-2-yl]-2-methylpropionate or a salt thereof (particularly, a difumarate thereof), 2-[6-[3-[4-(diphenylmethoxy)piperidino]propylamino]imidazo[1,2-b]pyridazin-2-yl]-2-methylpropionic acid or a salt thereof, Ethyl N-[6-[3-[4-(diphenylmethoxy)piperidino]propylamino]imidazo[1,2-b]pyridazine-2-carbonyl]glycinate or a salt thereof, Ethyl 2-[6-[3-[4-(diphenylmethoxy)piperidino]propylamino]-3-methylimidazo[1,2-b]pyridazin-2-yl]-2-methylpropionate or a salt thereof (particularly, a dihydrochloride thereof), Ethyl 2-[6-[3-[4-(diphenylmethylamino)piperidino]propylamino]imidazo[1,2-b]pyridazin-2-yl]-2-methylpropionate or a salt thereof, and so on.

The compound (I) of the present invention or a salt thereof can be produced by reacting a compound represented by the formula:

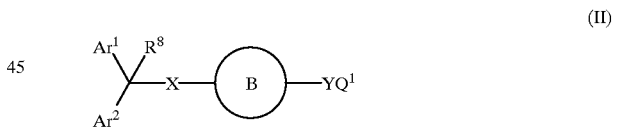

(II)

wherein $Q^1$ represents a leaving group; the other symbols have the same definitions as those shown above, or a salt thereof, with a compound represented by the formula:

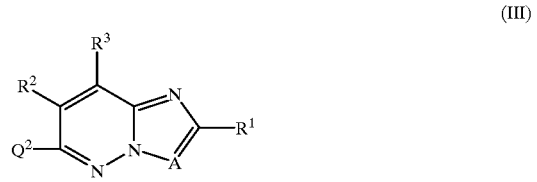

(III)

wherein $Q^2$ represents a leaving group; the other symbols have the same definitions as those shown above, or a salt thereof.

Examples of the leaving group represented by $Q^1$ are alkali metals such as sodium and potassium. $Q^1$ may be a hydrogen atom.

Examples of the leaving group represented by $Q^2$ are a halogen group (e.g., chloro, bromine, iodine), a $C_{6-10}$ arylsulfonyloxy group (e.g., benzenesulfonyloxy, p-tolylsulfonyloxy) and a $C_{1-4}$ alkyl-sulfonyloxy group (e.g., methanesulfonyloxy).

In this reaction, the compound (III) or a salt thereof is normally used at 1 to 5 mol, preferably 1 to 2 mol, per mol of the compound (II) or a salt thereof. This condensation reaction is preferably carried out in the presence of a base. Examples of the base are alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Also, the compound (I) of the present invention or a salt thereof can be produced by reacting a compound represented by the formula:

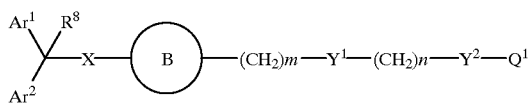

(IV)

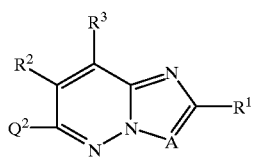

(III)

wherein the symbols have the same definitions as those shown above, or a salt thereof, with a compound represented by the formula:

wherein the symbols have the same definitions as those shown above, or a salt thereof.

In this reaction, the compound (III) or a salt thereof is normally used at 1 to 5 mol, preferably 1 to 2 mol, per mol of the compound (IV) or a salt thereof. This condensation reaction is preferably carried out in the presence of a base. Examples of the base are alkali metal hydrides such as sodium hydride and potassium hydride; alkali metal alkoxides such as sodium methoxide and sodium ethoxide; alkali metal hydroxides such as sodium hydroxide and potassium hydroxide; and carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Also, compound (I) of the present invention or a salt thereof can be produced by reacting a compound represented by the formula:

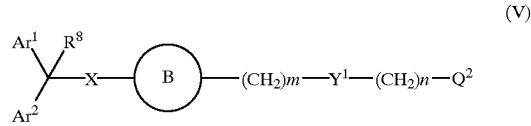

(V)

wherein the symbols have the same definitions as those shown above, or a salt thereof, with a compound represented by the for

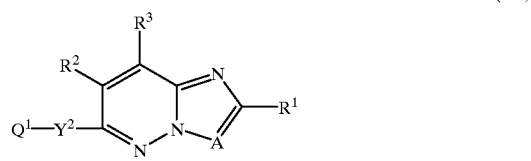

(VI')

wherein the symbols have the same definitions as those shown above, or a salt thereof.

In this reaction, the compound (VI') or a salt thereof is normally used at 1 to 5 mol, preferably 1 to 2 mol, per mol of the compound (V) or a salt thereof. This condensation reaction is preferably carried out in the presence of a base. Examples of the base are alkali metal hydrides such as sodium hydride and potassium hydride; alkali metal alkoxides such as sodium methoxide and sodium ethoxide; alkali metal hydroxides such as sodium hydroxide and potassium hydroxide; and carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitrites such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Also, compound (I) of the present invention or a salt thereof can be produced by reacting a compound represented by the formula:

(VII)

wherein the symbols have the same definitions as those shown above, or a salt thereof, with a compound represented by the formula:

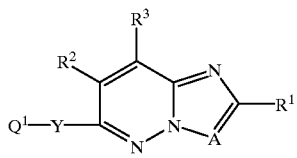

(VI)

wherein the symbols have the same definitions as those shown above, or a salt thereof.

In this reaction, the compound (VII) or a salt thereof is normally used at 1 to 5 mol, preferably 1 to 2 mol, per mol of the compound (VI) or a salt thereof. This condensation reaction is preferably carried out in the presence of a base. Examples of the base alkali metal hydrides such as sodium hydride and potassium hydride; alkali metal alkoxides such as sodium methoxide and sodium ethoxide; alkali metal hydroxides such as sodium hydroxide and potassium hydroxide; and carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitrites such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Also, compound (I) of the present invention or a salt thereof can be produced by reacting a compound represented by the formula:

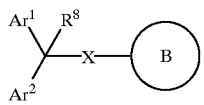

(VII)

wherein the symbols have the same definitions as those shown above, or a salt thereof, with a compound represented by the formula:

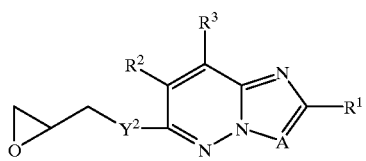

(VIII)

wherein the symbols have the same definitions as those shown above, or a salt thereof.

In this reaction, the compound (VIII) or a salt thereof is normally used at 1 to 5 mol, preferably 1 to 2 mol, per mol of the compound (VII) or a salt thereof.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

When the compound (I) is obtained in free form, it can be converted into a salt by a conventional method. When the compound (I) is obtained as a salt, it can be converted into a free form or another salt by a conventional method. The compound (I) or a salt thereof thus obtained can be isolated and purified by known means such as solvent extraction, pH ajustment, liquid-liquid transformation, saltingout, crystallization, recrystallization and chromatography. When the compound (I) or a salt thereof contains optical isomers, it can be resoluted into the R- and S-configurations by an ordinary means of optical resolution.

Hereinafter described are methods of producing staring compounds (II) to (VIII) or salts thereof which are used to produce the compound (I) or a salt thereof. Salts of these compounds include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methanesulfonic acid, benzenesulfonic acid). Provided that these compounds have an acidic group such as that of a carboxylic acid, as a substituent thereof, the acidic group may form a salt with an inorganic base (e.g., an alkali metal or alkaline earth metal such as sodium, potassium, calcium or magnesium, or ammonia) or an organic base (e.g., a tri-$C_{1-3}$ alkylamine such as triethylamine).

The starting compounds (II) and (IV) or salts thereof can, for example, be synthesized by the method described in the Journal of Medicinal Chemistry, Vol. 32, p. 583 (1989), or a modification thereof.

The starting compound (III) or a salt thereof can, for example, be synthesized by the method described in the Journal of Organic Chemistry, Vol. 39, p. 2143 (1974) or a modification thereof.

The starting compound (V) or a salt thereof can, for example, be synthesized by the methods described in Japanese Patent Unexamined Publication No. 2739/1987 etc., or modifications thereof.

The starting compounds (VI) and (VIII) or salts thereof can, for example, be synthesized by the methods described in Japanese Patent Unexamined Publication No. 223287/1991, or modifications thereof.

The starting compound (VII) or a salt thereof can, for example, be synthesized by the method described in the Journal of Medicinal Chemistry, Vol. 38, p. 2472 (1995), or a modification thereof.

Although these starting compounds or salts thereof thus obtained can be isolated and purified by known means such as solvent extraction, pH ajustment, liquid-liquid transformation, salting-out, crystallization, recrystallization and chromatography, they may be used as starting materials for the next process, in the form of reaction mixture without purification.

Also, when the starting compound used in each of the reactions for synthesizing the above-described desired compounds and starting compounds has an amino group, a carboxyl group or a hydroxyl group as a substituent, these substituents may have a protective group in common use in peptide chemistry etc.; the desired compound can be obtained by removing, as appropriate, the protective group after completion of the reaction.

The amino group-protecting groups include, for example, formyl, $C_{1-6}$ alkylcarbonyls that may have a substituent (e.g., acetyl, ethylcarbonyl), phenylcarbonyl, $C_{1-6}$ alkyl-oxycarbonyls (e.g., methoxycarbonyl, ethoxycarbonyl), phenyloxycarbonyl, $C_{7-10}$ aralkyl-carbonyls (e.g., benzylcarbonyl), trityl, phthaloyl and N,N-dimethylaminomethylene. Substituents for these groups include halogen atoms (e.g., fluoro, chloro, bromine, iodine), $C_{1-6}$ alkyl-carbonyls (e.g., methylcarbonyl, ethylcarbonyl, butylcarbonyl) and nitro groups, the number of substituents being about 1 to 3.

The carboxyl group-protecting groups include, for example, $C_{1-6}$ alkyls that may have a substituent (e.g., methyl, ethyl, n-propyl, isopropyl, n-butyl, tert-butyl), phenyl, trityl and silyl. Substituents for these groups include halogen atoms (e.g., fluoro, chloro, bromine, iodine), formyl, $C_{1-6}$ alkyl-carbonyls (e.g., acetyl, ethylcarbonyl, butylcarbonyl) and nitro groups, the number of substituents being about 1 to 3.

The hydroxyl group-protecting groups include, for example, $C_{1-6}$ alkyls that may have a substituent (e.g., methyl, ethyl, n-propyl, isopropyl, n-butyl, tert-butyl), phenyl, $C_{7-10}$ aralkyls (e.g., benzyl), formyl, $C_{1-6}$ alkyl-carbonyls (e.g., acetyl, ethylcarbonyl), phenyloxycarbonyl, benzoyl, $C_{7-10}$ aralkyl-carbonyls (e.g., benzylcarbonyl), pyranyl, furanyl and silyl. Substituents for these groups include halogen atoms (e.g., fluoro, chloro, bromine, iodine), $C_{1-6}$ alkyls (e.g., methyl, ethyl, n-propyl), phenyl, $C_{7-10}$ aralkyls (e.g., benzyl) and nitro groups, the number of substituents being about 1 to 4.

The protecting groups can be removed by commonly known methods or modifications thereof, including treatments with acids, bases, reducing agents, ultraviolet rays, hydrazine, phenylhydrazine, sodium N-methyldithiocarbamate, tetrabutylammonium fluoride, palladium acetate etc.

The compound (I) of the present invention or a salt thereof can be safely used as an anti-allergic agent in mammals (e.g., human, mice, dogs, rats, bovines), because it exhibits excellent anti-allergic, anti-histaminic, anti-inflammatory, anti-PAF (platelet activating factor) or eosinophil chemotaxis inhibiting activity, etc., with low toxicity (acute toxicity: $LD_{50}$>2 g/kg). The compound (I) or a salt thereof exhibits an eosinophil chemotaxis inhibiting activity as well as an anti-histaminic activity, and can be used to treat or prevent allergic diseases such as chronic urticaria, atopic dermatitis, allergic rhinitis, allergic conjunctivitis and hypersensitive pneumonitis; dermal diseases such as eczema, herpetic dermatitis and psoriasis; and respiratory diseases such as eosinophilic pneumonia (PIE syndrome), and asthma, etc., in the above-mentioned mammals. Preferably, the compound (I) or a salt thereof is used as an agent for treating or preventing asthma, allergic conjunctivitis, allergic rhinitis, chronic urticaria, atopic dermatitis etc. Route of administration may be oral or another route.

Also, the preparation for the present invention may contain as active ingredients pharmaceutical components other than the compound (I) or a salt thereof. Such pharmaceutically active components include, for example, anti-asthmatics (e.g., theophylline, procaterol, ketotifen, azelastine, seratrodast), anti-allergic agents (e.g., ketotifen, terfenadine, azelastine, epinastine), anti-inflammatory agents (e.g., diclofenac sodium, ibuprofen, indomethacin), antibacterial agents (e.g., cefixime, cefdinir, ofloxacin, tosufloxacin) and antifungal agents (e.g., fluconazole, itraconazole). These components are not subject to limitation, as long as the object of the present invention is accomplished, and may be used in appropriate mixing ratios. Useful dosage forms include, for example, tablets (including sugar-coated tablets and film-coated tablets), pills, capsules (including microcapsules), granules, fine subtilaes, powders, syrups, emulsions, suspensions, injectable preparations, inhalants and ointments. These preparations are prepared by conventional methods (e.g., methods described in the Pharmacopoeia of Japan).

In the preparation of the present invention, the content of the compound (I) or a salt thereof is normally 0.01 to 100% by weight, preferably 0.1 to 50% by weight, and more preferably 0.5 to 20% by weight, relative to the entire preparation, depending on the form of the preparation.

Specifically, tablets can be produced by granulating a pharmaceutical as-is, or in a uniform mixture with excipients, binders, disintegrating agents and other appropriate additives, by an appropriate method, then adding lubricants etc., and subjecting the mixture to compressive shaping, or by subjecting to direct compressive shaping a pharmaceutical as-is, or in a uniform mixture with excipients, binders, disintegrating agents and other appropriate additives, or subjecting to compressive shaping previously prepared granules as-is, or in a uniform mixture with appropriate additives. These tablets may incorporate coloring agents, correctives etc. as necessary, and may be coated with appropriate coating agents.

Injectable preparations can be produced by dissolving, suspending or emulsifying a given amount of a pharmaceutical in an aqueous solvent such as water for injection, physiological saline or Ringer's solution, or a non-aqueous solvent such as a vegetable oil, and diluting to a given amount, or transferring a given amount of a pharmaceutical into a container for injection and sealing the container.

Examples of the carriers for oral preparations are substances in common use in pharmaceutical production, such as starch, mannitol, crystalline cellulose and carboxymethyl cellulose sodium. Examples of the carriers for injectable preparations are distilled water, physiological saline, glucose solutions and transfusions. Other additives in common use for pharmaceutical production can also be added, as appropriate.

Depending on patient age, body weight, symptoms, route and frequency of administration and other factors, the daily dose of these preparations is normally 0.1 to 100 mg/kg, preferably 1 to 50 mg/kg, and more preferably 1 to 10 mg/kg, based on daily dose of active ingredient (the compound (I) or a salt thereof), once or in two portions daily for each asthmatic adult.

Modes of Working the Invention

The present invention is hereinafter described in more detail by means of the following examples, reference examples, formulation examples and experimental examples, which are not to be construed as limitative.

In the examples and reference examples below, the fraction containing the desired product was detected by observation via TLC (thin-layer chromatography). In the TLC observation, $60F_{254}$, produced by Merck, was used as a TLC plate, with a UV detector as a means of detection.

EXAMPLE 1

Production of 6-[3-[4-(diphenylmethyl)piperazino]propoxy][1,2,4]triazolo[1,5-b]pyridazine dihydrochloride 4-(Diphenylmethyl)-1-piperazinepropanol (466 mg) was dissolved in dried-tetrahyfrofuran (10 ml), followed by addition of sodium t-butoxide (173 mg). The mixture was refluxed under heating for 30 minutes. After the mixture was cooled, 6-chloro[1,2,4]triazolo[1,5-b]pyridazine (268 mg) was added to the mixture. The resulting mixture was refluxed under heating for 3 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (10:1). Fractions containing the objective compound were collected and dissolved in ethyl acetate (10 ml), followed by addition of 4N HCl-ethyl acetate solution (0.7 ml). The resulting crystals were recrystalized from 95% aqueous alcohol to yield the title compound (413 mg).

m.p. 251–253° C.

Elemental Analysis for $C_{25}H_{30}N_6OCl_2$

Calculated (%): C, 59.88; H, 6.03; N, 16.76

Found (%): C, 59.76; H, 6.09; N, 16.80

EXAMPLE 2

Production of 6-[3-[4-(diphenylmethoxy)piperidino]propoxyl][1,2,4]triazolo[1,5-b]pyridazine fumaric acid salt 4-(Diphenylmethoxy)-1-Piperidinepropanol (390 mg) was dissolved in dried tetrahydrofuran (10 ml), followed by addition of sodium t-butoxide (127 mg). The mixture was refluxed under heating for 30 minutes. After the mixture was cooled, 6-chloro[1,2,4]triazolo[1,5-b]pyridazine (215 mg) was added thereto. The resulting mixture was refluxed for 3 hours under heating. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and dissolved in ethanol (10 ml). Fumaric acid (93 mg) was added to the solution to precipate crystals. The resulting crystals were recrystalized from ethanol to yield the title compound (218 mg).

m.p. 157–159° C.

Elemental Analysis for $C_{30}H_{33}N_5O_6$

Calculated (%): C, 64.39; H, 5.94; N, 12.51

Found (%): C, 64.16; H, 5.71; N, 12.32

EXAMPLE 3

Production of 6-[3-[4-(diphenylmethyl)piperazino]propoxy]-7-isopropyl[1,2,4]triazolo[1,5-b]pyridazine dihydrochloride 4-(Diphenylmethyl)-1-piperazinepropanol (466 mg) was dissolved in dried tetrahydrofuran (10 ml), followed by addition of sodium t-butoxide (173 mg). The mixture was refluxed under heating for 30 minutes. After the mixture was cooled, 6-chloro-7-isopropyl[1,2,4]triazolo[1,5-b]pyridazine (295 mg) was added thereto. The resulting mixture was refluxed for 3 hours under heating. After cooling, ice-water was added to the mixture, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (10:1). Fractions containing the objective compound were collected and dissolved in ethanol (10 ml), followed by addition of 1N-HCl (3 ml). The mixture was concentrated under reduced pressure. The resulting crystals were recrystalized from ethyl acetate to yield the title compound (582 mg).

m.p. 177° C.

Elemental Analysis for $C_{28}H_{36}N_6OCl_2$

Calculated (%): C, 59.89; H, 6.82; N, 14.97

Found (%) : C, 59.47; H, 6.89; N, 14.45

EXAMPLE 4

Production of 6-[3-[4-(diphenylmethoxy)piperidino]propoxyl]-7-isopropyl[1,2,4]triazolo[1,5-b]pyridazine fumaric acid salt 4-(Diphenylmethoxy)-1-piperidinepropanol (488 mg) was dissolved in dried tetrahydrofuran (10 ml), followed by addition of sodium t-butoxide (173 mg). The mixture was refluxed under heating for 30 minutes. After the mixture was cooled, 6-chloro-7-siopropyl[1,2,4]triazolo[1,5-b]pyridazine (295 mg) was added thereto. The resulting mixture was refluxed for 3 hours under heating. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and dissolved in ethanol (10 ml). Fumaric acid (98 mg) was added to the solution to precipitate crystals. The resulting crystals were recrystalized from ethyl acetate to yield the title compound (385 mg).

m.p. 163–165° C.

Elemental Analysis for $C_{33}H_{39}N_5O_6$

Calculated (%): C, 65.87; H, 6.53; N, 11.64

Found (%): C, 65.77; H, 6.46; N, 11.71

EXAMPLE 5

Production of 6-[3-[4-(diphenylmethyl)piperazino]propylamino][1,2,4]triazolo[1,5-b]pyridazine Process A 6-(3-Hydroxypropylamino) [1,2,4]triazolo[1,5-b]pyridazine 6-Chloro[1,2,4]triazolo[1,5-b]pyridazine (928 mg) was dissolved in ethanol (10 ml). 3-Amino-1-propanol (1.23 g) was added to the solution. The mixture was refluxed under heating for 20 hours. After being cooled, the mixture was concentrated under reduced pressure to an half of its volume. The resulting precipitates were washed with ethanol and dried to yield the title compound (835 mg).

m.p. 193–194° C.

Elemental Analysis for $C_8H_{11}N_5O$

Calculated (%): C, 49.73; H, 5.74; N, 36.25

Found (%): C, 49.70; H, 5.53; N, 36.28

Process B 6-(3-Hydroxypropylamino)[1,2,4]triazolo[1,5-b]pyridazine (450 mg) was suspended in tetrahydrofuran (15 ml).

N-Ethyldiisopropylamine (582 mg) and methanesulfonylchloride (533 mg) were added to the suspension. The resulting mixture was stirred at room temperature for one hour. Ice-water and sodium chloride were added to the mixture, followed by extraction with ethyl acetate. The extract was washed with an aqueous sodium chloride saturated solution, dried over magnesium sulfate and concentrated under reduced pressure. The residue was dissolved in N,N-dimethylformamide (10 ml), followed by addition of 1-(diphenylmethyl)piperazine (504 mg), sodium iodide (298 mg) and potassium carbonate (276 mg). The mixture was stirred at 60° C. for two hours. After the mixture was cooled, ice-water was added to the mixture, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (90:10:1). Fractions containing the objective compound were collected and concentrated. The resulting crystals were washed with ethyl ether and dried to yield the title compound (281 mg).

m.p. 139–140° C.

Elemental Analysis for $C_{25}H_{29}N_7.0.5H_2O$

Calculated (%): C, 68.78; H, 6.93; N, 22.46

Found (%): C, 68.72; H, 6.86; N, 22.16

EXAMPLE 6

Production of 6-[3-[4-(diphenylmethoxy)piperizine] propylamino][1,2,4]triazolo[1,5-b]pyridazine 6-(3-Hydroxypropylamino)[1,2,4]triazolo[1,5-b] pyridazine (290 mg) was suspended in tetrahydrofuran (10 ml). N-ethyldiisopropylamine (388 mg) and methanesulfonylchloride (344 mg) were added to the suspension, and the mixture was stirred at room temperature for one hour. Ice-water and sodium chloride were added to the mixture, followed by extraction with ethyl acetate. The extract was washed with an aqueous sodium chloride saturated solution, dried over magnesium sulfate and concentrated under reduced pressure. The residue was dissolved in N,N-dimethylformamide (5 ml), followed by addition of 4-(dipheylmethoxy)piperidine (352 mg), sodium iodide (208 mg) and potassium carbonate (193 mg). The mixture was stirred at room temperature for 15 hours and at 60° C. for 3 hours. After the mixture was cooled, ice-water was added thereto, followed by extraction with ethyl acetate. The extract was washed with an aqueous sodium chloride saturated solution, dried over magnesium chloride and concentrated under reduced pressure. The residue was subjected to silica gel column chromatography and eluted with a mixture of ethyl acetate, methanol and triethylamine (90:10:1). Fractions containing the objective compound were concentrated. The resulting crystals were washed with ethyl ether and dried to yield the captioned compound (209 mg).

m.p. 136–138° C.

Elemental Analysis for $C_{26}H_{30}N_6O$

Calculated (%): C, 70.56; H, 6.83; N, 18.99

Found (%): C, 70.43; H, 6.83; N, 19.04

EXAMPLE 7

Production of 6-[3-[4-(dipheylmethyl)piperazino]-propylthio][1,2,4]triazolo[1,5-b]pyridazine Process A 6-(3-Bromopropylthio)[1,2,4]triazolo[1,5-b]pyridazine Methyl 3-mercaptopropionate (3.9 ml) was dissolved in methanol (40 ml), followed by addition of a 2N sodium methoxide solution in methanol (15 ml) and 6-chloro[1,2,4]triazolo[1,5-b]pyridazine (1.55 g). The mixture was refluxed under heating for one hour. After being cooled, the mixture was concentrated under reduced pressure. Ethyl acetate was added to the residue. The resulting crystals were collected, washed with ethyl acetate and suspended in terahydrofuran (40 ml), followed by addition of 1,3-dibromopropane (3.06 ml). The mixture was refluxed under heating for two hours. After the mixture was cooled, ice-water was added thereto. The mixture was extracted with ethyl acetate. The extract was washed with an aqueous sodium chloride saturated solution, dried over magnesium sulfate and concentrated under reduced pressure. A mixed solvent of ethyl acetate-hexane (1:1) was added to the residue. The resulting crystals were collected and dried to yield the title compound (1.97 g).

m.p. 133–135° C.

Elemental Analysis for $C_8H_9N_4SBr$

Calculated (%): C, 35.18; H, 3.32; N, 20.51

Found (%): C, 35.11; H, 3.13; N, 20.43

Process B 6-(3-Bromopropylthio)[1,2,4]triazolo[1,5-b]pyridazine (546 mg) and 1-(diphenylmethyl)piperazine (505 mg) were dissolved in acetonitrile (15 ml), followed by addition of sodium iodide (373 mg) and potassium carbonate (277 mg). The mixture was stirred at 50–60° C. for 15 hours, followed by addition of ice-water and extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (95:5). Fractions containing the objective compound were collected and concentrated. The resulting crystals were collected, washed with ethyl ether and dried to yield the title compound (507 mg).

m.p. 128–130° C.

Elemental Analysis for $C_{25}H_{28}N_6S$

Calculated (%): C, 67.54; H, 6.35; N, 18.90

Found (%): C, 67.25; H, 6.29; N, 18.78

EXAMPLE 8

Production of 6-[3-[4-(diphenylmethoxy)piperidino] propylthio][1,2,4]triazolo[1,5-b]pyridazine fumaric acid salt 6-(3-Bromopropylthio)[1,2,4]triazolo[1,5-b]pyridazine (546 mg) and 4-(diphenylmethoxy)piperidine (535 mg) were dissolved in acetonitrile (15 ml), followed by addition of sodium iodide (373 mg) and potassium carbonate (277 mg). The mixture was stirred at 50–60° C. for 15 hours, followed by addition of ice-water after cooled and extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and concentrated. The residue was dissolved in ethanol (20 ml), followed by addition of fumaric acid (159 mg). The resulting crystals were collected, washed with ethyl ether and dried to yield the title compound (435 mg).

m.p. 185–187° C.

Elemental Analysis for $C_{30}H_{33}N_5O_5S.0.5H_2O$

Calculated (%): C, 61.63; H, 5.86; N, 11.98

Found (%): C, 61.98; H, 5.83; N, 11.95

EXAMPLE 9

Production of 6-[3-[4-(diphenylmethyl)piperazino] propylthio]-7-isopropyl[1,2,4]triazolo[1,5-b] pyridazine Process A 6-(3-Chloropropylthio)-7-isopropyl[1,2,4]triazolo[1,5-b]pyridazine Methyl 3-mercaptopropionate (3.9 ml) was dissolved in methanol (40 ml), followed by addition of 2N sodium methoxide in methanol solution (15 ml) and 6-chloro-7-isopropyl[1,2,4]triazolo[1,5-b]pyridazine (1.97 g). The mixture was refluxed under heating for 40 minutes. After being cooled, the mixture was concentrated under reduced pressure. Ethyl acetate was added to the residue. The resulting crystals were collected, washed with ethyl acetate and suspended in tetrahydrofuran (40 ml), followed by addition of 1-bromo-3-chloropropane (2 ml). The mixture was refluxed under heating for two hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of hexane and ethyl acetate (2:3). Fractions containing the objective compound were pooled and concentrated under reduced pressure. The resulting crystals were collected and dried to yield the title compound (2.39 g).

m.p. 82–83° C.

Elemental Analysis for $C_{11}H_{15}N_4SCl$

Calculated (%): C, 48.79; H, 5.58; N, 20.69

Found (%): C, 48.79; H, 5.53; N, 20.87

Process B 6-(3-Chloropropyllthio)-7-isopropyl[1,2,4]triazole [1,5-b]pyridazine (542 mg) and 1-(diphenylmethyl)piperazine (555 mg) were dissolved in acetonitrile (15 ml), followed by addition of sodium iodide (447 mg) and potassium carbonate (277 mg). The mixture was refluxed under heating for 20 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica-gel column chromatography, followed by extraction with ethyl acetate. Fractions containing the objective compound were collected and concentrated. The resulting crystals were recrystalized from a mixture of ethyl acetate and ethyl ether (1:1) and dried to yield the captioned compound (607 mg).

m.p. 137–139° C.

Elemental Analysis for $C_{28}H_{34}N_6S$

Calculated (%): C, 69.10; H, 7.04; N, 17.27

Found (%): C, 69.04; H, 7.06; N, 17.33

EXAMPLE 10

Production of 6-[3-[4-(diphenylmethoxy)piperidino] propylthio]-7-isopropyl[1,2,4]triazolo[1,5-b] pyridazine fumaric acid salt 6-(3-Chlolopropylthio)-7-isopropyl[1,2,4]triazolo[1,5-b]pyridazine (542 mg) and 4-(diphenylmethoxy)piperidine (535 mg) were dissolved in acetonitrile (15 ml), followed by addition of sodium iodie (447 mg) and potassium carbonate (277 mg). The mixture was refluxed under heating for 15 hours. After the mixture as cooled, ice-water was added thereto, followed by extraction with ethyl acetate. The extract was washed with an aqueous sodium chloride saturated solution, dried over magnesium sulfate and concentrated under reduced pressure. The residue was subjected to silica-gel column chromatography, followed by elution with a mixture of ethyl acetate and methanol (95:5). Fractions containing the objective compound were collected and concentrated. The residue was dissolved in ethanol (20 ml), followed by addition of fumaric acid (196 mg). The resulting crystals were collected, washed with ethanol and dried to yield the title compound (780 mg).

m.p. 164–165° C.

Elemental Analysis for $C_{33}H_{39}N_5O_5S$

Calculated (%): C, 64.16; H, 6.36; N, 11.34

Found (%): C, 64.45; H, 6.49; N, 11.67

EXAMPLE 11

Production of 6-[4-(diphenylmethoxy)piperidino][1,2,4]triazolo[1,5-b]pyridazine 4-(Diphenynylmethoxy)piperidine (1.12 g) and 6-chloro [1,2,4]triazolo[1,5-b]pyridazine (558 mg) were dissolved in n-butanol (25 ml), followed by addition of N-ethyldiisopropylamine (700 mg). The mixture was refluxed under heating for 17 hours. After being cooled, the mixture was concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of hexane and ethyl acetate (1:3). Fractions containing the objective compound were collected and recrystalized from ethanol to yield the captioned compound (757 mg).

m.p. 137–139° C.

Elemental Analysis for $C_{23}H_{23}N_5O$

Calculated (%): C, 71.67; H, 6.01; N, 18.17

Found (%): C, 71.75; H, 5.90; N, 18.34

EXAMPLE 12

Production of 6-[4-[4-(diphenylmethoxy)piperidino] butylamino][1,2,4]triazolo[1,5-b]pyridazine 4-(Diphenylmethoxy)-1-piperidinebutanamine (1.83 g) and 6-chloro[1,2,4]triazolo[1,5-b]pyridazine (557 mg) were dissolved in n-butanol (30 ml), followed by addition of N-ethyldiisopropylamine (931 mg). The mixture was refluxed under heating for 14 hours. After being cooled, the mixture was concentrated under reduced pressure, followed by addition of ice-water and extraction with ethyl acetate. The extract was washed with an aqueous sodium chloride saturated solution, dried over sodium sulfate and concentrated under reduced pressure. The residue was subjected to a silica-gel column chromatography and eluted with a mixture of ethyl acetate, methanol and triethylamine (45:5:1). Fractions containing the objective compound were collected and concentrated. The resulting crystals were collected, washed with ethylether and dried to yield the title compound (149 mg).

m.p. 102–104° C.

Elemental Analysis for $C_{27}H_{32}N_6O$

Calculated (%): C, 71.03; H, 7.06; N, 18.41

Found (%): C, 70.78; H, 6.77; N, 18.40

EXAMPLE 13

Production of 6-[2-[4-(diphenylmethoxy)piperidino]ethylamino][1,2,4]triazolo[1,5-b]pyridazine Process A Production of 6-(2-hydroxyethylamino)[1,2,4]triazolo[1,5-b]pyridazine 2-Aminoethanol (2.01 g) and 6-chloro[1,2,4]triazolo[1,5-b]pyridazine (2.03 g) were dissolved in ethanol (22 ml). The mixture was refluxed under heating for 20 hours. After being cooled, the mixture was concentrated under reduced pressure. The resulting crystals were collected and dried to yield the title compound (1.48 g).

m.p. 219–221° C.

Elemental Analysis for $C_7H_9N_5O$

Calculated (%): C, 46.92; H, 5.06; N, 39.09

Found (%): C, 46.67; H, 5.00; N, 38.93

Process B 6-(2-Hydroxyethylamino)[1,2,4]triazolo[1,5-b]pyridazine (1.25 g) was suspended in tetrahyfrofurane (40 ml), followed by addition of N-ethyldiisopropylamine (1.81 g) and methanesulfonylchloride (1.60 g). The mixture was stirred at room temperature for 45 minutes, followed by addition of ice-water and sodium chloride to be saturated therewith. The mixture was extracted with ethyl acetate. The extract was washed with an aqueous sodium chloride saturated solution, dried over magnesium sulfate and concentrated under reduced pressure. The residue was dissolved in N,N-dimethylformamide (21 ml), followed by addition of 4-(diphenylmethoxy)piperidine (1.79 g), sodium iodide (1.00 g) and potassium carbonate (927 mg). The mixture was stirred at room temperature for 15 hours and at 60° C. for 1.5 hours, followed by addition of ice-water and extraction with ethyl ether. The extract was washed with an aqueous sodium chloride saturated solution dried over magnesium sulfate and concentrated under reduced pressure. The resulting crystals were collected, washed with ethyl ether and dried to yield the title compound (1.13 g).

m.p. 152–154° C.

Elemental Analysis for $C_{25}H_{28}N_6O$

Calculated (%): C, 70.07; H, 6.59; N, 19.61

Found (%): C, 69.66; H, 6.40; N, 20.03

EXAMPLE 14

Production of 6-[2-[4-(diphenylmethoxy)piperidino]ethoxy][1,2,4]triazolo[1,5-b]pyridazine fumaric acid salt 4-(Diphenylmethoxy)-1-piperidineethanol (774 mg) was dissolved in dried tetrahydrofurane (20 ml), followed by addition of sodium t-butoxide (263 mg). The mixture was refluxed under heating for 30 minutes. After the mixture was cooled, 6-chloro[1,2,4]triazolo[1,5-b]pyridazine (385 mg) was added thereto. The mixture was refluxed under heating for 6 hours. After the mixture was cooled, ice-water was added to the mixture, followed by extraction with ethyl acetate. The extract was washed with an aqueous sodium chloride saturated solution, dried over magnesium sulfate and concentrated under reduced pressure. The residue was subjected silica-gel column chromatography and eluted with a mixture of ethyl acetate and methanol (10:1). Fractions containing the objective compound were collected, dissolved in ethanol and solidified with the addition of fumaric acid (216 mg). The resulting crystals were recrystalized from ethanol to yield the title compound (420 mg).

m.p. 176–177° C.

Elemental Analysis for $C_{29}H_{31}N_5O_6 \cdot H_2O$

Calculated (%): C, 61.80; H, 5.90; N, 12.43

Found (%): C, 61.72; H, 5.65; N, 12.03

EXAMPLE 15

Production of 7-t-butyl-6-[2-[4-(diphenylmethoxy)piperidino]ethoxy][1,2,4]triazolo[1,5-b]pyridazine 4-(Diphenylmethoxy)-1-piperidineethanol (740 mg) was dissolved in dried tetrahydrofurane (18 ml), followed by addition of sodium t-butoxide (251 mg). The mixture was refluxed under heating for 25 minutes. After the mixture was cooled, 7-tert-butyl-6-chloro[1,2,4]triazolo[1,5-b]pyridazine (501 mg) was added thereto. The mixture was refluxed under heating for 2 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica-gel column chromatography and eluted with ethyl acetate. Fractions containing the objective compound were collected and recrystalized from ethyl acetate to yield the title compound (380 mg).

m.p. 133–135° C.

Elemental Analysis for $C_{29}H_{35}N_5O_2$

Calculated (%): C, 71.73; H, 7.26; N, 14.42

Found (%): C, 71.47; H, 7.06; N, 14.19

EXAMPLE 16

Production of 6-[3-[4-(diphenylmethoxy)piperidino]-2-hydroxypropoxy][1,2,4]triazolo[1,5-b]pyridazine Process A Production of 6-(oxirane-2-methoxy)[1,2,4]triazolo[1,5-b]pyridazine Glycidol (0.13 ml) and 6-chloro[1,2,4]triazolo[1,5-b]pyridazine (309 mg) were suspended in N,N-dimethylformamide (5 ml), followed by addition of 60% oily sodium hydride (8 mg) at room temperature. The mixture was stirred for 3 hours, followed by addition of an aqueous sodium chloride solution and extraction with ethyl acetate. The extract was dried over magnesium sulfate and concentrated under reduced pressure. The residue was subjected to silica-gel column chromatography and eluted with ethyl acetate. Fractions containing the objective compound were collected and dried to give the title compound (170 mg).

$^1$H-NMR (CDCl$_3$) δ ppm: 2.7–2.9(1H,m), 2.9–3.1(1H,m), 3.3–3.4(1H,m), 4.1–4.4(1H,m), 4.7–4.9(1H,m), 7.11(1H,d, J=9 Hz), 8.02(1H,d,J=9 Hz), 8.34(1H,s).

Process B 6-(Oxirane-2-methoxy)[1,2,4]triazolo[1,5-b]pyridazine (171 mg) and 4-(diphenylmethoxy)piperidine (238 mg) were suspended in ethanol (8 ml). The suspension was stirred at 60° C. for 5 hours and concentrated under reduced pressure. Ethyl acetate was added to the residue. The resulting crystals were collected, washed with ethyl ether and dried to yield the title compound (327 mg).

m.p. 133–135° C.

Elemental Analysis for $C_{26}H_{29}N_5O_3$

Calculated (%): C, 67.96; H, 6.36; N, 15.24

Found (%): C, 67.84; H, 6.13; N, 15.34

EXAMPLE 17

Production of 6-[3-[4-(diphenylmethyl)piperazino]-2-hydroxypropoxy][1,2,4]triazolo[1,5-b]pyridazine dihydrochloride 6-(Oxirane-2-methoxy)[1,2,4]triazolo[1,5-b]pyridazine (485 mg) and 1-(diphenylmethyl)piperazine (764 mg) were suspended in ethanol (30 ml). The mixture was stirred at 60° C. for 15 hours and concentrated under reduced pressure. Ethyl acetate was added to the residue. The resulting crystals were collected, washed with diethyl ether and dissolved in ethyl acetate (20 ml). 4N HCl-ethyl acetate solution (5 ml) was added thereto, followed by concentration under reduced pressure. The resulting crystals were recrystalized from ethanol to yield the captioned compound (392 mg).

m.p. 242° C. (decomp.)

Elemental Analysis for $C_{25}H_{30}N_6O_2Cl_2 \cdot H_2O$

Calculated (%): C, 56.08; H, 6.02; N, 15.69

Found (%): C, 56.44; H, 6.03; N, 15.84

EXAMPLE 18

Production of 6-[3-[4-(diphenylmethoxy)piperidino]propionamido][1,2,4]triazolo[1,5-b]pyridazine Process A 6-(3-Chloropropionamido)[1,2,4]triazolo[1,5-b]pyridazine 6-Amino[1,2,4]triazolo[1,5-b]pyridazine (0.80 g) was dissolved in N,N-dimethylacetamide (7 ml), followed by addition of 3-chloropropionylchloride (0.68 ml) under ice-cooling. The mixture was stirred at room temperature for 1 hour and poured into ice-water, followed by extraction with a mixture of ethyl acetate and tetrahydrofuran (1:1). The extract was washed with an aqueous sodium chloride saturated solution, dried over magnesium sulfate and concentrated under reduced pressure. Ethyl ether was added to the residue. The resulting crystals were collected by filtration and dried to yield the title compound (0.875 g).

$^1$H-NMR (d$_6$-DMSO) δ ppm: 2.99(2H,t,J=7 Hz), 3.91 (2H,t,J=7 Hz), 8.36, 8.43 (each 1H,d,J=10 Hz), 8.57 (1H,s), 11.37(1H,s).

Process B 6-(3-Chloropropionamido)[1,2,4]triazolo[1,5-b]pyridazine (339 mg) and 4-(diphenylmethoxy)piperizine (401 mg) were dissolved in acetonitrile (15 ml), followed by addition of sodium iodide (447 mg) and potassium carbonate (249 mg). The mixture was stirred at room temperature for 15 hours, followed by addition of ice-water and extraction with ethyl acetate. The extract was washed with an aqueous sodium chloride saturated solution, dried over magnesium sulfate and concentrated under reduced pressure. The residue was subjected to a silica-gel column chromatography and eluted with a mixture of ethyl acetate and methanol (85:15). Fractions containing the objective compound were collected and concentrated. The resulting crystals were recrystalized from ethanol to yield the title compound (495 mg).

m.p. 176–177° C.

Elemental Analysis for $C_{26}H_{28}N_6O_2$

Calculated (%): C, 68.40; H, 6.18; N, 18.41

Found (%): C, 68.20; H, 6.00; N, 18.36

EXAMPLE 19

Production of 6-[3-[4-(diphenylmethyl)piperazino]propionamido][1,2,4]triazolo[1,5-b]pyridazine 6-(3-Chloropropionamido)[1,2,4]triazolo[1,5-b]pyridazine (339 mg) and 1-(diphenylmethyl)piperazine (379 mg) were dissolved in acetonitrile (15 ml), followed by addition of sodium iodide (447 mg) and potassium carbonate (249 mg). The mixture was stirred at room temperature for 15 hours and refluxed under heating for 8 hours. After the mixture was cooled, ice-water was added thereto, followed by extraction with ethyl acetate. The extract was washed with an aqueous sodium chloride saturated solution, dried over magnesium sulfate and concentrated under reduced pressure. The resulting crystals were recrystalized from ethanol to yield the title compound (408 mg).

m.p. 176–177° C.

Elemental Analysis for $C_{25}H_{27}N_7O$

Calculated (%): C, 66.65; H, 6.26; N, 21.76

Found (%): C, 66.36; H, 6.16; N, 21.95

EXAMPLE 20

Production of 6-[3-[4-(diphenylmethoxy)piperidino]propylamino]-2-methyl[1,2,4]triazolo[1,5-b]pyridazine 6-Chloro-2-methyl[1,2,4]triazolo[1,5-b]pyridazine (655 mg) and 4-(diphenylmethoxy)-1-piperidinepropanamine (1.26 g) was suspended in n-butanol (20 ml), followed by addition of N-ethyldiisopropylamine (1.94 ml). The mixture was refluxed under heating for 22 hours, followed by addition of ice-water and sodium hydrogen carbonate and extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate, methanol and triethylamine (50:5:1). Fractions containing the objective compound were collected and concentrated. The resulting crystals were washed with hexane and dried to yield the title compound (547 mg).

m.p. 119–120° C.

Elemental Analysis for $C_{27}H_{32}N_6O$

Calculated (%): C, 71.03; H, 7.06; N, 18.41

Found (%): C, 70.91; H, 6.95; N, 18.18

EXAMPLE 21

Production of 6-[3-[4-(diphenylmethoxy)piperidino]propoxy]-2-methyl[1,2,4]triazolo[1,5-b]pyridazine 4-(Diphenylmethoxy)-1-piperidinepropanol (743 mg) was dissolved in dried terahydrofuran (17 ml), followed by addition of sodium t-butoxide (241 mg). The mixture was heated to 60° C. and stirred for 30 minutes. After the mixture was cooled, 6-chloro-2-methyl[1,2,4]triazolo[1,5-b]pyridazine (384 mg) was added thereto, followed by reflux under heating for 21 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate, methanol and triethylamine (50:5:1). Fractions containing the objective compound were collected. The resulting crystals were washed with ethylether and dried to yield the title compound (700 mg).

m.p. 134–136° C.

Elemental Analysis for. $C_{27}H_{31}N_5O_2$

Calculated (%): C, 70.87; H, 6.83; N, 15.31
Found (%): C, 70.67; H, 6.94; N, 15.34

EXAMPLE 22

Production of 6-[4-[4-(diphenylmethoxy)piperidino]butoxy][1,2,4]triazolo[1,5-b]pyridazine fumaric acid salt 4-(Diphenylmethoxy)-1-piperidinebutanol (2.04 g) was dissolved in dried tetrahydrofuran (60 ml), followed by addition of 60% oily sodium hydride (480 mg). The mixture was refluxed under heating for 70 minutes. After the mixture was cooled, 6-chloro[1,2,4]triazolo[1,5-b]pyridazine (927 mg) and N,N-dimethylformamide (30 ml) were added thereto, followed by reflux under heating for 18 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate, methanol and triethylamine (50:5:1). The fractions containing the objective compound were collected. The obtained oily mixture was dissolved in ethanol, followed by addition of fumaric acid (80 mg). This mixture was concentrated under reduced pressure, and the residue was recrystalized from methanol to yield the title compound (266 mg).

m.p. 159–161° C.

Elemental Analysis for $C_{31}H_{35}N_5O_6$

Calculated (%): C, 64.91; H, 6.15; N, 12.21

Found (%): C, 64.72; H, 6.10; N, 12.06

EXAMPLE 23

Production of 6-[2-[4-(diphenylmethoxy)piperidino]acetamido][1,2,4]triazolo[1,5-b]pyridazine Process A 6-(2-Bromoacetamido)[1,2,4]triazolo[1,5-b]pyridazine (1.32 g) was dissolved in N,N-dimethylacetamide (12 ml), followed by addition of bromoacetylbromide under ice-cooling (1.02 ml). The mixture was stirred at room temperature for 30 minutes and poured into ice-water. The resulting crystals were washed with water and ethyl acetate and dried to yield the title compound (2.37 g).

m.p. 210° C. (decomp.)

Elemental Analysis for $C_7H_6N_5OBr$

Calculated (%): C, 32.83; H, 2.36; N, 27.35

Found (%): C, 33.04; H, 2.50; N, 26.84

Process B 6-(2-Bromoacetamido)[1,2,4]triazolo[1,5-b]pyridazine (605 mg) and 4-(diphenylmethoxy)piperidine (632 mg) were dissolved in acetonitrile (20 ml), followed by addition of potassium carbonate (391 mg). The mixture was stirred at room temperature for 3 hours, followed by addition of ice-water and extraction with ethyl acetate. The extract was washed with an aqueous sodium chloride saturated solution, dried over magnesium sulfate and concentrated under reduced pressure. The resulting crystals were collected, recrystalized from ethanol and dried to yield the title compound (769 mg).

m.p. 158–160° C.

Elemental Analysis for $C_{26}H_{26}N_6O_2$

Calculated (%): C, 67.86; H, 5.92; N, 18.99

Found (%): C, 67.59; H, 5.91; N, 18.76

EXAMPLE 24

Production of 6-[2-[4-(diphenylmethyl)piperazino]acetamido][1,2,4]triazolo[1,5-b]pyridazine 6-(2-Bromoacetamido)[1,2,4]triazolo[1,5-b]pyridazine (636 mg) and 1-(diphenylmethyl)piperazine (627 mg) were dissolved in acetonitrile (20 ml), followed by addition of potassium carbonate (411 mg). The mixture was stirred at room temperature for 2 hours, followed by addition of ice-water and extraction with ethyl acetate. The extract was washed with aqueous sodium chloride saturated solution, dried over magnesium sulfate and concentrated under reduced pressure. The resulting crystals were collected by filtration and recrystalized from methanol to yield the captioned compound (525 mg).

m.p. 203–204° C.

Elemental Analysis for $C_{24}H_{25}N_7O$

Calculated (%): C, 67.43; H, 5.89; N, 22.93

Found (%): C, 67.22; H, 5.87; N, 22.97

EXAMPLE 25

Production of 6-[2-[4-(diphenylmethoxy)piperizinocarbonyloxyethoxy][1,2,4]triazolo[1,5-b]pyridazine Process A 6-(2-Hydroxyethoxy)[1,2,4]triazolo[1,5-b]pyridazine 60% Oily sodium hydride (510 mg) was suspended in N,N-dimethylformamide (70 ml), followed by addition of 2-(t-butyldiphenysilyoxy)ethanol (3.83 g). The mixture was stirred at room temperature for 1 hour, followed by addition of 6-chloro[1,2,4]triazolo[1,5-b]pyridazine (1.98 g). The mixture was stirred at room temperature for 5 hours and poured into ice-water, followed by extraction with ethylether. The extract was washed with an aqueous sodium chloride solution, dried over magnesium sulfate and concentrated under reduced pressure. The residue was dissolved in tetrahydrofuran (40 ml), followed by addition of tetra-n-butylammoniumfluoride trihydrate (2.02 g). The mixture was stirred at room temperature for 10 minutes and concentrated under reduced pressure. The residue was subjected to silica-gel column chromatography and eluted with a mixture of ethyl acetate and hexane (1:1). Fractions containing the objective compound were collected and concentrated to yield the title compound (0.875 g).

$^1$H-NMR (CDCl$_3$) δ ppm: 4.06(2H,t,J=5 Hz), 4.5–4.7(2H, m), 7.10,8.01(each 1H,d,J=10 Hz), 8.34(1H,s).

Process B 6-(2-Hydroxyethoxy)[1,2,4]triazolo[1,5-b]pyridazine (275 mg) was dissolved in tetrahydrofuran (12 ml), followed by addition of carbonyldiimidazole (544 mg). The mixture was stirred at room temperature for 3 hours, followed by addition of 4-(diphenylmethoxy)piperidine (900 mg) and N-ethyldiisopropylamine (0.53 ml). The mixture was further stirred at room temperature for 13 hours and concentrated under reduced pressure. The residue was subjected to silica-gel column chromatography and eluted with ethyl acetate. Fractions containing the objective compound were collected and concentrated to yield the title compound (490 mg).

m.p. 75–76° C.

Elemental Analysis for $C_{26}H_{27}N_5O_4$

Calculated (%): C, 65.95; H, 5.75; N, 14.79

Found (%): C, 65.88; H, 5.84; N, 14.88

EXAMPLE 26

Production of 6-[2-[4-(diphenylmethyl)piperazinocarbonyloxy]ethoxy][1,2,4]triazolo[1,5-b]pyridazine 6-(2-Hydroxyethoxy)[1,2,4]triazolo[1,5-b]pyridazine (450 mg) was dissolved in tetrahydrofuran (20 ml), followed by addition of carbonyldiimidazole (649 mg). The mixture was stirred at room temperature for 3 hours, followed by addition of 1-(diphenylmethyl)piperazine (1.07 g) and N-ethyldiisopropylamine (0.73 ml). The mixture was stirred at 60° C. for 17 hours and concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate and hexane (1:1). Fractions containing the objective compound were collected and concentrated. The resulting crystals were recrystalized from ethyl acetate to yield the title compound (464 mg).

m.p. 157–159° C.
Elemental Analysis for $C_{25}H_{26}N_6O_3 \cdot 0.5H_2O$
Calculated (%): C, 64.23; H, 5.82; N, 17.98
Found (%): C, 64.32; H, 5.50; N, 17.56

EXAMPLE 27

Production of 6-[3-[4-(diphenylmethoxy)piperidino-carbonyloxy]propoxy][1,2,4]triazolo[1,5-b]pyridazine Process A 1-[(3-t-butyldiphenylsilyloxy)propoxycarbonyl]-4-(diphenylmethoxy)piperidine 3-(t-butyldiphenylsilyloxy)propanol (2.12 g) was dissolved in tetrahydrofuran (20 ml), followed by addition of carbonyldiimidazole (1.20 g). The mixture was stirred at room temperature for 20 minutes, followed by addition of 4-(diphenylmethoxy)piperidine (1.98 g) and N-ethyldiisopropylamine (1.28 ml). The mixture was stirred at room temperature for 23 hours and concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate and hexane (1:10). Fractions containing the objective compound were collected and concentrated to yield the title compound (3.95 g).

$^1$H-NMR (CDCl$_3$) δ ppm: 1.04(9H,s), 3.73(2H,t,J=7 Hz), 4.21(2H,t,J=7 Hz), 5.51(1H,s), 7.2–7.8(20H,m).

Process B

Production of 4-(diphenylmethoxy)-1-[(3-hydroxypropoxy)carbonyl]piperidine

1-[(3-t-butyldiphenylsilyloxy)propoxycarbonyl]-4-diphenylmethoxypiperidine (1.95 g) was dissolved in tetrahydrofuran (15 ml), followed by addition of tetra-n-butylammoniumfluoride trihydride (2.02 g). The mixture was stirred at room temperature for 3 hours and concentrated under reduced pressure. The residue was subjected to silica-gel column chromatography and eluted with ethyl acetate. Fractions containing the objective compound were collected and concentrated to yield the title compound (1.33 g).

$^1$H-NMR (CDCl$_3$) δ ppm: 1.5–2.0(6H,m), 3.1–3.4(2H,m), 3.5–3.9(5H,m), 4.26(2H,t,J=6 Hz), 5.52(1H,s), 7.1–7.5 (10H,m).

Process C 4-(Diphenylmethoxy)-1-(3-hydroxypropoxycarbonyl) piperidine (1.33 g) was dissolved in tetrahydrofuran (30 ml), followed by addition of sodium t-butoxide (339 mg). The mixture was stirred at 60° C. for 1.5 hours. After the mixture was cooled, 6-chloro[1,2,4]triazolo[1,5-b]pyridazine (496 mg) was added thereto. The mixture was refluxed under heating for two hours, followed by addition of ice-water and extraction with ethyl acetate. The extract was washed with an aqueous sodium chloride solution, dried over magnesium sulfate and concentrated under reduced pressure. The residue was subjected to silica-gel column chromatography and eluted with ethyl acetate. Fractions containing the objective compound were collected and concentrated to yield the title compound (0.730 g).

m.p. 119–120° C.
Elemental Analysis for $C_{27}H_{29}N_5O_4$
Calculated (%): C, 66.51; H, 6.00; N, 14.36
Found (%): C, 66.65; H, 5.78; N, 14.64

EXAMPLE 28

Production of 6-[3-[4-(diphenylmethyl)piperazino-carbonyloxy]propoxy][1,2,4]triazolo[1,5-b]pyridazine hydrochloride Process A Production of 1-[3-(t-butyldiphenylsilyloxy)propoxycarbonyl]-4-(diphenylmethyl)piperazine 3-(t-butyldiphenylsilyloxy)propanol (1.71 g) was dissolved in tetrahydrofuran (16 ml), followed by addition of carbonyldiimidazole (0.97 g). The mixture was stirred at room temperature for 20 minutes, followed by addition of 1-(diphenylmethyl)piperazine (1.51 g) and N-ethyldiisopropylamine (1.03 ml). The mixture was stirred at 60° C. for 16 hours. After being cooled, the mixture was concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica-gel column chromatography and eluted with a mixture of ethyl acetate and hexane (1:10). Fractions containing the objective compound were collected and concentrated to yield the title compound (2.53 g).

$^1$H-NMR (CDCl$_3$) δ ppm: 1.03(9H,s), 1.7–2.0(2H,m), 2.2–3.6(8H,m), 3.71(2H,t,J=6 Hz), 4.21(2H,t,J=6 Hz), 4.21 (1H,s), 7.1–7.7(20H,m).

Process B

Production of 4-(diphenymethyl)-1-(3-hydroxypropoxy) carbonyl)piperazine

1-[3-(t-butyldiphenylsilyloxy)propoxycarbonyl]-1-(diphenylmethyl)piperazine (2.50 g) was dissolved in tetrahydrofuran (12 ml), followed by addition of tetra-n-butylammoniumfluoride trihydrate (1.46 g). The mixture was stirred at room temperature for 3 hours and concentrated under reduced pressure. The residue was subjected to silica-gel column chromatography and eluted with a mixture of ethyl acetate and hexane (1:1). Fractions containing the objective compound were collected and concentrated to yield the title compound (1.51 g).

$^1$H-NMR (CDCl$_3$) δ ppm: 1.7–2.0(6H,m), 2.2–3.6(8H,m), 3.64(2H,t,J=6 Hz), 4.25(2H,t,J=6 Hz), 4.24(1H,s), 7.1–7.5 (10H,m).

Process C:

4-(Diphenylmethyl)-1-[(3-hydroxypropoxy)carbonyl] piperazine (1.44 g) was dissolved in tetrahydrofuran (30 ml), followed by addition of sodium t-butoxide (429 mg). The mixture was stirred at 60° C. for 0.5 hour. After the mixture was cooled, 6-chloro[1,2,4]triazolo[1,5-b]pyridazine (627 mg) was added thereto. This mixture was refluxed under heating for three hours, followed by addition of ice-water and extraction with ethyl acetate. The extract was washed with an aqueous sodium chloride solution, dried over magnesium sulfate and concentrated under reduced pressure. The residue was subjected to silica-gel column chromatography and eluted with a mixture of ethyl acetate and hexane (3:1). Fractions containing the objective compound were collected and concentrated. The residue was dissolved in ethyl acetate (10 ml), followed by addition of an ethyl acetate solution of 4N HCl (0.32 ml). The mixture was concentrated under reduced pressure. The resulting crystals were recrystalized from ethanol to yield the title compound (0.450 g).

m.p. 167–169° C.

Elemental Analysis for $C_{26}H_{29}N_6O_3Cl.0.5H_2O$

Calculated (%): C, 60.29; H, 5.84; N, 16.22

Found (%): C, 60.52; H, 5.96; N, 16.05

EXAMPLE 29

Production of 6-[6-[4-(diphenylmethoxy)piperidino] hexyloxy][1,2,4]triazolo[1,5-b]pyridazine fumaric acid salt 4-(Diphenylmethoxy)-1-piperidinehexanol (0.905 g) was dissolved in tetrahydrofuran (15 ml), followed by addition of 60% oily sodium hydride (118 mg). The mixture was refluxed under heating for 1 hour. After the mixture was cooled, 6-chloro[1,2,4]triazolo[1,5-b]pyridazine (381 mg) was added thereto. This mixture was refluxed under heating for 3 hours, followed by addition of ice-water and extraction with ethyl acetate. The extract was washed with an aqueous sodium chloride solution, dried over magnesium sulfate and concentrated under reduced pressure. The residue was subjected to silica-gel column chromatography and eluted with a mixture of ethyl acetate, methanol and triethylamine (50:5:1). Fractions containing the objective compound were collected and concentrated. The residue was dissolved in ethyl acetate (10 ml), followed by addition of a solution of fumaric acid (263 mg) in methanol (10 ml). The mixture was concentrated, and the residue was recrystalized from ethyl acetate to yield the title compound (0.979 g).

m.p. 136–138° C.

Elemental Analysis for $C_{33}H_{39}N_5O_6$

Calculated (%): C, 65.87; H, 6.53; N, 11.64

Found (%): C, 65.79; H, 6.54; N, 11.62

EXAMPLE 30

6-[6-[4-(diphenylmethyl)piperazino]hexyloxy][1,2,4]triazolo[1,5-b]pyridazine fumaric acid salt 4-(Diphenylmethyl)-1-piperazinehexanol (0.640 g) was dissolved in tetrahydrofuran (10 ml), followed by addition of 60% oily sodium hydride (145 mg). The mixture was refluxed under heating for 1 hour. After the mixture was cooled, 6-chloro[1,2,4]triazolo[1,5-b]pyridazine (281 mg) was added thereto. This mixture was refluxed under heating for 1.5 hours. Ice-water was added to the mixture, followed by extraction with ethyl acetate. The extract was washed with an aqueous sodium chloride solution, dried over magnesium sulfate and concentrated under reduced pressure. The residue was subjected to silica-gel column chromatography and eluted with ethyl acetate. Fractions containing the objective compound were collected and dissolved in ethyl acetate (10 ml), followed by addition of a solution of fumaric acid (140 mg) in methanol (10 ml). The mixture was concentration, and the residue was recrystalized from ethanol to yield the title compound (189 mg).

m.p. 149–151° C.

Elemental Analysis for $C_{32}H_{38}N_6O_5.0.5H_2O$

Calculated (%): C, 64.52; H, 6.60; N, 14.11

Found (%): C, 64.95; H, 6.64; N, 13.91

EXAMPLE 31

Production of 6-[3-[4-(diphenylmethoxy)piperidino] propoxy]-2-phenyl[1,2,4]triazolo[1,5-b]pyridazine hydrochloride 4-(Diphenylmethoxy)-1-piperidinepropanol (487 mg) was dissolved in dried tetrahydrofuran (10 ml), followed by addition of sodium t-butoxide (144 mg). The mixture was refluxed under heating for 40 minutes. After the mixture was cooled, 6-chloro-2-phenyl[1,2,4]triazolo[1,5-b]pyridazine (315 mg) was added thereto. This mixture was refluxed under heating for 4 hours. After the mixture was cooled, ice-water was added thereto, followed by extraction with a mixture of ethyl acetate and tetrahydrofuran (2:1). The extract was washed with an aqueous sodium chloride saturated solution dried over magnesium sulfate and concentrated under reduced pressure. The residue was subjected to silica-gel column chromatography and eluted with a mixture of ethyl acetate and methanol (10:1). Fractions containing the objective compound were collected, concentrated and dissolved in ethyl acetate (10 ml), followed by addition of 4N HCl in ethyl acetate solution (0.25 ml) and concentrated under reduced pressure. The resulting crystals were recrystalized from ethanol to yield the title compound (0.334 g).

m.p. 127–129° C.

Elemental Analysis for $C_{32}H_{34}N_5O_2Cl.H_2O$

Calculated (%): C, 66.95; H, 6.32; N, 12.20

Found (%): C, 67.01; H, 6.46; N, 12.27

EXAMPLE 32

Production of 6-[3-[4-(diphenylmethoxy)piperidino] propylamino]-2-phenyl[1,2,4]triazolo[1,5-b] pyridazine 365 mg of 6-chloro-2-phenyl[1,2,4]triazolo[1,5-b] pyridazine and 0.513 g of 4-(diphenylmethoxy)-1-piperidinepropanamine were suspended in 8 ml of n-butanol; 0.54 ml of N-ethyldiisopropylamine was added, followed by heating and refluxing for 19 hours. Ice water and sodium hydrogen carbonate were added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the resulting crystal was recrystallized from ethyl acetate to yield 308 mg of the title compound.

Melting point ; 170–172° C.

Elemental analysis (for $C_{32}H_{34}N_6O.0.5H_2O$):

Calculated (%): C, 72.84; H, 7.69; N, 15.93

Found (%): C, 73.08; H, 7.61; N, 16.03

EXAMPLE 33

Production of 2-t-butyl-6-[3-[4-(diphenylmethoxy) piperidino]propoxy][1,2,4]triazolo[1,5-b]pyridazine fumarate 911 mg of 4-(diphenylmethoxy)-1-piperidinepropanol was dissolved in 20 ml of dry tetrahydrofuran; 296 mg of sodium t-butoxide was added, followed by heating and refluxing for 30 minutes. After cooling, 589 mg of 2-t-butyl-6-chloro[1,2,4]triazolo[1,5-b]pyridazine was added, followed by heating and refluxing for 6 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the residue was dissolved in 10 ml of ethyl acetate; a solution of 102 mg of fumaric acid in 10 ml of methanol was added, followed by concentration. The residue was recrystallized from ethyl acetate to yield 382 mg of the title compound.

Melting point : 170–172° C.
Elemental analysis (for $C_{34}H_{41}N_5O_6$):
Calculated (%): C, 66.32; H, 6.71; N, 11.37
Found (%): C, 66.15; H, 6.74; N, 11.28

EXAMPLE 34

Production of 2-t-butyl-6-[3-[4-(diphenylmethoxy) piperidino]propylamino][1,2,4]triazolo[1,5-b]pyridazine fumarate 276 mg of 2-t-butyl-6-chloro[1,2,4]triazolo[1,5-b]pyridazine and 0.425 g of 4-(diphenylmethoxy)-1-piperidinepropanamine were suspended in 8 ml of n-butanol; 0.45 ml of N-ethyldiisopropylamine was added, followed by heating and refluxing for 40 hours. Ice water and sodium hydrogen carbonate were added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the residue was dissolved in 10 ml of ethyl acetate; a solution of 40 mg of fumaric acid in 5 ml of methanol was added, followed by concentration. The residue was powdered by the addition of ethyl ether, filtered and collected to yield 164 mg of the title compound.

Melting point : Softened from 80° C.
Elemental analysis (for $C_{34}H_{42}N_6O_5 \cdot H_2O, 0.5\ Et_2O$):
Calculated (%): C, 64.55; H, 7.37; N, 12.55
Found (%): C, 64.79; H, 7.76; N, 12.44

EXAMPLE 35

Production of 6-[6-[4-(diphenylmethoxy)piperidino] hexylamino][1,2,4]triazolo[1,5-b]pyridazine Process A: 6-(6-hydroxyhexylamino)[1,2,4]triazolo[1,5-b]pyridazine 2.03 g of 6-chloro[1,2,4]triazolo[1,5-b]pyridazine was dissolved in 20 ml of ethanol; 3.85 g of 6-amino-1-hexanol was added, followed by heating and refluxing for 19 hours. After cooling, the crystal obtained was collected by filtration, washed with ethanol and dried to yield 3.64 g of the title compound.

$^1$H-NMR (CDCl$_3$) δ ppm: 1.3–1.8 (8H, m), 3.46 (2H, t, J=6 Hz), 3.67 (2H, q, J=6 Hz), 4.58 (1H, broad s), 6.71, 7.78 (each 1H, d, J=10 Hz), 8.19 (1H, s).

Process B 1.64 g of 6-(6-hydroxyhexylamino)[1,2,4]triazolo[1,5-b]pyridazine was suspended in 40 ml of tetrahydrofuran; 2.25 g of N-ethyldiisopropylamine and 2.0 g of methanesulfonyl chloride were added, followed by stirring at room temperature for 5.5 hours. Ice water and sodium chloride were added, followed by extraction with ethyl acetate-tetrahydrofuran (2:1); the extract was washed with saturated saline and dried with magnesium sulfate. After the dry product was concentrated under reduced pressure, the residue was dissolved in 14 ml of acetonitrile; 743 mg of 4-(diphenylmethoxy)piperidine, 457 mg of potassium iodide and 380 mg of potassium carbonate were added, followed by stirring at 50° C. for 16 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the crystal obtained was recrystallized from acetic ether-ethyl ether (1:1) to yield 597 mg of the title compound.

Melting point : 97–98° C.
Elemental analysis (for $C_{29}H_{36}N_7O$):
Calculated (%): C, 71.87; H, 7.49; N, 17.34
Found (%): C, 71.77; H, 7.37; N, 17.36

EXAMPLE 36

Production of methyl 6-[3-[4-(diphenylmethoxy) piperidino] propylamino](1,2,4]triazolo[1,5-b] pyridazine-2-carboxylate 0.92 g of methyl 6-chloro [1,2,4]triazolo[1,5-b]pyridazine-2-carboxylate and 1.40 g of 4-(diphenylmethoxy)-1-piperidinepropanamine were suspended in 20 ml of N,N-dimethylformamide; 1.49 ml of N-ethyldiisopropylamine was added, followed by heating and refluxing at 80° C. for 15 hours. After cooling, ice water and sodium chloride were added, followed by extraction with ethyl acetate-tetrahydrofuran (1:2); the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the residue was recrystallized from ethanol-ethyl acetate (1:2) to yield 639 mg of the title compound.

Melting point: 93–96° C.
Elemental analysis (for $C_{28}H_{32}N_6O_3 \cdot 0.5H_2O$):
Calculated (%): C, 65.99; H, 6.53; N, 16.49
Found (%): C, 65.69; H, 6.28; N, 16.58

EXAMPLE 37

Production of 6-[6-[4-(diphenylmethyl)piperazino] hexylamino][1,2,4]triazolo[1,5-b]pyridazine 1.64 g of 6-(6-hydroxyhexylamino)[1,2,4]triazolo[1,5-b]pyridazine was suspended in 40 ml of tetrahydrofuran; 2.25 g of N-ethyldiisopropylamine and 2.0 g of methanesulfonyl chloride were added, followed by stirring at room temperature for 1 hour. Ice water and sodium chloride were added, followed by extraction with ethyl acetate; the extract was washed with saturated saline and dried with magnesium sulfate. After the dry product was concentrated under reduced pressure, the residue was dissolved in 13 ml of N,N-dimethylformamide; 694 mg of 1-(diphenylmethyl) piperazine, 456 mg of potassium iodide and 379 mg of potassium carbonate were added, followed by stirring at room temperature for 2 hours and at 60° C. for 4 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the crystal obtained was recrystallized from ethyl acetate and dried to yield 702 mg of the title compound.

Melting point: 130–132° C.
Elemental analysis (for $C_{28}H_{30}N_7$):
Calculated (%): C, 71.61; H, 7.51; N, 20.88
Found (%): C, 71.39; H, 7.39; N, 21.04

EXAMPLE 38

Production of methyl 6-[3-[4-(diphenylmethoxy) piperidino] propoxy]imidazo[1,2-b]pyridazine fumarate 159 mg of sodium t-butoxide was dissolved in 15 ml of N,N-dimethylformamide; 489 mg of 4-(diphenylmethoxy)-1-piperidinepropanol was added, followed by stirring at 60° C. for 30 minutes. After cooling, 253 mg of 6-chloroimidazo[1,2-b]pyridazine was added, followed by stirring at 80–90° C. for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (90:10:1). The desired fraction was collected, dissolved in 10 ml of ethyl acetate; a solution of 93 mg of fumaric acid in 10 ml of methanol was added, followed by concentration. The crystal precipitated was collected by filtration, washed with ethyl acetate and dried to yield 288 mg of the title compound.

Melting point: 155–157° C.
Elemental analysis (for $C_{31}H_{34}N_4O_6 \cdot H_2O$):
Calculated (%): C, 64.57; H, 6.29; N, 9.72
Found (%): C, 64.24; H, 5.98; N, 9.28

EXAMPLE 39

Production of 6-[3-[4-(diphenylmethoxy)piperidino] propylamino]imidazo[1,2-b]pyridazine fumarate [2:3]

325 mg of 4-(diphenylmethoxy)-1-piperidinepropanamine and 184 mg of 6-chloroimidazo[1,2-b]pyridazine were stirred at 180° C. for 1 hour. After cooling, aqueous sodium bicarbonate was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (90:10:1). The desired fraction was collected, dissolved in 10 ml of ethyl acetate; a solution of 193 mg of fumaric acid in 10 ml of methanol was added, followed by concentration. Acetone was added to the residue; the crystal precipitated was collected by filtration, washed with acetone and dried to yield 246 mg of the title compound.

Melting point: 137–139° C.
Elemental analysis (for $C_{33}H_{37}N_5O_7 \cdot 0.5H_2O$):
Calculated (%): C, 63.45; H, 6.13; N, 11.21
Found (%): C, 63.66; H, 6.00; N, 11.12

EXAMPLE 40

Production of ethyl 2-[6-[3-[4-(diphenylmethoxy) piperidino] propylamino]imidazo[1,2-b]pyridazin-2-yl]-2-methylpropionate difumarate 4.2 g of 4-(diphenylmethoxy)-1-piperidinepropanamine and 1.76 g of ethyl 2-[6-chloroimidazo[1,2-b]pyridazin-2-yl]-2-methylpropionate were stirred at 190–200° C. for 3.5 hours. After cooling, aqueous sodium bicarbonate was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (100:5:1). The desired fraction was collected, dissolved in 16 ml of ethyl acetate; a solution of 867 mg of fumaric acid in 16 ml of methanol was added, followed by concentration. Acetone was added to the residue; the crystal precipitated was collected by filtration, washed with acetone and dried to yield 2.30 g of the title compound.

Melting point: 126–128° C.
Elemental analysis (for $C_{41}H_{49}N_5O_{11}$):
Calculated (%): C, 62.50; H, 6.27; N, 8.89
Found (%): C, 62.28; H, 6.15; N, 8.97

EXAMPLE 41

Production of 6-[3-[4-(diphenylmethoxy)piperidino] propoxy]-2-methoxyimidazo[1,2-b]pyridazine 758 mg of 4-(diphenylmethoxy)-1-piperidinepropanol was dissolved in 40 ml of N,N-dimethylformamide; 102 mg of a 60% sodium hydride dispersion in mineral oil was added, followed by stirring at 60° C. for 40 minutes. After cooling, 428 mg of 6-chloro-2-methoxyimidazo[1,2-b]pyridazine was added, followed by stirring at 100° C. for 2.5 hours. After cooling, ice water and sodium chloride were added, followed by extraction with ethyl acetate-tetrahydrofuran (1:2); the extract was washed with saturated saline and dried with magnesium sulfate. After the dry product was concentrated under reduced pressure, the residue was subjected to silica gel column chromatography and eluted with ethyl acetate:methanol:triethylamine (50:5:1). The desired fraction was collected and concentrated; the crystal precipitated was recrystallized from ethanol to yield 499 mg of the title compound.

Melting point: 133–135° C.
Elemental analysis (for $C_{28}H_{32}N_4O_3$):
Calculated (%): C, 71.16; H, 6.83; N, 11.86
Found (%): C, 71.23; H, 6.83; N, 11.94

EXAMPLE 42

Production of 6-[3-[4-(diphenylmethyl)piperazno] propoxy]-2-methoxyimidazo[1,2-b]pyridazine 251 mg of 4-(diphenylmethyl)-1-piperazinepropanol was dissolved in 14 ml of N,N-dimethylformamide; 36 mg of a 60% sodium hydride dispersion in mineral oil was added, followed by stirring at 60° C. for 30 minutes. After cooling, 149 mg of 6-chloro-2-methoxyimidazo[1,2-b]pyridazine was added, followed by stirring at 90° C. for 4.5 hours. After cooling, ice water and sodium chloride were added, followed by extraction with ethyl acetate-tetrahydrofuran (1:2); the extract was washed with saturated saline and dried with magnesium sulfate. After the dry product was concentrated under reduced pressure, the residue was subjected to silica gel column chromatography and eluted with ethyl acetate. The desired fraction was collected; the crystal precipitated was recrystallized from ethyl acetate to yield 99 mg of the title compound.

Melting point: 144–146° C.
Elemental analysis (for $C_{27}H_{31}N_5O_2$):

Calculated (%): C, 70.87; H, 6.83; N, 15.31

Found (%) C, 70.79; H, 6.82; N, 13.39

EXAMPLE 43

Production of 2-[6-[3-[4-(diphenylmethoxy) piperidino] propylamino]imidazo[1,2-b]pyridazin-2-yl]-2-methylpropionic acid 468 mg of ethyl 2-[6-[3-[4-(diphenylmethoxy)piperidino]propylamino]imidazo[1,2-b]pyridazin-2-yl]-2-methylpropionate was dissolved in 3 ml of ethanol; 2 ml of a 1 N aqueous solution of sodium hydroxide was added, followed by stirring at room temperature for 15 hours. After the mixture was concentrated under reduced pressure, the residue was diluted with water and washed with ethyl acetate; the water layer was adjusted to pH 7 by the addition of 1 N hydrochloric acid, followed by extraction with ethyl acetate-tetrahydrofuran (1:1); the extract was washed with saturated saline and dried with magnesium sulfate. After the dry product was concentrated under reduced pressure, ethyl acetate was added to the residue; the crystal precipitated was collected by filtration, washed with ethyl acetate and dried to yield 267 mg of the title compound.

Melting point: 205–206° C.

Elemental analysis (for $C_{31}H_{37}N_5O_3$):

Calculated (%): C, 70.56; H, 7.07; N, 13.27

Found (%): C, 70.46; H, 7.06; N, 13.36

EXAMPLE 44

Production of t-butyl 2-6-[3-[4-(diphenylmethoxy) piperidino]propoxy]imidazo[1,2-b]pyridazin-2-yl]-2-methylpropionate difumarate 70 mg of 60% sodium hydride dispersion in mineral oil was dissolved in 5 ml of N,N-dimethylformamide; 570 mg of 4-(diphenylmethoxy)-1-piperidinepropanol was added, followed by stirring at room temperature under reduced pressure for 30 minutes. After 520 mg of t-butyl 2-(6-chloroimidazo[1,2-b]pyridazin-2-yl)-2-methylpropionate was added, followed by stirring at room temperature for 8 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol:triethylamine (195:5:1). The desired fraction was collected and dissolved in 5 ml of ethyl acetate; a solution of 233 mg of fumaric acid in 10 ml of methanol was added, followed by concentration. The crystal precipitated was collected by filtration, washed with acetone and dried to yield 631 mg of the title compound.

Melting point: 162–164° C.

Elemental analysis (for $C_{43}H_{52}N_4O_{12}$):

Calculated (%): C, 63.22; H, 6.42; N, 6.86

Found (%): C, 62.91; H, 6.36; N, 6.90

EXAMPLE 45

Production of 2-6-[3-[4-(diphenylmethoxy) piperidino]propoxy]imidazo[1,2-b]pyridazin-2-yl]-2-methylpropionic acid 818 mg of t-butyl 2-6-[3-[4-(diphenylmethoxy) piperidino]propoxy]imidazo[1,2-b]pyridazin-2-yl]-2-methylpropionate was dissolved in 8 ml of n-butanol; 393 mg of potassium hydroxide was added, followed by stirring at 90° C. for 14 hours. After cooling, the water layer was added to 7 ml of 1 N hydrochloric acid, followed by extraction with ethyl acetate; the extract was washed with saturated saline and dried with magnesium sulfate. After the dry product was concentrated under reduced pressure, ethyl acetate was added to the residue; the crystal precipitated was collected by filtration, washed with ethyl acetate and dried to yield 465 mg of the title compound.

Melting point: 183–185° C.

Elemental analysis (for $C_{31}H_{36}N_4O._42.5H_2O$):

Calculated (%): C, 64.90; H, 7.20; N, 9.77

Found (%): C, 65.15; H, 6.73; N, 9.52

EXAMPLE 46

Production of ethyl 2-6-[3-[4-(diphenylmethoxy) piperidino]propoxy]imidazo[1,2-b]pyridazin-2-yl]-2-methylpropionate difumarate 529 mg of 2-6-[3-[4-(diphenylmethoxy)piperidino]propoxy]imidazo[1,2-b]pyridazin-2-yl]-2-methylpropionic acid was dissolved in 3 ml of N,N-dimethylformamide; 0.207 ml of N-ethyldiisopropylamine and 0.135 ml of ethyl iodide were added, followed by stirring at room temperature for 15 hours. Ice water was added to the reaction mixture, followed by extraction with ethyl acetate; the extract was washed with saturated saline and dried with magnesium sulfate. After the dry product was concentrated under reduced pressure, the residue was subjected to silica gel column chromatography and eluted with ethyl acetate-:methanol:triethylamine (100:5:1). The desired fraction was collected and dissolved in 3 ml of ethyl acetate; a solution of 153 mg of fumaric acid in 3 ml of methanol was added, followed by concentration. The crystal precipitated was collected by filtration, washed with ethyl acetate and dried to yield 406 mg of the title compound.

Melting point: 116–122° C.

Elemental analysis (for $C_{41}H_{48}N_4O_{12}.0.5H_2O$):

Calculated (%): C, 61.72; H, 6.19; N, 7.02

Found (%): C, 61.61; H, 6.11; N, 6.85

EXAMPLE 47

Production of 6-[2-[2-[4-(diphenylmethyl) piperazino]ethoxy]ethoxy]-7-methyl[1,2,4]triazolo [1,5-b]pyridazine 260 mg of 60% sodium hydride dispersion in mineral oil was suspended in 20 ml of tetrahydrofuran; 1.15 g of 4-(diphenylmethyl)-1-[2-(2-hydroxyethoxy)ethyl]piperazine was added, followed by heating and refluxing for 1 hour. After cooling, 540 mg of 6-chloro-7-methyl[1,2,4]triazolo[1,5-b]pyridazine was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane-ethyl acetate-methanol (10:10:1). The desired fraction was collected; the crystal precipitated was collected by filtration, washed with ethyl ether and dried to yield 730 mg of the title compound.

Melting point: 71–72° C.

Elemental analysis (for $C_{27}H_{32}N_6O_2$):

Calculated (%): C, 68.62; H, 6.82; N, 17.78
Found (%): C, 68.35; H, 6.71; N, 17.79

EXAMPLE 48

Production of 6-[2-[2-[4-(diphenylmethyl)piperazino]ethoxy]ethoxy][1,2,4]triazolo[1,5-b]pyridazine dihydrochloride 100 mg of 60% sodium hydride in oil was suspended in 20 ml of tetrahydrofuran; 470 mg of 4-(diphenylmethyl)-1-[2-(2-hydroxyethoxy)ethyl]piperazine was added, followed by heating and refluxing for 1 hour. After cooling, 200 mg of 6-chloro[1,2,4]triazolo[1,5-b]pyridazine was added, followed by heating and refluxing for 4.5 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane-ethyl acetate-methanol (10:10:1). The desired fraction was collected and dissolved in 5 ml of ethyl acetate; 0.83 ml of a 4 N hydrogen chloride solution in ethyl acetate was added; the crystal precipitated was collected by filtration, washed with ethyl ether and dried to yield 0.54 g of the title compound.

Melting point: 182–184° C.
Elemental analysis (for $C_{26}H_{32}N_4O_2Cl_2 \cdot H_2O$):
Calculated (%): C, 56.83; H, 6.24; N, 15.29
Found (%): C, 56.98; H, 6.10; N, 15.39

EXAMPLE 49

Production of 6-[4-[4-(diphenylmethyl)piperazino]butoxy]-7-methyl[1,2,4]triazolo[1,5-b]pyridazine dihydrochloride 240 mg of a 60% sodium hydride dispersion in mineral oil was suspended in 20 ml of tetrahydrofuran; 0.99 g of 4-(diphenylmethyl)-1-piperazinebutanol was added, followed by heating and refluxing for 1 hour. After cooling, 510 mg of 6-chloro-7-methyl[1,2,4]triazolo[1,5-b]pyridazine was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane-ethyl acetate-methanol (20:20:1). The desired fraction was collected and dissolved in 5 ml of ethyl acetate; 0.64 ml of a 4 N hydrogen chloride solution in ethyl acetate was added; the crystal precipitated was collected by filtration, washed with ethyl ether and dried to yield 470 mg of the title compound.

Melting point: 190–192° C.
Elemental analysis (for $C_{27}H_{34}N_6OCl_2 \cdot 0.5AcOEt \cdot H_2O$):
Calculated (%): C, 58.88; H, 6.82; N, 14.21
Found (%): C, 59.11; H, 6.82; N, 14.03

EXAMPLE 50

Production of 6-[2-[2-[4-(diphenylmethyl)piperazino]-ethoxy]ethylthio][1,2,4]triazolo[1,5-b]pyridazine dihydrochloride Process A: 6-[2-(2-bromoethoxy)ethylthio][1,2,4]triazolo[1,5-b]pyridazine 2.8 ml of methyl 3-mercaptopropionate was dissolved in 10 ml of methanol; 19.4 ml of a 2 N sodium methoxide solution in methanol and 1.0 g of 6-chloro[(1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 20 ml of tetrahydrofuran; 1.63 ml of 2-bromoethyl ether was added, followed by heating and refluxing for 2 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane:ethyl acetate:methanol (20:20;1). The desired fraction was collected to yield 0.60 g of the title compound as an oily substance.

$^1$H-NMR (CDCl$_3$) δ ppm: 3.49 (2H, t, J=6 Hz), 3.55 (2H, t, J=6 Hz), 3.86 (2H, t, J=6 Hz), 3.90 (2H, t, J=6 Hz), 7.22, 7.93 (each 1H, d, J=9 Hz), 8.37 (1H, s).

Process B 890 mg of 6-[2-(2-bromoethoxy)ethylthio][1,2,4]triazolo[1,5-b]pyridazine and 740 mg of 4-(diphenylmethyl)piperazine were dissolved in 10 ml of N,N-dimethylformamide; 490 mg of potassium carbonate was added, followed by stirring at room temperature for 24 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane:methanol (10:1). The desired fraction was collected and concentrated; the residue was dissolved in 5 ml of ethyl acetate; 1.64 ml of a 4 N hydrogen chloride solution in ethyl acetate was added; the N,N-dimethylformamide precipitated was collected by filtration, washed with ethyl ether and dried to yield 1.13 g of the title compound.

Melting point: 188–189° C.
Elemental analysis (for $C_{26}H_{32}N_6OSCl_2 \cdot H_2O$):
Calculated (%): C, 55.22; H, 6.06; N, 14.86
Found (%): C, 55.49; H, 6.02; N, 15.08

EXAMPLE 51

Production of 6-[6-[4-(diphenylmethyl)piperazino]hexyloxy]-7-methyl[1,2,4]triazolo[1,5-b]pyridazine dihydrochloride 210 mg of 60% sodium hydride in oil was suspended in 15 ml of tetrahydrofuran; 0.91 g of 4-(diphenylmethyl)-1-piperazinehexanol was added, followed by heating and refluxing for 1 hour. After cooling, 440 mg of 6-chloro-7-methyl[1,2,4]triazolo[1,5-b]pyridazine was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane-ethyl acetate-methanol (10:10:1). The desired fraction was collected and dissolved in 5 ml of ethyl acetate; 1.44 ml of a 4 N hydrogen chloride solution in ethyl acetate was added; the crystal precipitated was collected by filtration, washed with ethyl ether and dried to yield 1.06 g of the title compound, which was then recrystallized from ethanol.

Melting point: 170–172° C.
Elemental analysis (for $C_{29}H_{38}N_6OCl_2 \cdot 0.5EtOH$):

Calculated (%): C, 62.06; H, 7.11; N, 14.47
Found (%): C, 61.77; H, 6.94; N, 14.33

EXAMPLE 52

Production of 6-[6-[4-(diphenylmethoxy)piperidino] hexyloxy]-7-methyl[1,2,4]triazolo[1,5-b]pyridazine hydrochloride 160 mg of 60% sodium hydride in oil was suspended in 20 ml of tetrahydrofuran; 1.24 g of 4-(diphenylmethoxy)-1-piperidinehexanol was added, followed by heating and refluxing for 1 hour. After cooling, 570 mg of 6-chloro-7-methyl[1,2,4]triazolo[1,5-b]pyridazine was added, followed by heating and refluxing for 1 hour. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate-methanol (10:1). The desired fraction was collected and dissolved in 5 ml of ethyl acetate; 0.54 ml of a 4 N hydrogen chloride solution in ethyl acetate was added; the crystal precipitated was collected by filtration, washed with ethyl ether and dried to yield 0.70 g of the title compound.

Melting point: 208–209° C.
Elemental analysis (for $C_{30}H_{38}N_5O_2Cl.0.8H_2O$):
Calculated (%): C, 65.45; H, 7.25; N, 12.72
Found (%): C, 65.47; H, 7.21; N, 12.60

EXAMPLE 53

Production of 6-[2-[2-[4-(diphenylmethoxy) piperidino] ethoxy]ethoxy]-7-methyl[1,2,4]triazolo [1,5-b]pyridazine 190 mg of 60% sodium hydride in oil was suspended in 15 ml of tetrahydrofuran; 1.47 g of 4-(diphenylmethoxy)-1-[2-(2-hydroxyethoxy)ethyl]piperidine was added, followed by heating and refluxing for 1 hour. After cooling, 660 mg of 6-chloro-7-methyl[1,2,4]triazolo[1,5-b]pyridazine was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate-methanol (10:1). The desired fraction was collected; the crystal precipitated was collected by filtration, washed with ethyl ether and dried to yield 1.23 g of the title compound.

Melting point: 80–82° C.
Elemental analysis (for $C_{27}H_{32}N_6O_2$):
Calculated (%): C, 68.97; H, 6.82; N, 14.36
Found (%): C, 68.75; H, 6.70; N, 14.57

EXAMPLE 54

Production of 6-[6-[4-(diphenylmethyl)piperazino] hexylthio]-7-methyl[1,2,4]triazolo[1,5-b]pyridazine dihydrochloride Process A: 6-(6-bromohexylthio)-7-methyl[1,2,4]triazolo[1,5-b]pyridazine 5.57 g of methyl 3-mercaptopropionate was dissolved in 20 ml of methanol; 35.58 ml of a 2 N sodium methoxide solution in methanol and 2.0 g of 6-chloro-7-methyl[1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 30 ml of tetrahydrofuran; 3.65 ml of 1,6-dibromohexane was added, followed by heating and refluxing for 3 hours. After cooling, ice water was added, followed by extraction with ethyl acetate; the extract was washed with saturated saline and dried with magnesium sulfate. After the dry product was concentrated under reduced pressure, ethyl ether was added to the residue; the crystal precipitated was collected by filtration to yield 2.42 g of the title compound.

$^1$H-NMR (CDCl$_3$) δ ppm: 1.49–1.54 (4H, m), 1.75–1.95 (4H, m), 2.40 (3H, s), 3.31 (2H, t, J=7 Hz), 3.43 (2H, t, J=7 Hz), 7.72 (1H, s), 8.30 (1H, s).

Process B 1.0 g of 6-(6-bromohexylthio)-7-methyl[1,2,4]triazolo[1,5-b]pyridazine and 770 mg of 1-(diphenylmethyl)piperazine were dissolved in 10 ml of N,N-dimethylformamide; 500 mg of potassium carbonate was added, followed by stirring at room temperature for 18 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate-:methanol (20:1). The desired fraction was collected and concentrated; the residue was dissolved in 5 ml of ethyl acetate; 1.96 ml of a 4 N hydrogen chloride solution in ethyl acetate was added; the crystal precipitated was collected by filtration, washed with ethyl ether and dried to yield 0.98 g of the title compound.

Melting point: 180–182° C.
Elemental analysis (for $C_{29}H_{38}N_6SCl_2.0.4H_2O$):
Calculated (%): C, 59.97; H, 6.73; N, 14.47
Found (%): C, 60.17; H, 6.55; N, 14.62

EXAMPLE 55

Production of 6-[2-[2-[4-(diphenylmethyl) piperazino] ethoxy]ethylthio]-7-methyl[1,2,4] triazolo[1,5-b]pyridazine dihydrochloride Process A: 6-[2-(2-bromoethoxy)ethylthio]-7-methyl[1,2,4]triazolo[1,5-b]pyridazine 5.57 g of methyl 3-mercaptopropionate was dissolved in 20 ml of methanol; 35.58 ml of a 2 N sodium methoxide solution in methanol and 2.0 g of 6-chloro-7-methyl[1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 30 ml of tetrahydrofuran; 2.98 ml of 2-bromoethyl ether was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane:ethyl acetate:methanol (30:30:1). The desired fraction was collected to yield 2.06 g of the title compound as an oily substance.

$^1$H-NMR (CDCl$_3$) δ ppm: 2.42 (3H, s), 3.50 (2H, t, J=6 Hz), 3.56 (2H, t, J=6 Hz), 3.86 (2H, t, J=6 Hz), 3.91 (2H, t, J=6 Hz), 7.74 (1H, s), 8.30 (1H, s).

Process B 1.0 g of 6-[2-(2-bromoethoxy)ethylthio]-7-methyl[1,2,4]triazolo[1,5-b]pyridazine and 790 mg of 1-(diphenylmethyl)

piperazine were dissolved in 10 ml of N,N-dimethylformamide; 520 mg of potassium carbonate was added, followed by stirring at room temperature for 23 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane:ethyl acetate:methanol (5:5:1). The desired fraction was collected and concentrated; the residue was dissolved in 5 ml of ethyl acetate; 1.55 ml of a 4 N hydrogen chloride solution in ethyl acetate was added; the crystal precipitated was collected by filtration, washed with ethyl ether and dried to yield 0.85 g of the title compound, which was then recrystallized from ethanol.

Melting point: 198–200° C.
Elemental analysis (for $C_{27}H_{34}N_6OSCl_2$):
Calculated (%): C, 57.75; H, 6.10; N, 14.97
Found (%): C, 57.53; H, 6.00; N, 14.93

EXAMPLE 56

Production of 6-[6-[4-(diphenylmethoxy)piperidino] hexylthio]-7-methyl[1,2,4]triazolo[1,5-b]pyridazine fumarate 1.0 g of 6-(6-bromohexylthio)-7-methyl[1,2,4]triazolo[1, 5-b]pyridazine and 810 mg of 4-(diphenylmethoxy) piperidine were dissolved in 10 ml of N,N-dimethylformamide; 500 mg of potassium carbonate was added, followed by stirring at room temperature for 24 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected and concentrated; the residue was dissolved in 10 ml of ethanol; 290 mg of fumaric acid was added, followed by concentration. Ethyl ether was added to the residue; the crystal precipitated was collected by filtration, washed with ethyl ether and dried to yield 1.43 g of the title compound.

Melting point: 137–138° C.
Elemental analysis (for $C_{34}H_{41}N_5O_5S.0.5H_2O$):
Calculated (%): C, 63.73; H, 6.61; N, 10.93
Found (%): C, 63.97; H, 6.44; N, 11.00

EXAMPLE 57

Production of 6-[2-[2-[4-(diphenylmethoxy) piperidino] ethoxy]ethylthio]-7-methyl[1,2,4] triazolo[1,5-b]pyridazine fumarate 1.09 g of 6-[2-(2-bromoethoxy)ethylthio]-7-methyl[1,2, 4]triazolo[1,5-b]pyridazine and 840 mg of 4-(diphenylmethoxy)piperidine were dissolved in 10 ml of N,N-dimethylformamide; 520 mg of potassium carbonate was added, followed by stirring at room temperature for 23 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with dichloromethane:ethyl acetate:methanol (5:5:1). The desired fraction was collected; the residue was dissolved in 10 ml of ethanol; 200 mg of fumaric acid was added, followed by concentration. Ethyl ether was added to the residue; the crystal precipitated was collected by filtration, washed with ethyl ether and dried to yield 0.78 g of the title compound.

Melting point: 119–122° C.
Elemental analysis (for $C_{32}H_{37}N_5O_6S.0.5H_2O$):
Calculated (%): C, 61.13; H, 6.09; N, 11.14
Found (%): C, 61.12; H, 5.82; N, 11.40

EXAMPLE 58

Production of 6-[2-[2-[4-(diphenylmethoxy) piperidino]ethoxy]ethylthio][1,2,4]triazolo[1,5-b] pyridazine fumarate 1.35 g of 6-[2-(2-bromoethoxy)ethylthio][1,2,4] triazolo [1,5-b]pyridazine and 1.19 g of 4-(diphenylmethoxy) piperidine were dissolved in 15 ml of N,N-dimethylformamide; 740 mg of potassium carbonate was added, followed by stirring at room temperature for 17 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected; the residue was dissolved in 10 ml of ethanol; 360 mg of fumaric acid was added, followed by concentration. Ethyl ether was added to the residue; the crystal precipitated was collected by filtration, washed with ethyl ether and dried to yield 1.64 g of the title compound.

Melting point: 110–111° C.
Elemental analysis (for $C_{31}H_{35}N_5O_6S.0.5H_2O$):
Calculated (%): C, 60.57; H, 5.90; N, 11.39
Found (%): C, 60.35; H, 5.73; N, 11.16

EXAMPLE 59

Production of 6-[2-[2-[4-(diphenylmethyl) piperazino]ethoxy]ethylthio]-7-isopropyl[1,2,4] triazolo[1,5-b]pyridazine dihydrochloride Process A: 6-[2-(2-bromoethoxy)ethylthio]-7-isopropyl [1,2,4]triazolo[1,5-b]pyridazine 2.05 g of methyl 3-mercaptopropionate was dissolved in 10 ml of methanol; 7.64 ml of a 2 N sodium methoxide solution in methanol and 1.0 g of 6-chloro-7-isopropyl[1,2, 4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 15 ml of tetrahydrofuran; 1.28 ml of 2-bromoethyl ether was added, followed by heating and refluxing for 2 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (20:1). The desired fraction was collected to yield 0.98 g of the title compound.

$^1$H-NMR (CDCl$_3$) δ ppm: 1.35 (6H, s), 3.15–3.30 (1H, m), 3.50 (2H, t, J=6 Hz), 3.55 (2H, t, J=6 Hz), 3.86 (2H, t, J=6 Hz), 3.91 (2H, t, J=6 Hz), 7.80 (1H, s), 8.31 (1H, s).

Process B 0.98 g of 6-[2-(2-bromoethoxy)ethylthio]-7-isopropyl[1, 2,4]triazolo[1,5-b]pyridazine and 720 mg of 1-(diphenylmethyl)piperazine were dissolved in 10 ml of N,N-dimethylformamide; 470 mg of potassium carbonate was added, followed by stirring at room temperature for 15 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected and concentrated; the residue was dissolved in 5 ml of ethyl acetate; 1.45 ml of a 4 N hydrogen chloride solution in ethyl acetate was added; the crystal precipitated was collected by filtration, washed with ethyl ether and dried to yield 1.04 g of the title compound, which was then recrystallized from ethanol.

Melting point: 143–145° C.
Elemental analysis (for $C_{29}H_{38}N_6OSCl_2 \cdot H_2O$):
Calculated (%): C, 57.32; H, 6.64; N, 13.83
Found (%): C, 57.20; H, 6.43; N, 13.89

EXAMPLE 60

Production of 6-[2-[2-[4-(diphenylmethyl) piperazino]ethoxy]ethylthio]-7-t-butyl[1,2,4]triazolo [1,5-b]pyridazine Process A: 6-[2-[(2-bromoethoxy) ethylthio]-7-t-butyl[1,2,4]triazolo[1,5-b]pyridazine 2.23 g of methyl 3-mercaptopropionate was dissolved in 10 ml of methanol; 7.2 ml of a 2 N sodium methoxide solution in methanol and 1.0 g of 6-chloro-7-t-butyl[1,2,4]triazolo[1,5-b] pyridazine were added, followed by heating and refluxing for 1 hour. After cooling, the mixture was concentrated under reduced pressure; ethyl acetate was added to the residue; the crystal precipitated was collected, washed with ethyl acetate and suspended in 20 ml of tetrahydrofuran; 1.19 ml of 2-bromoethyl ether was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:hexane (2:1). The desired fraction was collected to yield 1.06 g of the title compound.

$^1$H-NMR (CDCl$_3$) δ ppm: 1.56 (9H, s), 3.50 (2H, t, J=6 Hz), 3.58 (2H, t, J=6 Hz), 3.86 (2H, t, J=6 Hz), 3.92 (2H, t, J=6 Hz), 7.94 (1H, s), 8.32 (1H, s).

Process B 1.06 g of 6-[2-(2-bromoethoxy)ethylthio]-7-t-butyl[1,2,4] triazolo[1,5-b]pyridazine and 740 mg of 1-(diphenylmethyl) piperazine were dissolved in 10 ml of N,N-dimethylformamide; 480 mg of potassium carbonate was added, followed by stirring at room temperature for 18 hours. Ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (20:1). The desired fraction was collected and concentrated; the crystal precipitated was collected by filtration, washed with ethyl ether and dried to yield 0.85 g of the title compound.

Melting point: 106–108° C.
Elemental analysis (for $C_{30}H_{38}N_6OS$):
Calculated (%): C, 67.89; H, 7.22; N, 15.83
Found (%): C, 67.65; H, 7.33; N, 15.98

EXAMPLE 61

Production of 6-[2-[2-[4-(diphenylmethyl) piperazino] ethoxy]ethoxy]-7-isopropyl[1,2,4] triazolo[1,5-b]pyridazine 160 mg of 60% sodium hydride in oil was suspended in 20 ml of tetrahydrofuran; 1.20 g of 4-(diphenylmethyl)-1-[2-(2-hydroxyethoxy)ethyl]piperazine was added, followed by heating and refluxing for 1 hour. After cooling, 610 mg of 6-chloro-7-isopropyl[1,2,4]triazolo[1,5-b]pyridazine was added, followed by heating and refluxing for 1 hour. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected; the crystal precipitated was collected by filtration, washed with ethyl ether and dried to yield 790 mg of the title compound.

Melting point: 119–120° C.
Elemental analysis (for $C_{29}H_{36}N_6O_2 \cdot 0.5H_2O$):
Calculated (%): C, 68.34; H, 7.32; N, 16.49
Found (%): C, 68.64; H, 7.31; N, 16.54

EXAMPLE 62

Production of 6-[2-[2-[4-(diphenylmethyl) piperazino] ethoxy]ethoxy]-7-t-butyl[1,2,4]triazolo (1,5-b]pyridazine dihydrochloride 150 mg of 60% sodium hydride was suspended in 20 ml of tetrahydrofuran; 1.05 g of 4-(diphenylmethyl)-1-[2-(2-hydroxyethoxy)ethyl]piperazine in oil was added, followed by heating and refluxing for 1 hour. After cooling, 650 mg of 6-chloro-7-t-butyl[1,2,4]triazolo[1,5-b]pyridazine was added, followed by heating and refluxing for 2 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected; the residue was dissolved in 5 ml of ethyl acetate; 2.1 ml of a 4 N hydrogen chloride solution in ethyl acetate was added; the crystal precipitated was collected by filtration, washed with ethyl ether and dried to yield 1.55 g of the title compound.

Melting point: 150–152° C.
Elemental analysis (for $C_{30}H_{40}N_6O_2Cl_2 \cdot 0.5H_2O$):
Calculated (%): C, 60.39; H, 6.92; N, 14.09
Found (%): C, 60.20; H, 6.64; N, 14.09

EXAMPLE 63

Production of 6-[2-[2-[4-(diphenylmethoxy) piperidino] ethoxy]ethoxy]-7-t-butyl[1,2,4]triazolo [1,5-b]pyridazine fumarate 120 mg of 60% sodium hydride in oil was suspended in 20 ml of tetrahydrofuran; 0.94 g of 4-(diphenylmethoxy)-1-[2-(2-hydroxyethoxy)ethyl]piperidine was added, followed by heating and refluxing for 1 hour. After cooling, 530 mg of 6-chloro-7-t-butyl[1,2,4]triazolo[1,5-b]pyridazine was added, followed by heating and refluxing for 3 hours. After cooling, ice water was added, followed by extraction with ethyl acetate; the extract was washed with saturated saline and dried with magnesium sulfate. After the dry product was concentrated under reduced pressure, the residue was subjected to silica gel column chromatography and eluted with ethyl acetate:methanol (10:1). The desired fraction was collected; the residue was dissolved in 10 ml of ethanol; 250 mg of fumaric acid was added, followed by concentration. Ethyl ether was added to the residue; the crystal precipitated was collected by filtration, washed with ethyl ether and dried to yield 1.17 g of the title compound.

Melting point: 80–82° C.

Elemental analysis (for $C_{35}H_{43}N_6O_7·1.3H_2O$):

Calculated (%): C, 62.82; H, 6.87; N, 10.46

Found (%): C, 62.89; H, 6.69; N, 10.22

EXAMPLE 64

Production of ethyl 2-[6-[5-[4-(diphenylmethoxy) piperidino] pentylamino]imidazo[1,2-b]pyridazin-2-yl]-2-methylpropionate difumarate 1.41 g of 4-(diphenylmethoxy)-1-piperidinepentanamine and 0.536 g of ethyl 2-[6-chloroimidazo[1,2-b]pyridazin-2-yl]-2-methylpropionate were stirred at 190–200° C. for 3.5 hours. After cooling, ethyl acetate-tetrahydrofuran (2:1) was added; the mixture was washed with aqueous sodium bicarbonate and saturated saline and dried with sodium sulfate. The dry product was concentrated under reduced pressure; the residue was subjected to silica gel column chromatography and eluted with ethyl acetate:methanol:triethylamine (185:15:2). The desired fraction was collected, dissolved in 5 ml of ethanol; a solution of 235 mg of fumaric acid in 5 ml of methanol was added, followed by concentration. Ethyl ether was added to the residue; the resulting powder was collected by filtration, washed with ethyl ether and dried to yield 0.629 g of the title compound.

Melting point: 138° C.

Elemental analysis (for $C_{43}H_{53}N_5O_{11}$):

Calculated (%): C, 63.30; H, 6.55; N, 8.58

Found (%): C, 64.24; H, 6.92; N, 8.42

EXAMPLE 65

Production of ethyl 2-[6-[3-[4-(diphenylmethoxy) piperidino] -2-hydroxypropylamino]imidazo[1,2-b] pyridazin-2-yl]-2-methylpropionate difumarate 0.511 g of 3-[4-(diphenylmethoxy)piperidino]-2-hydroxypropylamine and 0.268 g of ethyl 2-[6-chloroimidazo[1,2-b]pyridazin-2-yl]-2-methylpropionate were stirred at 190–200° C. for 3 hours. After cooling, ethyl acetate-tetrahydrofuran (2:1) was added; the mixture was washed with aqueous sodium bicarbonate and saturated saline and dried with magnesium sulfate. The dry product was concentrated under reduced pressure; the residue was subjected to silica gel column chromatography and eluted with ethyl acetate:methanol:triethylamine (90:10:1). The desired fraction was collected, dissolved in 5 ml of ethyl acetate; a solution of 82 mg of fumaric acid in 5 ml of methanol was added, followed by concentration. Ethyl ether was added to the residue; the resulting powder was collected by filtration, washed with ethyl ether and dried to yield 0.223 g of the title compound.

Melting point: 145° C.

Elemental analysis (for $C_{41}H_{49}N_5O_{12}·Et_2O$):

Calculated (%): C, 61.56; H, 6.77; N, 7.98

Found (%): C, 61.39; H, 6.49; N, 7.91

EXAMPLE 66

Production of ethyl 2-[6-[3-[4-[bis(4-fluorophenyl) methoxy) piperidino]propylamino]imidazo[1,2-b] pyridazin-2-yl]-2-methylpropionate difumarate 1.62 g of 4-[bis(4-fluorophenyl)methoxy]-1-piperidinepropanamine and 0.803 g of ethyl 2-[6chloroimidazo[1,2-b]pyridazin-2-yl]-2-methylpropionate were stirred at 190–200° C. for 3 hours. After cooling, aqueous sodium bicarbonate and saline were added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (90:10:1). The desired fraction was collected, dissolved in 20 ml of ethyl acetate; a solution of 301 mg of fumaric acid in 10 ml of methanol was added, followed by concentration. Acetone was added to the residue; the crystal precipitate was collected by filtration, washed with acetone and dried to yield 0.966 g of the title compound.

Melting point: 159–161° C.

Elemental analysis (for $C_{41}H_{47}N_5O_{11}F_2·0.5H_2O$):

Calculated (%): C, 59.13; H, 5.81; N, 8.41

Found (%): C, 58.94; H, 5.84; N, 8.34

EXAMPLE 67

Production of ethyl 6-[3-[4-(diphenylmethoxy) piperidino] propylamino]imidazo[1,2-b]pyridazine-2-carboxylate difumarate 686 mg of 4-(diphenylmethoxy)-1-piperidinepropanamine and 477 mg of ethyl 6-chloroimidazo[1,2-b]pyridazin-2-carboxylate were dissolved in 7 ml of N,N-dimethylformamide; 0.73 ml of N-ethyldiisopropylamine was added, followed by stirring in an oil bath (80° C.) for 18.5 hours. After cooling, ice water and saline were added, followed by extraction with ethyl acetate-tetrahydrofuran (1:1); the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected, dissolved in 5 ml of ethyl acetate; a solution of 95 mg of fumaric acid in 5 ml of ethanol was added, followed by concentration. Acetone-ethyl ether (1:2) was added to the residue to cause recrystallization; the crystal precipitate was collected by filtration and washed with ethyl ether to yield 211 mg of the title compound.

Melting point: 176–179° C.

Elemental analysis (for $C_{38}H_{43}N_5O_{11}$):

Calculated (%): C, 61.20; H, 5.81; N, 9.39

Found (%): C, 61.17; H, 5.98; N, 9.80

EXAMPLE 68

Production of isopropyl 2-[6-[3-[4-(diphenylmethoxy)piperidino]propoxy]imidazo[1,2-b]pyridazin-2-yl]-2-methylpropionate difumarate 8.10 g of 4-(diphenylmethoxy)piperidinepropanol was dissolved in 60 ml of N,N-dimethylformamide; 1.11 g of 60% sodium hydride in oil was added, followed by stirring at room temperature under reduced pressure for 1 hour. While the solution was ice cooled, 7.79 g of isopropyl 2-(6-chloroimidazo [1,2-b]pyridazin-2-yl]-2-methylpropionate was added, followed by stirring at constant temperature for 4 hours. Ice water was added, followed by extraction with ethyl acetate-tetrahydrofuran (1:1); the extract was washed with saturated saline and dried with magnesium sulfate. The dry product was concentrated under reduced pressure; the residue was subjected to silica gel column chromatography and eluted with ethyl acetate. The desired fraction was collected and concentrated under reduced pressure; the residue was dissolved in 10 ml of ethanol; 476 mg of fumaric acid was added, followed by concentration again. The residue was crystallized by the addition of ethyl acetate, collected by filtration, washed with ethyl acetate and dried to yield 1.05 g of the title compound.

Melting point: 145–147° C.
Elemental analysis (for $C_{42}H_{50}N_4O_{12}$):
Calculated (%): C, 62.83; H, 6.28; N, 6.98
Found (%): C, 62.50; H, 6.10; N, 7.04

EXAMPLE 69

Production of ethyl 2-[6-[3-[4-[bis(4-methylphenyl) methoxy]piperidino]propylamino]imidazo[1,2-b] pyridazin-2-yl]-2-methylpropionate difumarate 2.11 g of 4-[bis(4-methylphenyl)methoxy]-1-piperidinepropanamine and 0.803 g of ethyl 2-[6-chloroimidazo[1,2-b]pyridazin-2-yl]-2-methylpropionate were stirred at 190–200° C. for 3 hours. After cooling, aqueous sodium bicarbonate was added, followed by extraction with ethyl acetate; the extract was washed with saturated saline and dried with sodium sulfate. The dry product was concentrated under reduced pressure; the residue was subjected to silica gel column chromatography and eluted with ethyl acetate:methanol:triethylamine (95:5:1). The desired fraction was collected, dissolved in 20 ml of ethyl acetate; a solution of 358 mg of fumaric acid in 20 ml of methanol was added, followed by concentration. Acetone was added to the residue; the crystal precipitated was collected by filtration, washed with acetone and dried to yield 0.901 g of the title compound.

Melting point: 159–161° C.
Elemental analysis (for $C_{43}H_{53}N_5O_{11}$):
Calculated (%): C, 63.30; H, 6.55; N, 8.56
Found (%): C, 63.29; H, 6.32; N, 8.67

EXAMPLE 70

Production of N-[6-[3-[4-(diphenylmethoxy) piperidino] propylamino]imidazo[1,2-b]pyridazine-2-carbonyl]glycine ethyl ester 1.90 g of 4-(diphenylmethoxy)-1-piperidinepropanamine and 1.38 g of N-(6-chloroimidazo-[1,2-b]pyridazine-2-carbonyl)glycine ethyl ester were dissolved in 15 ml of 1-methyl-2-pyrrolidone; 0.841 ml of N-ethyldiisopropylamine was added, followed by stirring in an oil bath (90–100° C.) for 24 hours. After cooling, ice water and saline were added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (95:5:1). The desired fraction was collected and recrystallized from ethyl acetate to yield 1.28 g of the title compound.

Melting point: 172–174° C.
Elemental analysis (for $C_{32}H_{38}N_6O_4.0.5H_2$):
Calculated (%): C, 66.30; H, 6.78; N, 14.50
Found (%): C, 66.42; H, 6.68; N, 14.55

EXAMPLE 71

Production of N-[6-[3-[4-(diphenylmethoxy) piperidino] propylaminolimidazo[1,2-b]pyridazine-2-carbonyl]glycine ethyl ester dihydrochloride 0.628 g of N-[6-[3-[4-(diphenylmethoxy)piperidino] propylamino]imidazo[1,2-b]pyridazine-2-carbonyl]glycine ethyl ester was dissolved in 10 ml of tetrahydrofuran; 1.5 ml of a 4 N hydrogen chloride solution in ethyl acetate was added, followed by concentration under reduced pressure. To the residue, 10 ml of methanol was added, followed by concentration under reduced pressure. The crystal obtained was collected and washed with ethyl acetate to yield 0.658 g of the title compound.

Melting point: 205° C.
Elemental analysis (for $C_{32}H_{40}N_6O_4Cl_2$):
Calculated (%): C, 59.72; H, 6.26; N, 13.06
Found (%): C, 59.74; H, 6.41; N, 12.63

EXAMPLE 72

Production of N-[6-[3-[4-(diphenylmethoxy) piperidino]propylamino]imidazo[1,2-b]pyridazine-2-carbonyl]glycine 0.810 g of N-[6-[3-[4-(diphenylmethoxy)piperidino] propylamino]imidazo[1,2-b]pyridazine-2-carbonyl]glycine ethyl ester was dissolved in 4 ml of ethanol; 2 ml of a 1 N aqueous solution of sodium hydroxide was added, followed by stirring at room temperature for 3 hours. The mixture was concentrated under reduced pressure; ice water and 2.1 ml of 1 N hydrochloric acid were added to the residue, followed by extraction with ethyl acetate-tetrahydrofuran (1:2); the extract was washed with saturated saline and dried with magnesium sulfate. The dry product was concentrated under reduced pressure; the residue was powdered by the addition of ethyl acetate, collected by filtration and washed with ethyl acetate to yield 0.183 g of the title compound.

Melting point: 171° C.
Elemental analysis (for $C_{30}H_{34}N_6O_4.2H_2O.AcOEt$):
Calculated (%): C, 61.25; H, 6.95; N, 12.60
Found (%): C, 61.30; H, 6.74; N, 12.45

EXAMPLE 73

Production of 2-[6-[3-[4-(diphenylmethoxy) piperidino]propylamino]imidazo[1,2-b]pyridazin-2-yl]-2-methylpropionamide dihydrochloride 1.29 g of 4-(diphenylmethoxy)-1-piperidinepropanamine and 0.478 g of 2-(6-chloroimidazo[1,2-b]pyridazin-2-yl]-2-methylpropionamide were stirred at 190–200° C. for 70 minutes. After cooling, aqueous sodium bicarbonate was added, followed by.,extraction with ethyl acetate. The extract was washed with saline and dried with magnesium sulfate. The dry product was concentrated under reduced pressure; the residue was subjected to silica gel column chromatography and eluted with ethyl acetate:methanol:triethylamine (90:10:1). The desired fraction was collected; the residue was dissolved in 10 ml of ethyl acetate; 1.5 ml of a 4 N hydrogen chloride solution in ethyl acetate was added, followed by concentration under reduced pressure. Ethyl acetate was added to the residue; the resulting powder was collected by filtration, washed with ethyl acetate and dried to yield 0.823 g of the title compound.

Melting point: 191° C.
Elemental analysis (for $C_{31}H_{40}N_6O_2Cl_2.AcOEt$):
Calculated (%): C, 64.11; H, 7.38; N, 12.82
Found (%): C, 63.70; H, 7.27; N, 12.34

EXAMPLE 74

Production of N,N-dimethyl 2-[6-[3-[4-(diphenylmethoxy)piperidino]propylaminolimidazo [1,2-b]pyridazin-2-yl]-2-methylpropionamide dihydrochloride 1.04 g of 4-(diphenylmethoxy)-1-piperidinepropanamine and 0.426 g of N,N-dimethyl 2-(6-chloroimidazo[1,2-b]

pyridazin-2-yl]-2-methylpropionamide were stirred at 190–200° C. for 60 minutes. After cooling, aqueous sodium bicarbonate was added, followed by extraction with ethyl acetate. The extract was washed with saline and dried with magnesium sulfate. The dry product was concentrated under reduced pressure; the residue was subjected to silica gel column chromatography and eluted with ethyl acetate-:methanol:triethylamine (85:15:1). The desired fraction was collected; the residue was dissolved in 10 ml of ethyl acetate; 1.5 ml of a 4 N hydrogen chloride solution in ethyl acetate was added, followed by concentration under reduced pressure. The residue was recrystallized from acetone to yield 0.823 g of the title compound.

Melting point: 183° C.

Elemental analysis (for $C_{33}H_{44}N_6O_2Cl_2 \cdot 1.5H_2O$):

Calculated (%): C, 60.54; H, 7.24; N, 11.84

Found (%): C, 60.48; H, 7.28; N, 11.90

EXAMPLE 75

Production of 2-[6-[3-[4-(diphenylmethoxy) piperidino] propylamino]imidazo[1,2-b]pyridazin-2-yl]-2-methylpropanol 1.29 g of 4-(diphenylmethoxy)-1-piperidinepropanamine and 0.451 g of 2-(6-chloroimidazo[1,2-b]pyridazin-2-yl]-2-methylpropanol were stirred at 190–200° C. for 90 minutes. After cooling, aqueous sodium bicarbonate was added, followed by extraction with ethyl acetate. The extract was washed with saline and dried with magnesium sulfate. The dry product was concentrated under reduced pressure; the residue was subjected to silica gel column chromatography and eluted with ethyl acetate:methanol:triethylamine (90:10:1). The desired fraction was collected; the residue was recrystallized from ethyl ether to yield 0.465 g of the title compound.

Melting point: 105–108° C.

Elemental analysis (for $C_{31}H_{39}N_5O_2 \cdot 0.5H_2O$):

Calculated (%): C, 71.24; H, 7.71; N, 13.40

Found (%): C, 71.22; H, 7.87; N, 13.32

EXAMPLE 76

Production of N-[6-[3-[4-(diphenylmethoxy) piperidino] propylamino]imidazo[1,2-b]pyridazine-2-carbonyl]-2,2-dimethylglycine ethyl ester dihydrochloride 1.23 g of 4-(diphenylmethoxy)-1-piperidinepropanamine and 1.18 g of N-(6-chloroimidazo[1,2-b]pyridazine-2-carbonyl]-2,2-dimethylglycine ethyl ester were dissolved in 15 ml of N,N-dimethylformamide; 1.31 ml of N-ethyldiisopropylamine was added, followed by stirring at 70° C. for 9.5 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate-:methanol:triethylamine (50:5:1). The desired fraction was collected, concentrated under reduced pressure and dissolved in 5 ml of ethyl acetate; 0.28 ml of a 4 N hydrogen chloride solution in ethyl acetate was added, followed by concentration again. Ethyl acetate was added to the residue; the crystal precipitated was collected by filtration, washed with ethyl ether and dried to yield 284 mg of the title compound.

Melting point: 194–196° C.

Elemental analysis (for $C_{34}H_{44}N_6O_4Cl_2$):

Calculated (%): C, 60.80; H, 6.60; N, 12.51

Found (%): C, 60.82; H, 6.67; N, 12.77

EXAMPLE 77

Production of ethyl 2-[6-[3-[4-(diphenylmethyl) piperazino] propylamino]imidazo[1,2-b]pyridazin-2-yl]-2-methylpropionate trihydrochloride 1.31 g of 4-(diphenylmethyl)-1-piperazinepropanamine and 567 mg of ethyl 2-(6-chloroimidazo[1,2-b]pyridazin-2-yl]-2-methylpropionate were stirred at 185° C. for 3 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected, concentrated under reduced pressure and dissolved in 5 ml of ethyl acetate; 0.80 ml of a 4 N hydrogen chloride solution in ethyl acetate was added, followed by concentration again. Ethanol was added to the residue; the crystal precipitated was collected by filtration, washed with ethanol-ethyl acetate (1:3) and dried to yield 502 mg of the title compound.

Melting point: 190–193° C.

Elemental analysis (for $C_{32}H_{43}N_6O_2Cl_3 \cdot 1.0H_2O$):

Calculated (%): C, 57.53; H, 6.79; N, 12.58

Found (%): C, 57.27; H, 6.52; N, 12.55

EXAMPLE 78

Production of 2-[6-[4-[4-(diphenylmethoxy) piperidino] butylamino]imidazo[1,2-b]pyridazin-2-yl]-2-methylpropionic acid 1.56 g of 4-(diphenylmethyl)-1-piperidinebutanamine and 617 mg of ethyl 2-(6-chloroimidazo[1,2-b]pyridazin-2yl)-2-methylpropionate were stirred at 185° C. for 3 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected, concentrated under reduced pressure and dissolved in 5 ml of ethyl acetate; 0.52 ml of a 4 N hydrogen chloride solution in ethyl acetate was added, followed by concentration. The residue was dissolved in 4 ml of ethanol; 4 ml of a 1 N aqueous solution of sodium hydroxide was added, followed by stirring at room temperature for 4 hours; 1 ml of a 2 N aqueous solution of sodium hydroxide was added, followed by stirring at 50° C. for 16 hours. The mixture was concentrated under reduced pressure; the residue was diluted with water and washed with ethyl acetate; the water layer was ajusted to pH 4.5 by the addition of 4 N hydrochloric acid and extracted with ethyl acetate-tetrahydrofuran (1:1); the extract was washed with saturated saline and dried with magnesium sulfate. The dry product was concentrated under reduced pressure; the residue was powdered by the addition of ethyl acetate, collected by filtration and dried to yield 271 mg of the title compound.

Noncrystalline
Elemental analysis (for $C_{32}H_{39}N_5O_3 \cdot 2.1H_2O, 0.5AcOEt$):
Calculated (%): C, 65.49; H, 7.63; N, 11.23
Found (%): C, 65.23; H, 7.29; N, 11.19

EXAMPLE 79

Production of 2-[6-[2-[4-(diphenylmethoxy) piperidino] ethylamino]imidazo[1,2-b]pyridazin-2-yl]-2-methylpropionic acid Process A: Production of isopropyl 2-[6-(2-hydroxyethylamino]imidazo[1,2-b]pyridazin-2-yl]-2-methylpropionate 130 mg of 2-aminoethanol and 300 mg of isopropyl 2-(6-chloroimidazo[1,2-b]pyridazin-2-yl]-2-methylpropionate were stirred at 170° C. for 4 hours. After cooling, 260 mg of 2-aminoethanol was added, followed by stirring at 170° C. for 45 minutes. After cooling, water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol (10:1). The desired fraction was collected and concentrated under reduced pressure; the crystal precipitated was collected by filtration and dried to yield 145 mg of the title compound.

$^1$H-NMR (CDCl$_3$) δ ppm: 1.29 (3H, s), 1.32 (3H, s), 1.64 (6H, s), 3.44 (2H, td, J=4.6, 6.1 Hz), 3.88 (2H, t, J=4.6 Hz), 4.96–5.15 (1H, m), 5.43 (1H, t, J=6.2 Hz), 5.72 (1H, d, J=9.7 Hz), 6.98 (1H, d, J=9.7 Hz), 7.45 (1H, s).

Process B: Production of isopropyl 2-[6-[(2-methanesulfonyloxy)ethylamino]imidazo[1,2-b]pyridazin-2-yl]-2-methylpropionate 2.18 g of isopropyl 2-[6-(2-hydroxyethylamino) imidazo[1,2-b]pyridazin-2-yl]-2-methylpropionate was suspended in 20 ml of tetrahydrofuran; 2.45 ml of N-ethyldiisopropylamine and 1.10 ml of methanesulfonyl chloride were added, followed by stirring at room temperature for 1 hour. Ice water was added, followed by extraction with ethyl acetate; the extract was washed with saturated saline and dried with magnesium sulfate. The dry product was concentrated under reduced pressure and dried to yield 2.37 g of the title compound.

$^1$H-NMR (CDCl$_3$) δ ppm: 1.19 (3H, s), 1.22 (3H, s), 1.63 (6H, s), 3.40 (3H, s), 3.74 (2H, td, J=5.1, 5.4 Hz), 4.48 (2H, t, 5.1 Hz), 4.76 (1H, t, J=5.4 Hz), 4.95–5.12 (1H, m), 6.39 (1H, d, J=9.6 Hz), 7.54 (1H, s), 7.62 (1H, d, J=9.6 Hz).

Process C: Production of isopropyl 2-[6-[2-[4-(diphenylmethoxy)piperidino]ethylamino]imidazo[1,2-b]pyridazin-2-yl]-2-methylpropionate 1.13 g of isopropyl 2-[6-[2-(methanesulfonyloxy) ethylamino]imidazo[1,2-b]pyridazin-2-yl]-2-methylpropionate was dissolved in 15 ml of N,N-dimethylformamide; 943 mg of 4-(diphenylmethoxy) piperidine, 586 mg of potassium iodide and 488 mg of potassium carbonate were added, followed by stirring at 60° C. for 2 hours. Ice water was added; the mixture was saturated with sodium chloride and extracted with ethyl acetate; the extract was washed with saturated saline and dried with magnesium sulfate. The dry product was concentrated under reduced pressure; the residue was subjected to silica gel column chromatography and eluted with ethyl acetate:methanol (10:1). The desired fraction was collected, concentrated under reduced pressure and dried to yield 571 mg of the title compound.

$^1$H-NMR (CDCl$_3$) δ ppm: 1.18 (3H, s), 1.21 (3H, s), 1.60–1.20 (4H, m), 1.62 (6H, s), 2.10–2.30 (2H, m), 2.59 (2H, t, J=5.6 Hz), 2.70–2.85 (2H, m), 3.35 (2H, dt, J=5.3, 5.6 Hz), 3.35–3.55 (1H, m), 4.90–5.10 (1H, m), 5.05 (1H), 5.53 (1H, s), 6.39 (1H, d, J=9.4 Hz), 7.16–7.39 (10H, m), 7.54 (1H, s), 7.57 (1H, d, J=9.4 Hz).

Process D 565 mg of isopropyl 2-[6-[2-[4-(diphenylmethoxy) piperidino]ethylamino]imidazo[1,2-b]pyridazin-2-yl]-2-methylpropionate was dissolved in 4 ml of ethanol; 2.04 ml of a 1 N aqueous sodium hydroxide solution was added, followed by refluxing for 20 hours. After cooling, the mixture was concentrated under reduced pressure; the residue was diluted with water and ajusted to pH 5.5 by the addition of 1 N hydrochloric acid. Ethyl acetate was added; the crystal precipitated was collected by filtration, washed with water and ethyl acetate and dried to yield 443 mg of the title compound.

Melting point: 194–198° C.
Elemental analysis (for $C_{30}H_{35}N_5O_3 \cdot 2.5H_2O$):
Calculated (%): C, 64.50; H, 7.22; N, 12.54
Found (%): C, 64.57; H, 7.03; N, 12.58

EXAMPLE 80

Production of [6-[3-[4-(diphenylmethoxy) piperidino] propylamino]imidazo[1,2-b]pyridazin-2-yl]-2-carboxylic acid 876 mg of ethyl [6-[3-[4-(diphenylmethoxy)piperidino] propylamino]imidazo[1,2-b]pyridazin-2-yl]-2-carboxylate was dissolved in 5 ml of ethanol; 1.9 ml of a 1 N aqueous sodium hydroxide solution was added, followed by stirring at room temperature for 3 hours. After the mixture was concentrated under reduced pressure, the residue was diluted with water and washed with ethyl acetate; the water layer was ajusted to pH 5 by the addition of 1 N hydrochloric acid. The crystal precipitated was collected by filtration, washed with water and ethyl acetate and dried to yield 256 mg of the title compound.

Melting point: 152–155° C.
Elemental analysis (for $C_{28}H_{31}N_5O_3 \cdot 1.5H_2O$):
Calculated (%): C, 65.61; H, 6.69; N, 13.66
Found (%): C, 65.52; H, 6.61; N, 13.61

EXAMPLE 81

Production of ethyl 2-[3-chloro-6-[3-[4-(diphenylmethoxy)piperidino]propoxy]imidazo[1,2-b]pyridazin-2-yl]-2-methylpropionate 0.5 fumarate 334 mg of 4-(diphenylmethoxy)-1-piperidinepropanol was dissolved in 20 ml of N,N-dimethylformamide; 45 mg of a 60% dispersion of sodium hydride in mineral oil was added, followed by stirring at room temperature under reduced pressure for 35 minutes. 310 mg of ethyl 2-[3,6-dichloroimidazo[1,2-b]pyridazin-2-yl]-2-methylpropionate was then added, followed by stirring at 0° C. for 2 hours. Ice water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate. The desired fraction was collected; the crystal precipitated was dissolved in 5 ml of ethanol; 160 mg of fumaric acid was added, followed by concentration under reduced pressure. Ethyl acetate was added to the residue; the mixture was washed with aqueous sodium bicarbonate and saturated saline, dried with magnesium sulfate and concentrated under reduced pressure. Ethyl acetate was added to the residue to cause crystallization; the crystal precipitated was collected by filtration, washed with ethyl ether and dried to yield 168 mg of the title compound.

Melting point: 186–188° C.

Elemental analysis (for $C_{35}H_{41}N_4O_6Cl.0.5H_2O$):

Calculated (%): C, 63.87; H, 6.43; N, 8.51

Found (%): C, 63.33; H, 6.34; N, 8.85

EXAMPLE 82

Production of ethyl 2-[3-chloro-6-[3-[4-(diphenylmethyl) piperazino]propoxy]imidazo[1,2-b]pyridazin-2-yl]-2-methylpropionate dihydrochloride 1.0 g of 4-(diphenylmethyl)-1-piperazinepropanol was dissolved in 10 ml of N,N-dimethylformamide; 142 mg of a 60% dispersion of sodium hydride in mineral oil was added, followed by stirring at room temperature under reduced pressure for 40 minutes. To the reaction mixture, 973 mg of ethyl 2-(3,6-dichloroimidazo[1,2-b]pyridazin-2-yl)-2-methylpropionate was added, followed by stirring at 0° C. for 2 hours. Ice water was added, followed by extraction with ethyl acetate; the extract was washed with saturated saline and dried with magnesium sulfate. The dry product was concentrated under reduced pressure; the residue was subjected to silica gel column chromatography and eluted with hexane:ethyl acetate:triethylamine (50:50:1). The desired fraction was collected and concentrated under reduced pressure; the crystal precipitated was dissolved in 5 ml of ethyl acetate; 1.01 ml of a 4 N hydrogen chloride solution in ethyl acetate acid was added, followed by concentration again. The residue was recrystallized from methanol, collected by filtration, washed with ethyl acetate and dried to yield 424 mg of the title compound.

Melting point: 203–205° C.

Elemental analysis (for $C_{32}H_{40}N_5O_3Cl_3.1.0H_2O$):

Calculated (%): C, 57.62; H, 6.35; N, 10.50

Found (%): C, 57.60; H, 6.37; N, 10.15

EXAMPLE 83

Production of ethyl 2-[3-chloro-6-[3-[4-(diphenylmethoxy)piperidino]propylamino]imidazo[1,2-b]pyridazin-2-yl]-2-methylpropionate dihydrochloride 2.56 g of 4-(diphenylmethoxy)-1-piperidinepropanamine and 1.19 g of ethyl 2-[3,6-dichloroimidazo[1,2-b]pyridazin-2-yl]-2-methylpropionate were stirred at 160° C. for 3 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected and dissolved in 5 ml of ethyl acetate; 0.80 ml of a 4 N hydrogen chloride solution in ethyl acetate was added, followed by concentration. The residue was powdered by the addition of ether and dried to yield 1.33 g of the title compound.

Noncrystalline

Elemental analysis (for $C_{33}H_{42}N_5O_3Cl_3.0.5H_2O$):

Calculated (%): C, 58.97; H, 6.45; N, 10.42

Found (%): C, 58.98; H, 6.64; N, 10.42

EXAMPLE 84

Production of ethyl 2-[3-chloro-6-[3-[4-(diphenylmethyl)piperazino]propylamino]imidazo[1,2-b]pyridazin-2-yl]-2-methylpropionate trihydrochloride 1.75 g of 4-(diphenylmethyl)-1-piperazinepropanamine and 854 mg of ethyl 2-[3,6-dichloroimidazo[1,2-b]pyridazin-2-yl]-2-methylpropionate were stirred at 160° C. for 4 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol (30:1). The desired fraction was collected, concentrated under reduced pressure and dissolved in 5 ml of ethyl acetate; 1.55 ml of a 4 N solution of hydrogen chloride in ethyl acetate was added, followed by concentration again. The crystal precipitated was washed by the addition of ethanol-ethyl acetate (1:3), collected by filtration and dried to yield 628 mg of the title compound.

Melting point: 203–205° C.

Elemental analysis (for $C_{32}H_{42}N_6O_2Cl_4.1.0H_2O$):

Calculated (%): C, 54.71; H, 6.31; N, 11.96

Found (%): C, 54.88; H, 6.07; N, 11.97

EXAMPLE 85

Production of 2-[3-chloro-6-[3-[4-(diphenylmethyl)piperazino]propylamino]imidazo[1,2-b]pyridazin-2-yl]-2-methylpropionic acid 633 mg of ethyl 2-[3-chloro-6-[3-[4-(diphenylmethyl)piperazino]propylamino]imidazo[1,2-b]pyridazin-2-yl]-2-methylpropionate trihydrochloride was dissolved in 6 ml of ethanol; 2.31 ml of a 2 N aqueous solution of sodium hydroxide was added, followed by thermal refluxing for 1.5 hours. After cooling, the mixture was concentrated under reduced pressure; the residue was diluted with water and washed with ethyl acetate; the water layer was ajusted to pH 5 by the addition of 1 N hydrochloric acid. Methanol was added; the crystal precipitated was collected by filtration, washed with water-ethyl acetate and dried to yield 462 mg of the title compound.

Melting point: 184–186° C.

Elemental analysis (for $C_{30}H_{35}N_6O_2Cl.1.0H_2O$):

Calculated (%): C, 63.76; H, 6.60; N, 14.87

Found (%): C, 63.49; H, 6.52; N, 14.81

EXAMPLE 86

Production of 2-[6-[2-[4-(diphenylmethyl)piperazino]ethylamino]imidazo[1,2-b]pyridazin-2-yl]-2-methylpropionic acid Process A: Production of isopropyl 2-[6-[2-[4-diphenylmethyl)piperazino]ethylamino]imidazo[1,2-b]pyridazin-2-yl]-2-methylpropionate 1.24 g of isopropyl 2-[6-[2-(methanesulfonyloxy)ethylamino]imidazo[1,2-b]pyridazin-2-yl]-2-methylpropionate was dissolved in 15 ml of N,N-dimethylformamide; 977 mg of 1-(diphenylmethyl)piperazine, 642 mg of potassium iodide and 535 mg of potassium carbonate were added, followed by stirring at room temperature for 1 hour and at 60° C. for 1.5 hours. Ice water and sodium chloride were added, followed by extraction with ethyl acetate; the extract was washed with saturated saline and dried with magnesium sulfate. The dry product was concentrated under reduced pressure; the residue was subjected to silica gel column chromatography and eluted with ethyl acetate. The desired fraction was collected, concentrated under reduced pressure and dried to yield 570 mg of the title compound.

$^1$H-NMR (CDCl$_3$) δ ppm: 1.17 (3H, S), 1.20 (3H, s), 1.62 (6H, s), 2.36–2.60 (8H, m), 2.63 (2H, t, J=5.8 Hz), 3.37 (2H, dt, J=5.6, 5.8 Hz), 4.24 (1H, s), 4.37 (1H), 4.90–5.10 (1H, m), 6.38 (1H, d, J=9.6 Hz), 7.13–7.44 (10H, m), 7.52 (1H, s), 7.55 (1H, d, J=9.4 Hz).

Process B 565 mg of isopropyl 2-[6-[2-[4-(diphenylmethyl) piperazino]ethylamino]imidazo[1,2-b]pyridazin-2-yl]-2-methylpropionate was dissolved in 4 ml of ethanol; 2.09 ml of a 1 N aqueous solution of sodium hydroxide was added, followed by thermal refluxing for 19 hours. After cooling, the mixture was concentrated under reduced pressure; the residue was diluted with water and ajusted to pH 5 by the addition of 1 N hydrochloric acid. Ethyl acetate was added; the crystal precipitated was collected, washed with water and methanol and recrystallized from N,N-dimethylformamide-ethyl acetate (5:1), collected by filtration, washed with ethyl acetate and dried to yield 249 mg of the title compound.

Melting point: 192–194° C.
Elemental analysis (for $C_{29}H_{34}N_6O_2 \cdot 3.0H_2O$):
Calculated (%): C, 63.02; H, 7.30; N, 15.21
Found (%): C, 62.99; H, 6.72; N, 15.01

EXAMPLE 87

Production of 2-[3-chloro-6-[3-[4-(diphenylmethoxy) piperidino]propylamino]imidazo [1,2-b]pyridazin-2-yl]-2-methylpropionic acid 653 mg of ethyl 2-[3-chloro-6-[3-[4-(diphenylmethoxy) piperidino]propylamino]imidazo[1,2-b]pyridazin-2-yl]-2-methylpropionate dihydrochloride was dissolved in 6 ml of ethanol; 1.97 ml of a 2 N aqueous solution of sodium hydroxide was added, followed by thermal refluxing for 2.5 hours. After cooling, the mixture was concentrated under reduced pressure; the residue was diluted with water and washed with ethyl acetate; the water layer was ajusted to pH 4.5 by the addition of 1 N hydrochloric acid. Acetone was added; the crystal precipitated was collected by filtration, washed with water-acetone (5:1) and dried to yield 465 mg of the title compound.

Melting point: 133–135° C.
Elemental analysis (for $C_{31}H_{36}N_6O_3Cl \cdot 1.0H_2O$):
Calculated (%): C, 64.18; H, 6.60; N, 12.07
Found (%): C, 64.16; H, 6.64; N, 12.33

EXAMPLE 88

Production of 2-[3-chloro-6-[3-[4-(diphenylmethyl) piperazino]propoxy]imidazo[1,2-b]pyridazin-2-yl]-2-methylpropionic acid 458 mg of ethyl 2-[3-chloro-6-[3-[4-(diphenylmethyl) piperazino]propoxy]imidazo[1,2-b]pyridazin-2-yl]-2-methylpropionate trihydrochloride was dissolved in 4 ml of 2-propanol; 1.34 ml of a 2 N aqueous solution of sodium hydroxide was added, followed by stirring at 80° C. for 1.5 hours, after which 0.3 ml of a 2 N aqueous solution of sodium hydroxide was added, followed by thermal refluxing for 2 hours. After cooling, the mixture was concentrated under reduced pressure; the residue was diluted with water and washed with ethyl acetate; the water layer was ajusted to pH 4 by the addition of 1 N hydrochloric acid, followed by extraction with ethyl acetate; the extract was dried with sodium sulfate. The dry product was concentrated under reduced pressure and crystallized by the addition of ethyl acetate-ethyl ether-hexane (2:5:1), collected by filtration, washed with ethyl ether and dried to yield 125 mg of the title compound.

Melting point: 118–121° C.
Elemental analysis (for $C_{30}H_{34}N_5O_3Cl \cdot 1.5H_2O$):
Calculated (%): C, 62.65; H, 6.48; N, 12.18
Found (%): C, 62.95; H, 6.47; N, 11.76

EXAMPLE 89

Production of 2-[6-[3-[4-(diphenylmethoxy) piperidino] propoxy]-7-methylimidazo[1,2-b] pyridazin-2-yl]-2-methylpropionic acid To 10 ml of N,N-dimethylformamide, 0.16 g of a 60% dispersion of sodium hydride in mineral oil and 1.30 g of 4-(diphenylmethoxy)-1-piperidinepropanol were added, followed by stirring at room temperature under reduced pressure for 1 hour. While the reaction mixture was cooled with ice water, 1.31 g of isopropyl 2-(6-chloro-7methylimidazo [1,2-b]pyridazin-2-yl)-2-methylpropionate was added, followed by stirring at room temperature for 1.5 hours. To the reaction mixture, ice water was added, followed by extraction with ethyl acetate; the extract was washed with saline and dried with magnesium sulfate. The dry product was concentrated under reduced pressure; the residue was subjected to silica gel column chromatography and eluted with hexane:ethyl acetate (1:5). The desired fraction was collected to yield 582 mg of isopropyl 2-[6-[3-[4-(diphenylmethoxy)piperidino]propoxy]-7-methylimidazo [1,2-b]pyridazin-2-yl]-2-methylpropionate as an oily substance. This oily substance was dissolved in 4 ml of ethanol; 2 ml of a 1 N aqueous solution of sodium hydroxide was added and reaction mixture was heated under reflux for 7 hours. After cooling, reaction mixture was concentrated under reduced pressure followed by extraction with ethyl acetate-tetrahydrofuran (1:1); the extract was washed with saturated saline and dried with magnesium sulfate. The dry product was concentrated under reduced pressure; the residue was crystallized by the addition of a small amount of water and ethyl ether, collected by filtration, washed with ethyl ether and dried to yield 0.413 g of the title compound.

Melting point: 122° C.
Elemental analysis (for $C_{32}H_{38}N_4O_4 \cdot 1.5H_2O$):
Calculated (%): C, 67.47; H, 7.25; N, 9.83
Found (%): C, 67.61; H, 7.13; N, 9.68

EXAMPLE 90

Production of 2-[6-[3-[4-(diphenylmethoxy) piperidino] propylamino]-7-methylimidazo[1,2-b] pyridazin-2-yl]-2-methylpropionic acid dihydrochloride 1.40 g of 4-(diphenylmethoxy)-1-piperidinepropanamine and 0.636 g of isopropyl 2-(6-chloro-7-methylimidazo[1,2-b]pyridazin-2-yl)-2-methylpropionate were stirred at 190–200° C. for 3 hours. After cooling, aqueous sodium bicarbonate was added, followed by extraction with ethyl acetate; the extract was washed with saline and dried with magnesium sulfate. The dry product was concentrated under reduced pressure; the residue was subjected to silica gel column chromatography and eluted with ethyl acetate-:methanol:triethylamine (185:15:2). The desired fraction was collected to yield 0.737 g of isopropyl 2-[6-[3-[4-(diphenylmethoxy)piperidino]propylamino]-7-methylimidazo[1,2-b]pyridazin-2-yl]-2-methylpropionate as an oily substance. This oily substance was dissolved in 6 ml of ethanol; 3.15 ml of a 1 N aqueous solution of sodium hydroxide was added, followed by thermal refluxing for 7 hours. After cooling, the mixture was concentrated under reduced pressure; under ice cooling conditions, 1.89 ml of 1 N hydrochloric acid was added; the residue was washed with ethyl acetate. To the water layer, 1.89 ml of 1 N hydrochloric acid was added to saturate with sodium chloride, followed by extraction with ethyl acetate-tetrahydrofuran (1:1); the extract was washed with saturated saline and dried with magnesium sulfate. The dry product was concentrated under reduced pressure; 1.89 ml of 1 N hydrochloric acid was added to the residue, followed by concentration to dryness under reduced pressure; the residue was crystallized by the addition of ethyl ether, collected by filtration, washed with ethyl ether and dried to yield 0.445 g of the title compound.

Melting point: 202° C. (decomposed)

Elemental analysis (for $C_{32}H_{41}N_5O_3 \cdot 0.5H_2O$):

Calculated (%): C, 61.63; H, 6.79; N, 11.23

Found (%): C, 61.66; H, 6.83; N, 11.11

EXAMPLE 91

Production of pivaloyloxymethyl 2-[6-[3-(4-diphenylmethoxy)piperidino]propylamino]imidazo[1,2-b]pyridazin-2-yl]-2-methylpropionate difumarate 1.36 g of ethyl 2-[6-[3-(4-diphenylmethoxy)piperidino]propylamino]imidazo[1,2-b]pyridazin-2-yl]-2-methylpropionate difumarate was suspended in 20 ml of ethyl acetate and washed with aqueous sodium bicarbonate; the ethyl acetate layer was dried with magnesium sulfate. The dry product was concentrated under reduced pressure; the residue was dissolved in 8 ml of ethanol; 4.3 ml of a 1 N aqueous solution of sodium hydroxide was added, followed by stirring at room temperature for 40 hours. The mixture was concentrated under reduced pressure; while the residue was cooled with ice, 4.3 ml of 1 N hydrochloric acid and saline were added, followed by extraction with ethyl acetate-tetrahydrofuran (1:1); the extract was washed with saturated saline and dried with magnesium sulfate. The dry product was concentrated under reduced pressure; the residue was dissolved in 5 ml of N,N-dimethylformamide; 0.374 ml of chloromethyl pivalate and 0.357 g of potassium carbonate were added, followed by stirring at room temperature for 20 hours. Ice water was added, followed by extraction with ethyl acetate; the extract was washed with saline and dried with magnesium sulfate. The dry product was concentrated under reduced pressure; the residue was subjected to silica gel column chromatography and eluted with ethyl acetate:methanol:triethylamine (185:15:2). The desired fraction was collected, dissolved in 10 ml of ethyl acetate; a solution of 227 mg of fumaric acid in 5 ml of methanol was added, followed by concentration. The residue was recrystallized from ethyl acetate to yield 0.772 g of the title compound.

Melting point: 164–167° C.

Elemental analysis (for $C_{45}H_{55}N_5O_{13}$):

Calculated (%): C, 61.84; H, 6.34; N, 8.01

Found (%): C, 61.83; H, 6.30; N, 8.10

EXAMPLE 92

Production of ethyl 2-[6-[4-[4-(diphenylmethoxy)piperidino]butyl]imidazo[1,2-b]pyridazin-2-yl]-2-methylpropionate dihydrochloride Process A: Production of ethyl 2-[6-(4-chlorobutyl)imidazo[1,2-b]pyridazin-2-yl]-2-methylpropionate 5.0 g of 1-chloro-4-iodobutane was dissolved in 50–5 ml of toluene-N,N-dimethylacetamide; 2.24 g of copper-activated zinc was added, followed by stirring at 80° C. in a nitrogen atmosphere for 3.5 hours. After cooling, 3.06 g of ethyl 2-(6-chloroimidazo[1,2-b]pyridazin-2-yl]-2-methylpropionate and 160 mg of dichlorobis(triphenylphosphine)palladium (II) were added, followed by stirring at 80° C. for 4 hours. After cooling, water and ethyl acetate were added; the insoluble substances were filtered off through Celite; after the water layer was separated, the organic layer was washed with saturated saline and dried with magnesium sulfate. The dry product was concentrated under reduced pressure; the residue was subjected to silica gel column chromatography and eluted with hexane:ethyl acetate (1:1). The desired fraction was collected, concentrated under reduced pressure and dried to yield 1.74 g of the title compound.

$^1$H-NMR (CDCl$_3$) δ ppm: 1.23 (3H, t, J=6.8 Hz), 1.68 (6H, s), 1.80–2.00 (4H, m), 2.84 (2H, t, J=7.2 Hz), 3.59 (2H, t, J=6.0 Hz), 4.17 (2H, q, J=7.1 Hz), 6.89 (1H, d, J=9.5 Hz), 7.80 (1H, s), 7.82 (1H, d, J=9.2 Hz).

Process B 828 mg of ethyl 2-[6-(4-chlorobutyl)imidazo[1,2-b]pyridazin-2-yl]-2-methylpropionate was dissolved in 10 ml of acetonitrile; 752 mg of 4-(diphenylmethoxy)piperidine, 552 mg of potassium iodide and 460 mg of potassium carbonate were added, followed by stirring at 60° C. for 4 hours, after which the mixture was thermally refluxed for 18 hours. After cooling, ice water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:2.5:1). The desired fraction was collected, concentrated under reduced pressure, dissolved in 5 ml of ethyl acetate; 1.01 ml of a 4 N solution of hydrogen chloride in ethyl acetate was added, followed by concentration under reduced pressure. The residue was powdered from ethyl ether, collected by filtration and dried to yield 1.18 g of the title compound.

Noncrystalline

Elemental analysis (for $C_{34}H_{44}N_4O_3Cl_2 \cdot 1.0H_2O$):

Calculated (%): C, 63.25; H, 7.18; N, 8.68

Found (%): C, 63.10; H, 7.43; N, 8.64

EXAMPLE 93

Production of sodium 2-[6-[4-[4-(diphenylmethoxy)piperidino]butyl]imidazo[1,2-b]pyridazin-2-yl]-2-methylpropionate 631 mg of ethyl 2-[6-[4-[4-(diphenylmethoxy)piperidino]butyl]imidazo[1,2-b]pyridazin-2-yl]-2-methylpropionate dihydrochloride was dissolved in 4 ml of ethanol; 5.5 ml of a 1 N aqueous solution of sodium hydroxide was added, followed by thermal refluxing for 3 hours. After cooling, the mixture was concentrated under reduced pressure; the residue was diluted with water and ajusted to pH 5.5 by the addition of 1 N hydrochloric acid. Acetone was added to cause crystallization; the crystal precipitated was washed with water-acetone (2:1) and dried to yield 345 mg of the title compound.

Melting point: 177–179° C.

Elemental analysis (for $C_{32}H_{37}N_4O_3Na \cdot 1.75H_2O$):

Calculated (%): C, 66.25; H, 7.04; N, 9.66

Found (%): C, 66.13; H, 6.93; N, 9.81

EXAMPLE 94

Production of ethyl 2-[6-[4-[4-(diphenylmethyl)piperazino] butyl]imidazo[1,2-b]pyridazin-2-yl]-2-methylpropionate 921 mg of ethyl 2-[6-(4-chlorobutyl)imidazo[1,2-b]pyridazin-2-yl]-2-methylpropionate was dissolved in 10 ml of N,N-dimethylformamide; 789 mg of 1-(diphenylmethyl) piperazine, 433 mg of potassium iodide and 520 mg of potassium carbonate were added, followed by stirring at 60° C. for 5 hours. After cooling, ethyl acetate was added; the mixture was washed with saturated saline and dried with magnesium sulfate. The dry product was concentrated under reduced pressure; the residue was subjected to silica gel column chromatography and eluted with ethyl acetate:triethylamine (50:1). The desired fraction was collected, concentrated under reduced pressure and crystallized from ethyl ether-hexane (1:1), collected by filtration, washed with hexane and dried to yield 554 mg of the title compound.

Melting point: 105–106° C.

Elemental analysis (for $C_{33}H_{41}N_5O_2 \cdot 0.5H_2O$):

Calculated (%): C, 72.23; H, 7.71; N, 12.76

Found (%): C, 72.48; H, 7.73; N, 12.95

EXAMPLE 95

Production of 2-[6-[4-[4-(diphenylmethyl) piperazino]butyl] imidazo[1,2-b]pyridazin-2-yl]-2-methylpropionic acid 482 mg of ethyl 2-[6-[4-[4-(diphenylmethyl)piperazino]butyl]imidazo[1,2-b]pyridazin-2-yl]-2-methylpropionate was dissolved in 2 ml of ethanol; 1.8 ml of a 1 N aqueous solution of sodium hydroxide was added, followed by thermal refluxing for 1 hour. After cooling, the mixture was concentrated under reduced pressure; the residue was diluted with water and ajusted to pH 5 by the addition of 1 N hydrochloric acid. Ethyl acetate was added to cause crystallization; the crystal precipitated was washed with water-acetone (2:1) and dried to yield 386 mg of the title compound.

Melting point: 108–110° C.

Elemental analysis (for $C_{31}H_{37}N_5O_2 \cdot 1.0H_2O$):

Calculated (%): C, 70.30; H, 7.42; N, 13.22

Found (%): C, 70.22; H, 7.73; N, 13.32

EXAMPLE 96

Production of isopropyl 1-[6-[3-[4-(diphenylmethoxy)piperidino]propylamino]imidazo[1,2-b]pyridazin-2-yl]cyclopentanecarboxylate dihydrochloride 1.67 g of 4-(diphenylmethoxy)-1-piperidinepropaneamine and 793 mg of isopropyl 1-(6-chloroimidazo[1,2-b]pyridazin-2-yl] cyclopentanecarboxylate were stirred at 165° C. for 5.5 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (100:5:2). The desired fraction was collected, concentrated under reduced pressure and dissolved in 5 ml of ethyl acetate; 0.84 ml of a 4 N solution of hydrogen chloride in ethyl acetate was added, followed by concentration. The residue was powdered by the addition of ethyl ether; the resulting powder was collected by filtration, washed with ethyl ether and dried to yield 999 mg of the title compound.

Noncrystalline

Elemental analysis (for $C_{36}H_{47}N_5O_3Cl_2 \cdot 0.5H_2O \cdot 0.5Et_2O$):

Calculated (%): C, 63.85; H, 7.47; N, 9.80

Found (%): C, 63.83; H, 7.54; N, 9.83

EXAMPLE 97

Production of 1-[6-[3-[4-(diphenylmethoxy) piperidino] propylamino]imidazo[1,2-b]pyridazin-2-yl]cyclopentanecarboxylic acid 598 mg of isopropyl 1-[6-[3-[4-(diphenylmethoxy)piperidino]propylamino]imidazo[1,2-b]pyridazin-2-yl] cyclopentanecarboxylate dihydrochloride was dissolved in 3 ml of ethanol; 2.24 ml of a 2 N aqueous solution of sodium hydroxide was added, followed by thermal refluxing for 7 hours. After cooling, the mixture was concentrated under reduced pressure; the residue was diluted with water, washed with ethyl acetate and ajusted to pH 4.5 by the addition of 1 N hydrochloric acid. The mixture was saturated with sodium chloride and extracted with ethyl acetate-tetrahydrofuran (1:2); the extract was dried with magnesium sulfate. The dry product was concentrated under reduced pressure, powdered by the addition of ethyl acetate-ethyl ether (1:1), washed with ethyl ether and dried to yield 349 mg of the title compound.

Noncrystalline

Elemental analysis (for $C_{33}H_{39}N_5O_3 \cdot 3.0H_2O$);

Calculated (%): C, 65.22; H, 7.46; N, 11.52

Found (%): C, 65.19; H, 7.17; N, 11.29

EXAMPLE 98

Production of 1-[6-[3-[4-(diphenylmethoxy) piperidino] propoxy]imidazo[1,2-b]pyridazin-2-yl] cyclopropanecarboxylic acid Process A: Production of isopropyl 1-[6-[3-[4-(diphenylmethoxy)piperidino]propoxy]imidazo[1,2-b]pyridazin-2-yl]cyclopropanecarboxylate 1.14 g of 4-(diphenylmethoxy)-1-piperidinepropanol was dissolved in 15 ml of N,N-dimethylacetamide; 140 mg of a 60% dispersion of sodium hydride in mineral oil was added, followed by stirring at room temperature under reduced pressure for 30 minutes. To the reaction mixture, 980 mg of isopropyl 1-(6-chloroimidazo[1,2-b]pyridazin-2-yl) cyclopropanecarboxylate was added under ice cooling conditions, followed by stirring at constant temperature for 4 hours. Ice water was added, followed by saturation with sodium chloride and subsequent extraction with ethyl acetate-tetrahydrofuran (1:1); the extract was dried with magnesium sulfate. The dry product was concentrated under reduced pressure; the residue was subjected to silica gel column chromatography and eluted with ethyl acetate. The desired fraction was collected and concentrated under reduced pressure to yield 496 mg of the title compound.

$^1$H-NMR (CDCl$_3$) δ ppm: 1.25 (3H, s), 1.28 (3H, s), 1.40–2.25 (12H, m), 2.43–2.55 (2H, m), 2.70–2.88 (2H, s), 3.36–3.55 (1H, m), 4.33 (2H, t, J=6.3 Hz), 4.98–5.18 (1H, m), 5.52 (1H, s), 6.58 (1H, d, J=9.8 Hz), 7.15–7.40 (10H, m), 7.64 (1H, d, J=9.4 Hz), 8.03 (1H, s).

Process B 490 mg of isopropyl 1-[6-[3-[4-(diphenylmethoxy) piperidino]propoxy]imidazo[1,2-b]pyridazin-2-yl] cyclopropanecarboxylate was dissolved in 2 ml of ethanol; 0.86 ml of a 2 N aqueous solution of sodium hydroxide was added, followed by thermal refluxing for 2 hours. After cooling, the mixture was concentrated under reduced pressure; the residue was diluted with water and ajusted to pH 5 by the addition of 1 N hydrochloric acid. The mixture was extracted with ethyl acetate-tetrahydrofuran (1:3); the extract was washed with saline and dried with magnesium sulfate. The dry product was concentrated under reduced pressure, powdered by the addition of ethyl ether, washed with ethyl ether and dried to yield 382 mg of the title compound.

Noncrystalline
Elemental analysis (for $C_{31}H_{34}N_4O_4 \cdot 2.0H_2O$):
Calculated (%): C, 66.17; H, 6.81; N, 9.96
Found (%): C, 66.27; H, 7.00; N, 9.75

EXAMPLE 99

Production of isopropyl 1-[6-[3-[4-(diphenylmethoxy)piperidino]propylamino]imidazo[1,2-b]pyridazin-2-yl]cyclopropanecarboxylate dihydrochloride 2.72 g of 4-(diphenylmethoxy)-1-piperidinepropanamine and 1.27 g of isopropyl 1-(6-chloroimidazo[1,2-b]pyridazin-2-yl]cyclopropanecarboxylate were stirred at 165° C. for 4.5 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected, concentrated under reduced pressure and dissolved in 5 ml of ethyl acetate; 0.72 ml of a 4 N solution of hydrogen chloride in ethyl acetate was added, followed by concentration again. The residue was crystallized by the addition of ethyl acetate-acetone (2:1), collected by filtration, washed with ethyl acetate and dried to yield 714 mg of the title compound.

Melting point: 206–208° C.
Elemental analysis (for $C_{34}H_{43}N_5O_3Cl_2 \cdot 0.5H_2O$):
Calculated (%): C, 62.86; H, 6.83; N, 10.78
Found (%): C, 63.10; H, 6.88; N, 10.83

EXAMPLE 100

Production of 1-[6-[3-[4-(diphenylmethoxy)piperidino] propylamino]imidazo[1,2-b]pyridazin-2-yl]cyclopropanecarboxylic acid 554 mg of isopropyl 1-[6-[3-[4-(diphenylmethoxy)piperidino]propylamino]imidazo[1,2-b]pyridazin-2-yl]cyclopropanecarboxylate dihydrochloride was dissolved in 3 ml of ethanol; 1.73 ml of a 2 N aqueous solution of sodium hydroxide was added, followed by thermal refluxing for 1.5 hours. After cooling, the mixture was concentrated under reduced pressure; the residue was diluted with water, washed with ethyl acetate and ajusted to pH 5.5 by the addition of 1 N hydrochloric acid. The mixture was crystallized by the addition of acetone, washed with acetone and dried to yield 321 mg of the title compound.

Melting point: 115–117° C.
Elemental analysis (for $C_{31}H_{35}N_5O_3 \cdot 1.0H_2O$):
Calculated (%): C, 68.49; H, 6.86; N, 12.88
Found (%): C, 68.24; H, 6.89; N, 12.93

EXAMPLE 101

Production of ethyl 2-[6-[3-[4-(diphenylmethoxy)piperidino] propyl]imidazo[1,2-b]pyridazin-2-yl]-2-methylpropionate dihydrochloride Process A: Production of ethyl 2-[6-[3-(tetrahydropyranyl-2-oxy)propyl]imidazo[1,2-b]pyridazin-2-yl]-2-methylpropionate 10.6 g of 2-(3-iodopropoxy)tetrahydropyrane was dissolved in 106–10.6 ml of toluene-N,N-dimethylacetamide; 3.87 g of copper-activated zinc was added, followed by stirring at 80° C. in a nitrogen atmosphere for 3 hours. After cooling, 5.28 g of ethyl 2-(6-chloroimidazo[1,2-b]pyridazin-2-yl]-2-methylpropionate and 277 mg of dichlorobis (triphenylphosphine)palladium (II) were added, followed by stirring at 80° C. for 14 hours. After cooling, ice water and ethyl acetate were added; the insoluble substances were filtered off through Celite; after the filtrate was extracted with ethyl acetate, the extract was washed with saturated saline and dried with magnesium sulfate. The dry product was concentrated under reduced pressure; the residue was subjected to silica gel column chromatography and eluted with hexane:ethyl acetate (1:1). The desired fraction was collected, concentrated under reduced pressure and dried to yield 2.64 g of the title compound.

$^1$H-NMR (CDCl$_3$) δ ppm: 1.23 (3H, t, J=7.0 Hz), 1.68 (6H, s), 1.40–1.95 (6H, m), 1.98–2.15 (2H, m), 2.87–2.96 (2H, m), 3.40–3.56 (2H, m), 3.75–3.94 (2H, m), 4.17 (2H, q, J=7.1 Hz), 4.54–4.62 (1H, broad t), 6.91 (1H, d, J=9.2 Hz), 7.79 (1H, s), 7.80 (1H, d, J=9.0 Hz).

Process B: Production of ethyl 2-[6-[3-(tetrahydropyranyl-2-oxy)propyl]imidazo[1,2-b]pyridazin-2-yl]-2-methylpropionate 3.67 g of ethyl 2-[6-[3-(tetrahydropyranyl-2-oxy)propyl] imidazo[1,2-b]pyridazin-2-yl]-2-methylpropionate was dissolved in 38 ml of ethanol; 2.40 g of p-toluenesulfonic acid monohydrate was added, followed by stirring at room temperature for 24 hours. After the ethanol was distilled off under reduced pressure, the residue was diluted with water and extracted with ethyl acetate and tetrahydrofuran. The extract was washed with saturated saline and dried with magnesium sulfate. The dry product was concentrated under reduced pressure; the residue was subjected to silica gel column chromatography and eluted with ethyl acetate. The desired fraction was collected, concentrated under reduced pressure and dried to yield 2.05 g of the title compound.

$^1$H-NMR (CDCl$_3$) δ ppm: 1.23 (3H, t, J=7.2 Hz), 1.68 (6H, s), 1.95–2.10 (2H, m), 2.94 (2H, t, J=7.5 Hz), 3.74 (2H, q, J=7.1 Hz), 4.17 (2H, q, J=7.1 Hz), 6.91 (1H, d, J=9.0 Hz), 7.80 (1H, s), 7.82 (1H, d, J=9.2 Hz).

Process C: Production of ethyl 2-[6-[3-(methanesulfonyloxy)propyl]imidazo[1,2-b]pyridazin-2-yl]-2-methylpropionate 2.04 g of ethyl 2-[6-(3-hydroxypropyl)imidazo[1,2-b]pyridazin-2-yl]-2-methylpropionate was suspended in 40 ml of tetrahydrofuran; under ice cooling conditions, 2.41 ml of N-ethyldiisopropylamine and 0.83 ml of methanesulfonyl chloride were added, followed by stirring at room temperature for 15 minutes. Ice water was added, followed by extraction with ethyl acetate; the extract was washed with saturated saline and dried with magnesium sulfate. The dry product was concentrated under reduced pressure and dried to yield 2.78 g of the title compound.

$^1$H-NMR (CDCl$_3$) δ ppm: 1.23 (3H, t, J=7.1 Hz), 1.68 (6H, s), 2.15–2.35 (2H, m), 2.97 (2H, t, J=7.5 Hz), 3.03 (3H, s), 4.17 (2H, q, J=7.4 Hz), 4.34 (2H, t, J=6.2 Hz), 6.89 (1H, d, J=9.2 Hz), 7.80 (1H, s), 7.84 (1H, d, J=10 Hz).

Process D 1.32 g of ethyl 2-[6-[3-(methanesulfonyloxy)propyl] imidazo[1,2-b]pyridazin-2-yl]-2-methylpropionate was dissolved in 15 ml of N,N-dimethylformamide; 1.15 g of 4-(diphenylmethoxy)piperidine, 712 mg of potassium iodide and 593 mg of potassium carbonate were added, followed by stirring at 60° C. for 2 hours. After cooling, ice water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1); the desired fraction was collected, concentrated under reduced pressure, dissolved in 5 ml of ethyl acetate; 1.6 ml of a 4 N solution of hydrogen chloride in ethyl acetate was added, followed by concentration under reduced pressure. The concentrate was powdered from ethyl ether, collected by filtration and dried to yield 1.55 g of the title compound.

Noncrystalline

Elemental analysis (for $C_{33}H_{42}N_4O_3Cl_2 \cdot 0.5H_2O$):

Calculated (%): C, 63.66; H, 6.96; N, 9.00

Found (%): C, 63.61; H, 6.94; N, 9.07

EXAMPLE 102

Production of 2-[6-[3-[4-(diphenylmethoxy) piperidino]propyl]imidazo[1,2-b]pyridazin-2-yl]-2-methylpropionic acid 905 mg of ethyl 2-[6-[3-[4-(diphenylmethoxy) piperidino]propyl]imidazo[1,2-b]pyridazin-2-yl]-2-methylpropionate dihydrochloride was dissolved in 6 ml of ethanol; 5.9 ml of a 1 N aqueous solution of sodium hydroxide was added, followed by thermal refluxing for 2 hours. After cooling, the mixture was concentrated under reduced pressure; the residue was diluted with water and ajusted to pH 4.5 by the addition of 1 N hydrochloric acid. The mixture was crystallized by the addition of acetone, washed with acetone and dried to yield 476 mg of the title compound.

Melting point: 195–205° C.

Elemental analysis (for $C_{31}H_{36}N_4O_3 \cdot 0.3H_2O$):

Calculated (%): C, 71.87; H, 7.12; N, 10.81

Found (%): C, 71.95; H, 6.94; N, 10.73

EXAMPLE 103

Production of ethyl 2-[6-[3-[4-(diphenylmethyl) piperazino]propyl]imidazo[1,2-b]pyridazin-2-yl]-2-methylpropionate trihydrochloride 1.41 g of ethyl 2-[6-[3-(methanesulfonyloxy)propyl] imidazo[1,2-b]pyridazin-2-yl]-2-methylpropionate was dissolved in 15 ml of N,N-dimethylformamide; 1.16 g of 1-(diphenylmethyl)piperazine, 1.16 g of potassium iodide and 760 mg of potassium carbonate were added, followed by stirring at 60° C. for 2 hours. Ice water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:triethylamine (50:1). The desired fraction was collected, concentrated under reduced pressure, dissolved in 5 ml of ethyl acetate; 2.4 ml of a 4 N solution of hydrogen chloride in ethyl acetate was added, followed by concentration again. The concentrate was recrystallized from acetone:ethyl acetate (1:1), collected by filtration and dried to yield 1.39 g of the title compound.

Melting point: 183–185° C.

Elemental analysis (for $C_{32}H_{42}N_5O_2Cl_3 \cdot 1.0H_2O$):

Calculated (%): C, 58.85; H, 6.79; N, 10.72

Found (%): C, 58.82; H, 6.52; N, 10.67

EXAMPLE 104

Production of 2-[6-[3-[4-(diphenylmethyl) piperazino]propyl]imidazo[1,2-b]pyridazin-2-yl]-2-methylpropionic acid 1.08 g of ethyl 2-[6-[3-[4-(diphenylmethyl)piperazino] propyl]imidazo[1,2-b]pyridazin-2-yl]-2-methylpropionate trihydrochloride was dissolved in 8 ml of ethanol; 8.5 ml of a 1 N aqueous solution of sodium hydroxide was added, followed by thermal refluxing for 2 hours. After cooling, the mixture was concentrated under reduced pressure; the residue was diluted with water and ajusted to pH 4.5 by the addition of 1 N hydrochloric acid. The mixture was crystallized by the addition of acetone, washed with water-acetone (2:1) and dried to yield 435 mg of the title compound.

Melting point: 176–178° C.

Elemental analysis (for $C_{30}H_{35}N_5O_2 \cdot 0.5H_2O$):

Calculated (%): C, 71.12; H, 7.16; N, 13.82

Found (%): C, 70.79; H, 6.86; N, 13.87

EXAMPLE 105

Production of ethyl 2-[6-[3-[4-(diphenylmethoxy) piperidino]propylamino]-3-methylimidazo[1,2-b] pyridazin-2-yl]-2-methylpropionate dihydrochloride 2.38 g of 4-(diphenylmethoxy)-1-piperidinepropanamine and 1.03 g of ethyl 2-(6-chloro-3-methylimidazo[1,2-b] pyridazin-2-yl)-2-methylpropionate were stirred at 160° C. for 7.5 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected, concentrated under reduced pressure and dissolved in 5 ml of ethyl acetate; 0.96 ml of a 4 N solution of hydrogen chloride in ethyl acetate was added, followed by concentration again. The residue was powdered by the addition of ethyl ether, collected by filtration and dried to yield 666 mg of the title compound.

Noncrystalline

Elemental analysis (for $C_{34}H_{45}N_5O_3Cl_2 \cdot 1.5H_2O$):

Calculated (%): C, 60.98; H, 7.22; N, 10.46

Found (%): C, 60.70; H, 6.95; N, 10.34

EXAMPLE 106

Production of ethyl [6-[3-[4-(diphenylmethoxy) piperidino]propylamino]-2-methylimidazo[1,2-b] pyridazin-3yl]carboxylate 1.98 g of 4-(diphenylmethoxy)-1-piperidinepropanamine and 1.46 g of ethyl (6-chloro-2-methylimidazo[1,2-b] pyridazin-3-yl]carboxylate were dissolved in 15 ml of 1-methyl-2-pyrrolidone; 1.05 ml of N-ethyldiisopropylamine was added, followed by stirring at 120° C. for 40 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected and concentrated; ethyl ether-hexane (1:2) was added to the residue; the crystal precipitated was collected by filtration, washed with hexane and dried to yield 412 mg of the title compound.

Melting point: 117–119° C.

Elemental analysis (for $C_{31}H_{37}N_5O_3$):

Calculated (%): C, 70.56; H, 7.07; N, 13.27
Found (%): C, 70.16; H, 6.93; N, 13.01

EXAMPLE 107

Production of [6-[3-[4-(diphenylmethoxy) piperidino]propylamino]-2-methylimidazo[1,2-b] pyridazin-2-yl]carboxylic acid 770 mg of ethyl [6-[3-[4-(diphenylmethoxy)piperidino] propylamino]-2-methylimidazo[1,2-b]pyridazin-3-yl] carboxylate was dissolved in 5 ml of ethanol; 3.2 ml of a 1 N aqueous solution of sodium,hydroxide was added, followed by stirring at room temperature for 3.5 hours. After cooling, the mixture was concentrated under reduced pressure; the residue was diluted with water, washed with ethyl acetate and ajusted to pH 4.5 by the addition of 1 N hydrochloric acid. The crystal precipitated was collected by filtration, washed with water and ethyl acetate and dried to yield 265 mg of the title compound.

Melting point: 101–103° C.
Elemental analysis (for $C_{29}H_{33}N_5O_3.0.5H_2O$ ):
Calculated (%): C, 68.48; H, 6.74; N, 13.77
Found (%): C, 68.63; H, 6.77; N, 13.91

EXAMPLE 108

Production of ethyl 2-[6-[3-[4-(diphenylmethylamino) piperidino]propylamino] imidazo[1,2-b]pyridazin-2-yl]-2-methylpropionate 3.12 g of 4-(diphenylmethylamino)-1-piperidinepropanamine and 1.72 g of ethyl 2-(6-chloroimidazo[1,2-b]pyridazin-2-yl)-2-methylpropionate were stirred at 180° C. for 3 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected and concentrated under reduced pressure; the residue was crystallized by the addition of ethyl ether-hexane (1:3), collected by filtration, washed with hexane and dried to yield 1.83 g of the title compound.

Melting point: 115–117° C.
Elemental analysis (for $C_{33}H_{42}N_6O_2$):
Calculated (%): C, 71.45; H, 7.63; N, 15.15
Found (%): C, 71.40; H, 7.70; N, 14.94

EXAMPLE 109

Production of 2-[6-[3-[4-(diphenylmethylamino) piperidino]propylamino]imidazo[1,2-b]pyridazin-2-yl]-2-methylpropionic acid 612 mg of ethyl 2-[6-[3-[4-(diphenylmethylamino) piperidino]propylamino]imidazo[1,2-b]pyridazin-2-yl]-2-methylpropionate was dissolved in 5 ml of ethanol; 2.2 ml of a 1 N aqueous solution of sodium hydroxide was added, followed by thermal refluxing for 6 hours. After cooling, the mixture was concentrated under reduced pressure; the residue was diluted with water, washed with ethyl acetate and ajusted to pH 5 by the addition of 1 N hydrochloric acid. The mixture was saturated with sodium chloride and extracted with tetrahydrofuran; the extract was dried with magnesium sulfate. The dry product was concentrated under reduced pressure, powdered by the addition of ethyl ether, collected by filtration and dried to yield 503 mg of the title compound.

Noncrystalline
Elemental analysis (for $C_{31}H_{38}N_6O_2.2.7H_2O.0.8Et_2O$):
Calculated (%): C, 64.93; H, 7.87; N, 13.28
Found (%): C, 64.99; H, 7.72; N, 12.85

EXAMPLE 110

Production of ethyl 2-[6-[3-[4-(diphenylmethoxy) piperidino]propylamino]imidazo[1,2-b]pyridazin-2-yl]-2-ethylbutyrate dihydrochloride 3.03 g of 4-(diphenylmethoxy)-1-piperidinepropanamine and 1.38 g of ethyl 2-(6-chloroimidazo[1,2-b]pyridazin-2-yl)-2-ethylbutyrate were stirred at 160° C. for 1.5 hours, then at 180° C. for 2 hours. After the mixture was cooled to 90° C., ethanol and aqueous sodium bicarbonate were added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:2.5:1). The desired fraction was collected, concentrated under reduced pressure and dissolved in 5 ml of ethyl acetate; 1.4 ml of a 4 N solution of hydrogen chloride in ethyl acetate was added, followed by concentration again. The residue was powdered by the addition of ethyl ether and dried to yield 893 mg of the title compound.

Noncrystalline
Elemental analysis (for $C_{35}H_{47}N_5O_3Cl_2.1.0Et_2O$ ):
Calculated (%): C, 64.10; H, 7.86; N, 9.58
Found (%): C, 63.78; H, 7.57; N, 9.96

EXAMPLE 111

Production of N-[3-chloro-6-[3-[4-(diphenylmethoxy)piperidino]propylamino]imidazo [1,2-b]pyridazine-2-carbonyl]glycine ethyl ester 0.649 g of 4-(diphenylmethoxy)-1-piperidinepropanamine and 0.53 g of N-(3,6-dichloroimidazo[1,2-b]pyridazine-2-carbonyl)glycine ethyl ester were dissolved in 7 ml of 1-methyl-2-pyrrolidone; 0.345 ml of N-ethyldiisopropylamine was added, followed by stirring in an oil bath (90–100° C.) for 24 hours. After cooling, ice water was added, followed by extraction with ethyl acetate; the extract was washed with saline and dried with magnesium sulfate. The dry product was concentrated under reduced pressure; the residue was subjected to silica gel column chromatography and eluted with ethyl acetate::methanol:triethylamine (185:15:2). The desired fraction was collected and recrystallized from ethyl acetate to yield 0.711 g of the title compound.

Melting point: 178–180° C.
Elemental analysis (for $C_{32}H_{37}N_6O_4Cl$):
Calculated (%): C, 63.51; H, 6.16; N, 13.89
Found (%): C, 63.56; H, 6.21; N, 13.78

EXAMPLE 112

Production of N-[6-[3-[4-(diphenylmethoxy) piperidino]propylamino]imidazo[1,2-b]pyridazine-2-carbonyl]-β-alanine ethyl ester 0.649 g of 4-(diphenylmethoxy)-1-piperidinepropanamine and 0.594 g of N-(6-chloroimidazo

[1,2-b]pyridazine-2-carbonyl)-β-alanine ethyl ester were dissolved in 7 ml of 1-methyl-2-pyrrolidone; 0.345 ml of N-ethyldiisopropylamine was added, followed by stirring in an oil bath (90–100° C.) for 24 hours. After cooling, ice water was added, followed by extraction with ethyl acetate; the extract was washed with saline and dried with magnesium sulfate. The dry product was concentrated under reduced pressure; the residue was subjected to silica gel column chromatography and eluted with ethyl acetate:methanol:triethylamine (370:30:4). The desired fraction was collected and recrystallized from ethyl ether to yield 0.347 g of the title compound.

Melting point: 83–86° C.
Elemental analysis (for $C_{33}H_{40}N_6O_4$):
Calculated (%): C, 67.79; H, 6.90; N, 14.37
Found (%): C, 68.05; H, 6.87; N, 14.38

EXAMPLE 113

Production of sodium 2-[6-[3-[4-(diphenylmethoxy) piperidino]propylamino]imidazo[1,2-b]pyridazin-2-yl]-2-methylpropionate To a solution of 2-[6-[3-[4-(diphenylmethoxy)piperidino]propylamino]imidazo[1,2-b]pyridazin-2-yl]-2-methylpropionic acid (528 mg) in methanol (2 ml), a 2 N aqueous solution of sodium hydroxide (0.47 ml) was added, followed by stirring at room temperature for 5 minutes. This solution was diluted with 2-propanol and concentrated under reduced pressure; the residue was dissolved in 2-propanol and again concentrated under reduced pressure. To this residue, 2-propanol and ethyl ether were added; the resulting powder was collected by filtration to yield the title compound (474 mg).

Noncrystalline
Elemental analysis (for $C_{31}H_{36}N_5O_3Na \cdot 0.5H_2O$):
Calculated (%): C, 66.65; H, 6.68; N, 12.54
Found (%): C, 66.45; H, 6.54; N, 12.53

EXAMPLE 114

Production of 6-[5-[4-(diphenylmethoxy)piperidino]pentylamino][1,2,4]triazolo[1,5-b]pyridazine 0.705 g of 4-(diphenylmethoxy)-1-piperidinepentanamine and 0.309 g of 6-chloro[1,2,4]triazolo[1,5-b]pyridazine were stirred at 135–140° C. for 1.5 hours. After cooling, aqueous sodium bicarbonate was added, followed by extraction with ethyl acetate; the extract was washed with saline and dried with sodium sulfate. The dry product was concentrated under reduced pressure; the residue was subjected to silica gel column chromatography and eluted with ethyl acetate:methanol:triethylamine (95:5:1). The desired fraction was collected, recrystallized from ethyl ether and dried to yield 0.629 g of the title compound.

Melting point: 96–98° C.
Elemental analysis (for $C_{26}H_{34}N_6O \cdot H_2O$):
Calculated (%): C, 70.12; H, 7.36; N, 17.52
Found (%): C, 70.29; H, 7.19; N, 17.62

EXAMPLE 115

Production of 6-[3-[4-(diphenylmethoxy)piperidino]-2-hydroxypropylamino][1,2,4]triazolo[1,5-b]pyridazine 0.675 g of 3-[4-(diphenylmethoxy)piperidino]-2-hydroxypropylamine and 0.335 g of 6-chloro[1,2,4]triazolo[1,5-b]pyridazine were stirred at 135–140° C. for 3 hours. After cooling, aqueous sodium bicarbonate was added, followed by extraction with ethyl acetate-tetrahydrofuran (2:1); the extract was washed with saline and dried with sodium sulfate. The dry product was concentrated under reduced pressure; the residue was subjected to silica gel column chromatography and eluted with ethyl acetate:methanol:triethylamine (90:10:1). The desired fraction was collected, recrystallized from ethyl acetate and dried to yield 0.509 g of the title compound.

Melting point: 82–87° C.
Elemental analysis (for $C_{26}H_{30}N_6O_2 \cdot H_2O$):
Calculated (%): C, 65.53; H, 6.77; N, 17.63
Found (%): C, 65.36; H, 6.50; N, 17.25

EXAMPLE 116

Production of tert-butyl [6-[3-[4-(diphenylmethoxy)piperidino]propylamino][1,2,4]triazolo[1,5-b]pyridazin-2-yl]carboxylate 563 mg of 4-(diphenylmethoxy)-1-piperidinepropanamine and 442 mg of tert-butyl (6-chloro[1,2,4]triazolo[1,5-b]pyridazin-2-yl)carboxylate were dissolved in 5 ml of pyridine, followed by stirring at 80° C. for 13.5 hours. After cooling, water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected and concentrated under reduced pressure; the residue was crystallized by the addition of ethyl acetate, collected by filtration, washed with ethyl ether and dried to yield 365 mg of the title compound.

Melting point: 133–135° C.
Elemental analysis (for $C_{31}H_{38}N_6O_3$):
Calculated (%): C, 68.61; H, 7.06; N, 15.49
Found (%): C, 68.18; H, 6.81; N, 15.46

EXAMPLE 117

Production of [6-[3-[4-(diphenylmethoxy)piperidino]propylamino][1,2,4]triazolo[1,5-b]pyridazin-2-yl]carboxylic acid 2.33 g of 4-(diphenylmethoxy)-1-piperidinepropaneamine and 714 mg of (6-chloro[1,2,4]triazolo[1,5-b]pyridazin-2-yl)carboxylic acid were stirred at 175° C. for 30 minutes. After cooling, the reaction mixture was crystallized by the addition of water-ethyl acetate-ethanol (2:2:1), collected by filtration, washed with water-ethyl acetate-ethyl ether (2:1:2) and dried to yield 598 mg of the title compound.

Melting point: 135–138° C.
Elemental analysis (for $C_{27}H_{30}N_6O_3 \cdot 0.5H_2O$):
Calculated (%): C, 65.44; H, 6.31; N, 16.96
Found (%): C, 65.76; H, 6.13; N, 16.97

EXAMPLE 118

Production of methyl [6-[3-[4-(diphenylmethoxy)piperidino]propylamino][1,2,4]triazolo[1,5-b]pyridazin-7-yl]carboxylate 1.42 g of 4-(diphenylmethoxy)-1-piperidinepropanamine and 929 mg of methyl (6-chloro[1,2,4]triazolo[1,5-b]

pyridazin-7-yl)carboxylate were dissolved in 20 ml of N,N-dimethylformamide; 1.51 ml of N-ethyldiisopropylamine was added, followed by stirring at 70° C. for 6 hours. After cooling, water was added; the mixture was saturated with sodium chloride and extracted with ethyl acetate-tetrahydrofuran (1:1); the extract was dried with magnesium sulfate. The dry product was concentrated under reduced pressure; the residue was subjected to silica gel column chromatography and eluted with ethyl acetate:methanol:triethylamine (50:5:1). The desired fraction was collected and concentrated; the residue was crystallized by the addition of ethyl acetate-ethyl ether-hexane (1:2:1), collected by filtration, washed with hexane and dried to yield 905 mg of the title compound.

Melting point: 120–122° C.
Elemental analysis (for $C_{28}H_{32}N_6O_3$):
Calculated (%): C, 67.18; H, 6.44; N, 16.79
Found (%): C, 67.11; H, 6.54; N, 16.87

EXAMPLE 119

Production of [6-[3-[4-(diphenylmethoxy)piperidino]propylamino][1,2,4]triazolo[1,5-b]pyridazin-7-yl]carboxylic acid 1.58 g of methyl [6-[3-[4-(diphenylmethoxy)piperidino]propylamino][1,2,4]triazolo[1,5-b]pyridazin-7-yl]carboxylate was dissolved in 10 ml of ethanol; 8.0 ml of a 1 N aqueous solution of sodium hydroxide was added, followed by stirring at room temperature for 1.5 hours. After cooling, the mixture was concentrated under reduced pressure; the residue was diluted with water and washed with ethyl acetate; 1 N hydrochloric acid was added to ajust pH 4.5. The mixture was saturated with saline and extracted with tetrahydrofuran; the extract was dried with magnesium sulfate. The crystal obtained by concentration under reduced pressure was washed with ethyl ether, collected by filtration and dried to yield 788 mg of the title compound.

Melting point: 207–209° C.
Elemental analysis (for $C_{27}H_{30}N_6O_3 \cdot 0.5H_2O$):
Calculated (%): C, 65.44; H, 6.30; N, 16.96
Found (%): C, 65.17; H, 6.19; N, 16.90

EXAMPLE 120

Production of N-[6-[3-[4-(diphenylmethoxy)piperidino]propylamino][1,2,4]triazolo[1,5-b]pyridazine-2-carbonyl]glycine ethyl ester 1.41 g of 4-(diphenylmethoxy)-1-piperidinepropanamine and 1.23 g of N-(6-chloro[1,2,4]triazolo[1,5-b]pyridazine-2-carbonyl)glycine ethyl ester were dissolved in 17 ml of N,N-dimethylformamide; 1.50 ml of N-ethyldiisopropylamine was added, followed by stirring at room temperature for 28 hours, then at 60° C. for 19 hours. After cooling, aqueous sodium bicarbonate was added, followed by extraction with ethyl acetate-tetrahydrofuran (1:1); the extract was dried with magnesium sulfate. The dry product was concentrated under reduced pressure; the residue was subjected to silica gel column chromatography and eluted with ethyl acetate:methanol:triethylamine (50:5:1). The desired fraction was collected, concentrated, recrystallized by the addition of tetrahydrofuran, collected by filtration, washed with ethyl ether and dried to yield 987 mg of the title compound.

Melting point: 175–177° C.
Elemental analysis (for $C_{31}H_{37}N_7O_4$):
Calculated (%): C, 64.12; H, 6.60; N, 16.88
Found (%): C, 63.99; H, 6.52; N, 16.85

EXAMPLE 121

Production of N-[6-[3-[4-(diphenylmethoxy)piperidino]propylamino][1,2,4]triazolo[1,5-b]pyridazine-2-carbonyl]-2,2-dimethylglycine ethyl ester fumarate 1.56 g of 4-(diphenylmethoxy)-1-piperidinepropanamine and 1.50 g of N-(6-chloro[1,2,4]triazolo[1,5-b]pyridazine-2-carbonyl)-2,2-dimethylglycine ethyl ester were dissolved in 20 ml of N,N-dimethylformamide; 1.65 ml of N-ethyldiisopropylamine was added, followed by stirring at 70° C. for 16 hours. After cooling, aqueous sodium bicarbonate was added, followed by extraction with ethyl acetate; the extract was washed with saturated saline and dried with magnesium sulfate. The dry product was concentrated under reduced pressure; the residue was subjected to silica gel column chromatography and eluted with ethyl acetate:methanol:triethylamine (50:5:1). The desired fraction was collected and concentrated; 880 mg of the oily substance obtained was dissolved in 5 ml of ethanol, followed by the addition of 170 mg of fumaric acid and concentration; the resulting concentrate was powdered by the addition of ethyl ether, washed with ethyl ether, collected by filtration and dried to yield 931 mg of the title compound.

Noncrystalline
Elemental analysis (for $C_{37}H_{45}N_7O_8 \cdot 1.0H_2O$, $0.5Et_2O$):
Calculated (%): C, 60.76; H, 6.80; N, 12.72
Found (%): C, 60.71; H, 6.85; N, 12.34

EXAMPLE 122

Production of isopropyl [6-[3-[4-(diphenylmethoxy)piperidino]propoxy][1,2,4]triazolo[1,5-b]pyridazin-2-yl]carboxylate 653 mg of 4-(diphenylmethoxy)-1-piperidinepropanol was dissolved in 10 ml of N,N-dimethylformamide; 88 mg of a 60% dispersion of sodium hydride in mineral oil was added, followed by stirring at room temperature under reduced pressure for 1.5 hours. To the reaction mixture, 483 mg of isopropyl (6-chloro[1,2,4]triazolo[1,5-b]pyridazin-2-yl)carboxylate was added under ice cooling conditions, followed by stirring at constant temperature for 3.5 hours. Ice water was added, followed by extraction with ethyl acetate-tetrahydrofuran (1:1); the extract was washed with saturated saline and dried with magnesium sulfate. The dry product was concentrated under reduced pressure; the residue was subjected to silica gel column chromatography and eluted with ethyl acetate:methanol (10:1). The desired fraction was collected and concentrated; the crystal precipitated was washed with ethyl ether, collected by filtration and dried to yield 462 mg of the title compound.

Melting point: 126–127° C.
Elemental analysis (for $C_{30}H_{35}N_5O_4$):
Calculated (%): C, 68.03; H, 6.66; N, 13.22
Found (%): C, 68.01; H, 6.79; N, 13.42

EXAMPLE 123

Production of [6-[3-[4-(diphenylmethoxy)piperidino]propoxy][1,2,4]triazolo[1,5-b]pyridazin-2-yl]carboxylic acid 1.85 g of isopropyl [6-[3-[4-(diphenylmethoxy)piperidino]propoxy][1,2,4]triazolo[1,5-b]pyridazin-2-yl]

carboxylate was dissolved in 18 ml of tetrahydrofuran; 3.8 ml of a 1 N aqueous solution of sodium hydroxide was added, followed by stirring at room temperature for 3.5 hours. After cooling, the mixture was concentrated under reduced pressure; the residue was diluted with water and washed with ethyl acetate; 1 N hydrochloric acid was added to ajust pH 4.5. The mixture was crystallized by the addition of ethanol-acetone (1:2), collected by filtration, washed with water and ethyl acetate and dried to yield 1.33 g of the title compound.

Melting point: 173–177° C.

Elemental analysis (for $C_{27}H_{29}N_5O_4 \cdot 2.5H_2O$):

Calculated (%): C, 60.89; H, 6.43; N, 13.15

Found (%): C, 60.86; H, 6.21; N, 13.06

EXAMPLE 124

Production of N-[6-[3-[4-(diphenylmethoxy)piperidino]propylamino][1,2,4]triazolo[1,5-b]pyridazine-2-carbonyl]-2,2-dimethylglycine 1.71 g of N-[6-[3-[4-(diphenylmethoxy)piperidino]propylamino][1,2,4]triazolo[1,5-b]pyridazine-2-carbonyl]-2,2-dimethylglycine ethyl ester was dissolved in 6 ml of ethanol; 4.5 ml of a 1 N aqueous solution of sodium hydroxide was added, followed by stirring at room temperature for 2 hours. Under ice cooling conditions, 1 N hydrochloric acid was added to bring the mixture to pH 5. The crystal obtained was collected by filtration, washed with water and ethyl acetate and dried to yield 1.24 g of the title compound.

Melting point: 247–249° C.

Elemental analysis (for $C_{31}H_{37}N_6O_4 \cdot 1.0H_2O$):

Calculated (%): C, 63.14; H, 6.67; N, 16.63

Found (%): C, 63.09; H, 6.81; N, 16.70

EXAMPLE 125

Production of N-[6-[3-[4-(diphenylmethoxy)piperidino]propylamino][1,2,4]triazolo[1,5-b]pyridazine-2-carbonyl]glycine 928 mg of N-[6-[3-[4-(diphenylmethoxy)piperidino]propylamino][1,2,4]triazolo[1,5-b]pyridazine-2carbonyl]glycine ethyl ester was dissolved in 7 ml of ethanol; 2.2 ml of a 1 N aqueous solution of sodium hydroxide was added, followed by stirring at room temperature for 1.5 hours. The mixture was concentrated under reduced pressure; the residue was diluted with water; 1 N hydrochloric acid was added to bring the mixture to pH 4.5. The crystal obtained was collected by filtration, washed with water, acetone and ethyl acetate and dried to yield 443 mg of the title compound.

Melting point: 256–258° C.

Elemental analysis (for $C_{29}H_{33}N_7O_4 \cdot 1.5H_2O$):

Calculated (%): C, 61.04; H, 6.36; N, 17.18

Found (%): C, 61.29; H, 6.28; N, 17.35

EXAMPLE 126

Production of N-[6-[3-[4-(diphenylmethoxy)piperidino]propoxy][1,2,4]triazolo[1,5-b]pyridazine-2-carbonyl]-2,2-dimethylglycine ethyl ester 1.5 fumarate 986 mg of [6-[3-[4-(diphenylmethoxy)piperidino]propoxy][1,2,4]triazolo[1,5-b]pyridazin-2-yl]carboxylic acid and 0.38 ml of N-ethyldiisopropylamine were suspended in 10 ml of N,N-dimethylformamide; 361 mg of N,N'-carbonyldiimidazole was added, followed by stirring at room temperature for 3 hours. After 372 mg of 2-aminoisobutyric acid ethyl ester hydrochloride was added, the mixture was stirred at room temperature for 43 hours, then at 60° C. for 5 hours. Ice water was added, followed by extraction with ethyl acetate-tetrahydrofuran (1:1); the extract was washed with saturated saline and dried with magnesium sulfate. The dry product was concentrated under reduced pressure; the residue was subjected to silica gel column chromatography and eluted with ethyl acetate-:methanol:triethylamine (50:1:1). The desired fraction was collected and concentrated under reduced pressure, after which it was dissolved in 5 ml of ethanol; 139 mg of fumaric acid was added, followed by concentration. Ethanol-ethyl acetate (1:3) was added to cause crystallization; the crystal precipitated was washed with ethyl ether, collected by filtration and dried to yield 581 mg of the title compound.

Melting point: 127–130° C.

Elemental analysis (for $C_{39}H_{46}N_6O_{11}$):

Calculated (%): C, 60.45; H, 5.98; N, 10.85

Found (%): C, 60.06; H, 5.91; N, 10.80

EXAMPLE 127

Production of N-[6-[3-[4-(diphenylmethoxy)piperidino]propylamino]-3-methylimidazo[1,2-b]pyridazine-2-carbonyl]glycine ethyl ester 1.17 g of 4-(diphenylmethoxy)-1-piperidinepropanamine and 0.891 g of N-(6-chloro-3-methylimidazo[1,2-b]pyridazine-2-carbonyl)glycine ethyl ester were dissolved in 10 ml of 1-methyl-2-pyrrolidone; 0.517 ml of N-ethyldiisopropylamine was added, followed by stirring in an oil bath (90–100° C.) for 15 hours. After cooling, ice water was added, followed by extraction with ethyl acetate; the extract was washed with saline and dried with magnesium sulfate. The dry product was concentrated under reduced pressure; the residue was subjected to silica gel column chromatography and eluted with ethyl acetate-:methanol:triethylamine (90:10:1). The desired fraction was collected and recrystallized with ethyl acetate-ethyl ether (1:1) to yield 0.629 g of the title compound.

Melting point: 158–160° C.

Elemental analysis (for $C_{33}H_{40}N_6O_4$):

Calculated (%): C, 67.79; H, 6.90; N, 14.37

Found (%): C, 67.52; H, 6.92; N, 14.13

EXAMPLE 128

Production of 6-[3-[4-diphenylmethoxy)piperidino]propylamino]-2-isopropylimidazo[1,2-b]pyridazine hydrochloride A mixture of 4-(diphenylmethoxy)-1-piperidinepropanamine (2.60 g), 6-chloro-2-isopropylimidazo[1,2-b]pyridazine (0.783 g) and potassium iodide (0.133 g) was stirred at 190° C. in a nitrogen atmosphere for 5 hours. The reaction mixture was cooled to 100° C.; ethanol (2 ml) was added drop by drop, after which the mixture was cooled to room temperature. To this mixture, an aqueous solution of sodium hydrogen carbonate (0.40 g) was added, followed by 2 extractions with ethyl acetate. The organic layers combined were washed with water, filtered and concentrated under reduced pressure. The residue was subjected to silica gel column chromatography (ethyl acetate, then ethyl acetate:methanol:triethylamine 500:25:1 and then 50:5:1). The desired fraction was collected, concentrated and dissolved in methanol; a 10% solution of hydrogen chloride/methanol (3 ml) was added, followed by concentration under reduced pressure, to yield the title compound (1.13 g).

Noncrystalline

Elemental analysis (for $C_{30}H_{38}N_5OCl.0.75H_2O$):

Calculated (%): C, 67.52; H, 7.46

Found (%): C, 67.32; H, 7.42

EXAMPLE 129

Production of ethyl 2-[6-[3-[4-[phenyl(2-thineyl) methylamino]piperidino]propylamino]imidazo[1,2-b]pyridazin-2-yl]-2-methylpropionate trihydrochloride 1.44 g of 4-[phenyl(2-thienyl)methylamino]-1-piperidinepropanamine and 585 mg of ethyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 4 hours. After cooling, ethanol and saturated aqueous sodium bicarbonate were added, followed by extraction with ethyl acetate; the extract was washed with saturated saline and dried with magnesium sulfate. The solution was concentrated under reduced pressure; the residue was subjected to silica gel column chromatography and eluted with ethyl acetate: methanol:triethylamine (50:5:1). The desired fraction was collected, concentrated, dissolved in 5 ml of ethyl acetate; 0.86 ml of 4N-hydrogenchloride in ethyl acetate was added, followed by concentration. Ethanol-ethyl acetate (1:4) was added to the residue; the crystal precipitated was collected by filtration and dried to yield 609 mg of the title compound.

Melting point: 175–178° C.

Elemental analysis (for $C_{31}H_{43}N_6O_2SCl_3.1.0H_2O$):

Calculated (%): C, 54.11; H, 6.59; N, 12.21

Found (%): C, 54.17; H, 6.49; N, 12.08

EXAMPLE 130

Production of ethyl 2-[6-[3-[4-(hydroxydiphenylmethyl) piperidino]propylamino] imidazo[1,2-b]pyridazin-2-yl]-2-methylpropionate dihydrochloride 427 mg of 4-(hydroxydiphenylmethyl)-1-piperidinepropanamine and 235 mg of ethyl 2-(6-chloroimidazo[1,2-b]pyridazin-2-yl)-2-methylpropionate were stirred at 160° C. for 3.5 hours. After cooling, ethanol and saturated aqueous sodium bicarbonate were added, followed by extraction with ethyl acetate; the extract was washed with saturated saline and dried with magnesium sulfate. The solution was concentrated under reduced pressure; the residue was subjected to silica gel column chromatography and eluted with ethyl acetate:methnol:triethylamine (50:5:1). The desired fraction was collected, concentrated, dissolved in 5 ml of ethyl acetate; 0.23 ml of 4N-hydrogenchloride in ethyl acetate was added, followed by concentration. Ethylether was added to the residue; the powder was collected by filtration and dried to yield 216 mg of the title compound. amorphous Elemental analysis (for $C_{33}H_{43}N_5O_3Cl_21.0H_2O, 0.5Et_2O$):

Calculated (%): C, 61.49; H, 7.37; N, 10.24

Found (%): C, 61.47; H, 7.36; N, 9.87

EXAMPLE 131

Production of ethyl 2-[6-[3-[3-(diphenylmethoxy) pyrrolidino]propylamino]imidazo[1,2-b]pyridazin-2-yl]-2-methylpropionate dihydrochloride 1.53 g of 3-(diphenylmethoxy)-1-pyrrolidinepropanamine and 660 mg of ehtyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 8 hours. After cooling, saturated aqueous sodium bicarbonate was added, followed by extraction with ethyl acetate; the extract was washed with water and saturated saline and dried with magnesium sulfate. The solution was concentrated under reduced pressure; the residue was subjected to silica gel column chromatography and eluted with ethyl acetate:methanol:triethylamine (50:5:1). The desired fraction was collected, concentrated, dissolved in 5 ml of ethyl acetate; 0.81 ml of 4N-hydrogenchloride in ethyl acetate was added, followed by concentration. Ethylether was added to the residue; the powder was collected by filtration and dried to yield 877 mg of the title compound.

amorphous

Elemental analysis (for $C_{32}H_{41}N_5O_3Cl_2.1.0H_2O$):

Calculated (%): C, 60.75; H, 6.85; N, 11.07

Found (%): C, 60.50; H, 6.55; N, 10.81

EXAMPLE 132

Production of ethyl 2-[6-[3-[4-(10,11-dihydro-5H-dibenzo[a,d]cyclohepten-5-oxy)piperidino] propylamino]imidazo[1,2-b]pyridazin-2-yl]-2-methylpropionate 1.69 g of 4-(10,11-dihydro-5H-dibenzo[a,d]cyclohepten-5-oxy)-1-piperidinepropanamine and 645 mg of ethyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 7 hours. After cooling, saturated aqueous sodium bicarbonate was added, followed by extraction with ethyl acetate; the extract was washed with water and saturated saline and dried with magnesium sulfate. The solution was concentrated under reduced pressure; the residue was subjected to silica gel column chromatography and eluted with ethyl acetate:methanol:triethylamine (50:5:1). The desired fraction was collected, concentrated, the residue was subjected to silica gel column chromatography again and eluted with dichloromethane:methanol:triethylamine (100:1:2). The desired fraction was collected and concentrated to yield 340 mg of the title compound.

$^1$H-NMR (CDCl$_3$) δ ppm: 1.21(3H,t,J=7.0 Hz), 1.52–2.20 (8H,m), 1.64 (6H,s), 2.43–2.60(2H,m), 2.70–2.92(2H,m), 2.95–3.10(2H,m), 3.28–3.62(5H,m), 6.14(2H,d,J=7.0 Hz), 6.29(1H,d,J=9.4Hz), 6.40–6.50(1H,brs), 7.05–7.22(6H,m), 7.33–7.43(2H,m), 7.54 (1H,d,J=9.4Hz).

Reference Example 1

Production of 4-(diphenylmethoxy)-1-piperidinepropanol 2.67 g of 4-diphenylmethoxypiperidine was dissolved in 20 ml of N,N-dimethylformamide; 1.09 ml of 3-bromopropanol and 1.66 g of potassium carbonate were added, followed by stirring at room temperature for 40 hours. Ice water was added, followed by extraction with ethyl acetate; the extract was washed with saline and dried with magnesium sulfate. After the dry product was concentrated under reduced pressure, the residue was subjected to silica gel column chromatography and eluted with ethyl acetate:methanol:triethylamine (90:10:1). The desired fraction was collected and concentrated to yield 2.32 g of the title compound.

$^1$H-NMR (CDCl$_3$) δ ppm: 1.5–2.4 (10H, m), 2.58 (2H, t, J=5 Hz), 3.3–3.6 (1H, m), 3.78 (2H, t, J=5 Hz), 5.50 (1H, s), 7.1–7.5 (10H, m).

Reference Example 2

Production of 4-(diphenylmethoxy)-1-piperidinebutanol 1.05 g of 4-(diphenylmethoxy)piperidine was dissolved in 10 ml of N,N-dimethylformamide; 0.57 ml of 4-bromobutyl acetate and 652 mg of potassium carbonate were added, followed by stirring at 50° C. for 3 hours. Ice water was added, followed by extraction with ethyl ether; the extract was washed with saline and dried with magnesium sulfate. After the dry product was concentrated under reduced pressure, the residue was dissolved in 15 ml of ethanol; 8 ml of a 1 N aqueous solution of sodium hydroxide was added, followed by stirring at room temperature. After the mixture was concentrated under reduced pressure, the residue was neutralized with 1 N hydrochloric acid, followed by extraction with ethyl acetate; the extract was washed with saline and dried with magnesium sulfate. After the dry product was concentrated under reduced pressure, the crystal precipitate was collected, washed with ethyl ether and dried to yield 1.21 g of the title compound.

$^1$H-NMR (CDCl$_3$) δ ppm: 2.95 (2H, t, J=5 Hz), 1.6–3.4 (13H, m), 3.74 (2H, t, J=5 Hz), 5.43 (1H, s), 7.2–7.5 (10H, m).

Reference Example 3

Production of 4-(diphenylmethoxy)-1-piperidinehexanol 1.00 g of 4-(diphenylmethoxy)piperidine was dissolved in 10 ml of N,N-dimethylformamide; 0.49 ml of 6-bromohexanol, 0.56 g of sodium iodide and 0.62 g of potassium carbonate were added, followed by stirring at 100° C. for 1 hour. Ice water was added, followed by extraction with ethyl ether; the extract was washed with saline and dried with magnesium sulfate. After the dry product was concentrated under reduced pressure, the residue was subjected to silica gel column chromatography and eluted with ethyl acetate::methanol:triethylamine (90:10:1). The desired fraction was collected and concentrated to yield 1.24 g of the title compound.

$^1$H-NMR (CDCl$_3$) δ ppm: 1.2–2.0 (12H, m), 2.0–2.2 (2H, m), 2.30 (2H, t, J=8 Hz), 2.6–2.9 (2H, m), 3.3–3.6 (1H, m), 3.63 (2H, t, J=6 Hz), 5.52 (1H, s), 7.1–7.5 (10H, m).

Reference Example 4

Production of 4-(diphenylmethoxy)-1-[2-(2-hydroxyethoxy)ethyl]piperidine 1.30 g of 4-(diphenylmethoxy)piperidine was dissolved in 10 ml of N,N-dimethylformamide; 0.52 ml of 2-(2-chloroethoxy)ethanol, 0.73 g of sodium iodide and 0.81 g of potassium carbonate were added, followed by stirring at 100° C. for 1 hour. Ice water was added, followed by extraction with ethyl ether; the extract was washed with saline and dried with magnesium sulfate. After the dry product was concentrated under reduced pressure, the residue was subjected to silica gel column chromatography and eluted with ethyl acetate:methanol:triethylamine (90:10:1). The desired fraction was collected and concentrated to yield 1.47 g of the title compound.

$^1$H-NMR (CDCl$_3$) δ ppm: 1.6–2.4 (6H, m), 2.54 (2H, t, J=6 Hz), 2.6–3.0 (2H, m), 3.3–3.5 (1H, m), 3.5–3.8 (6H, m), 5.50 (1H, s), 7.1–7.5 (10H, m).

Reference Example 5

Production of 4-(diphenylmethyl)-1-[2-(2-hydroxyethoxy)ethyl]piperazine 1.00 g of 1-(diphenylmethyl)piperazine was dissolved in 10 ml of N,N-dimethylformamide; 0.42 ml of 2-(2-chloroethoxy)ethanol, 0.59 g of sodium iodide and 0.66 g of potassium carbonate were added, followed by stirring at 100° C. for 1 hour. Ice water was added, followed by extraction with ethyl ether; the extract was washed with saline and dried with magnesium sulfate. After the dry product was concentrated under reduced pressure, the residue was subjected to silica gel column chromatography and eluted with dichloromethane:ethyl acetate:methanol (10:10:1). The desired fraction was collected and concentrated to yield 1.47 g of the title compound.

$^1$H-NMR (CDCl$_3$) δ ppm: 2.3–2.8 (8H, m), 2.57 (2H, t, J=6 Hz), 3.5–3.8 (6H, m), 4.21 (1H, s), 7.1–7.5 (10H, m).

Reference Example 6

Production of 2-tert-butyl-6-chloro[1,2,4]triazolo[1,5-b]pyridazine

Process A: N-(6-chloropyridazin-3-yl)pivalamidoxime 36 g of N,N-dimethylpivalamide was dissolved in 85 ml of toluene; under ice cooling conditions, 11.3 ml of phosphorus oxychloride was added drop by drop, followed by stirring at room temperature for 24 hours. To this solution, 12.0 g of 3-amino-6-chloropyridazine was added, followed by stirring at 60–70° C. for 24 hours. After cooling, ethyl acetate was added; the mixture was washed with a 2 N aqueous solution of sodium hydroxide and saline and dried with sodium sulfate. After the dry product was concentrated under reduced pressure, the residue was subjected to silica gel column chromatography and eluted with hexane:ethyl acetate:triethylamine (50:50:2). The desired fraction was collected to yield 6.38 g of N,N-dimethyl-N'-(6-chloropyridazin-3-yl)pivalamidine. The mother liquor was purified by silica gel column chromatography to yield 6.07 g of the amidine. 12.45 g of the amidine derivative obtained was dissolved in 100 ml of methanol; a solution of 4.31 g of hydroxylamine hydrochloride in methanol was added, followed by stirring at room temperature for 2 hours. The methanol was concentrated to half volume under reduced pressure; the crystal precipitated was collected by filtration, washed with water and ethyl ether and dried to yield 10.44 g of the title compound.

Melting point: 128–130° C.

Elemental analysis (for C$_9$H$_{13}$N$_4$Cl):

Calculated (%): C, 47.27; H, 5.73; N, 24.50

Found (%): C, 47.28; H, 5.59; N, 24.34

Process B 4.07 g of N-(6-chloropyridazin-3-yl)pivalamidoxime was suspended in 170 ml of chloroform; 8.3 ml of phosphorus oxychloride was added drop by drop, followed by heating and refluxing for 5 hours. After cooling, ice water and a 2 N aqueous solution of sodium hydroxide were added, followed by extraction with chloroform; the extract was washed with saline and dried with magnesium sulfate. After the dry product was concentrated under reduced pressure, the residue was subjected to silica gel column chromatography and eluted with hexane:ethyl acetate (5:1). The desired fraction was collected and concentrated to yield 1.12 g of the title compound.

Melting point: 95–97° C.
Elemental analysis (for $C_9H_{11}N_4Cl.0.3H_2O$ ):
Calculated (%): C, 50.03; H, 5.41; N, 25.93
Found (%): C, 50.23; H, 5.12; N, 25.90

Reference Example 7

Production of methyl 6-chloro[1,2,4]triazolo(1,5-b]pyridazine-2-carboxylate

Process A: 6-chloro[1,2,4]triazolo[1,5-b]pyridazin-2-carboxylic acid 10.0 g of 6-chloro-2-methyl[1,2,4]triazdo[1,5-b]pyridazine was added to 55 ml of concentrated sulfuric acid under ice cooling conditions; 19.4 g of sodium dichromate dihydrate was added little by little at constant temperature, followed by stirring at room temperature for 4 days. Under ice cooling conditions, about 200 ml of ice water was added; the crystal precipitated was collected by filtration, washed with water and ethyl ether and dried to yield 9.74 g of the title compound.

Melting point: 221° C. (decomp.)
Elemental analysis (for $C_6H_3N_4O_2Cl$):
Calculated (%): C, 36.29; H, 1.52; N, 28.22
Found (%): C, 35.96; H, 1.59; N, 28.12

Process B 3.02 g of 6-chloro[1,2,4]triazdo[1,5-b]pyridazin-2-carboxylic acid was dissolved in 50 ml of N,N-dimethylformamide; 3.15 ml of N-ethyldiisopropylamine was added, followed by the addition of 1.14 ml of methyl iodide with stirring under ice water cooling conditions. After stirring at room temperature for 19 hours, about 200 ml of ice water was added; the crystal precipitated was collected by filtration and washed with water and ethyl ether. The mother liquor was purified by silica gel column chromatography; the crystal obtained was combined with the above washings and dried to yield 2.91 g of the title compound.

Melting point: 208–209° C.
Elemental analysis (for $C_7H_5N_4O_2Cl$):
Calculated (%): C, 39.55; H, 2.37; N, 26.35
Found (%): C, 39.65; H, 2.46; N, 26.34

Reference Example 8

Production of ethyl 2-(6-chloroimidazo[1,2-b]pyridazin-2-yl)-2-methylpropionate

Method A
Process A: ethyl 6-chloroimidazo[1,2-b]pyridazin-2-acetate 11.2 g of 3-amino-6-chloropyridazine was suspended in 150 ml of ethanol; 28.6 g of ethyl 4-chloroacetoacetate was added, followed by heating and refluxing for 24 hours. After cooling, the mixture was concentrated under reduced pressure; the residue was ajusted to pH 7 by the addition of an aqueous solution of sodium hydrogen carbonate, followed by extraction with ethyl acetate; the extract was washed with saline and dried with magnesium sulfate. The dry product was concentrated under reduced pressure; the residue was subjected to silica gel flush column chromatography and eluted with hexane:ethyl acetate (2:3). The desired fraction was collected to yield 12.7 g of the title compound.

$^1$H-NMR (CDCl$_3$) δ ppm: 1.29 (3H, t, J=7 Hz), 3.89 (2H, s), 4.23 (2H, q, J=7 Hz), 7.05, 7.85 (each 1H, d, J=9 Hz), 7.95 (1H, s).

Process B 6.8 g of ethyl 6-chloroimidazo[1,2-b]pyridazin-2-acetate was dissolved in 50 ml of N,N-dimethylformamide; while the solution was stirred under ice water cooling conditions, 2.46 g of a 60% sodium hydride dispersion in mineral oil was add little by little, followed by stirring at room temperature for 30 minutes. Under ice water cooling conditions, 4.36 ml of methyl iodide was added, followed by stirring at room temperature for 2 hours. Ice water was poured, followed by extraction with ethyl acetate; the extract was washed with saline and dried with magnesium sulfate. The dry product was concentrated under reduced pressure; the residue was subjected to silica gel column chromatography and eluted with hexane:ethyl acetate (2:1). The desired fraction was collected and concentrated to yield 4.06 g of the title compound.

Melting point: 64–65° C.
Elemental analysis (for $C_{12}H_{14}N_3O_2Cl$):
Calculated (%): C, 53.84; H, 5.27; N, 15.70
Found (%): C, 53.85; H, 5.16; N, 15.80

Method B

The title compound may be produced according to the following method.

80.0 g of 3-amino-6-chloropyridazine, 201 g of ethyl 4-bromo-2,2-dimethyl-3-oxobutanoate and 131 g of disodium hydrogenphosphate were suspended in 300 ml of ethanol, followed by heating and refluxing for 8 hours. 300 ml of water was added to the reaction mixture, followed by two extractions with ethyl acetate. The organic layers combined was washed with 600 ml of water twice and with 300 ml of a saturated solution of sodium chloride, followed by drying on magnesium sulfate, treating with activated carbons, filtration and concentrating under reduced pressure. The residue was dissolved in 200 ml of diisopropyl ether; the insoluble substances were filtrated off and the filtrate was concentrated under reduced pressure. The residue was subjected to silica gel column chromatography (hexane:ethyl acetate 100:1, 2:1 and 1:1) and recrystallized from hexane to yield the title compound (99.3 g).

Reference Example 9

Production of methyl 2-(6-chloroimidazo[1,2-b]pyridazin-2-yl)-2-methylpropionate 10.1 g of 3-amino-6-chloropyridazine was suspended in 120 ml of methanol; 23.5 g of methyl 4-chloroacetoacetate was added, followed by heating and refluxing for 20 hours. After cooling, the mixture was concentrated under reduced pressure; the residue was ajusted to pH 7 by the addition of an aqueous solution of sodium hydrogen carbonate, followed by extraction with ethyl ether; the extract was washed with saline and dried with magnesium sulfate. The dry product was concentrated under reduced pressure; the residue was subjected to silica gel column chromatography and eluted with hexane:ethyl acetate (1:4). The desired fraction was collected to yield 9.15 g of methyl 6-chloroimidazo[1,2-b]pyridazin-2-acetate was dissolved in 10 ml of N,N-dimethylformamide; while the solution was stirred under ice water cooling conditions, 3.5 g of a 60% sodium hydride dispersion in mineral oil was add little by little, followed by stirring at room temperature for 30 minutes. Under ice water cooling conditions, 6.3 ml of methyl iodide was added, followed by stirring at room temperature for 5 hours. Ice water was poured, followed by extraction with ethyl acetate; the extract was washed with saline and dried with magnesium sulfate. The dry product was concentrated under reduced pressure; the residue was subjected to silica gel column chromatography and eluted with hexane:ethyl acetate (1:1). The desired fraction was collected and concentrated to yield 14.1 g of the title compound.

Melting point: 92–93° C.

Elemental analysis (for $C_{11}H_{12}N_3O_2Cl$):

Calculated (%): C, 52.08; H, 4.77; N, 16.56

Found (%): C, 52.01; H, 4.60; N, 16.59

Reference Example 10

Production of 2-(6-chloroimidazo[1,2-b]pyridazin-2-yl)-2-methylpropionic acid 1.40 g of methyl 2-(6-chloroimidazo[1,2-b]pyridazin-2-yl)-2-methylpropionate was dissolved in 15 ml of tetrahydrofuran; 9 ml of a 1 N aqueous solution of sodium hydroxide was added, followed by stirring at room temperature for 3 hours. After the mixture was concentrated under reduced pressure, the residue was ajusted to pH 4 by the addition of 1 N hydrochloric acid; the crystal precipitated was collected by filtration to yield 1.06 g of the title compound.

Melting point: 159–161° C.

Elemental analysis (for $C_{10}H_{10}N_3O_2Cl$):

Calculated (%): C, 50.12; H, 4.21; N, 17.53

Found (%): C, 50.36; H, 4.34; N, 17.32

Reference Example 11

Production of tert-butyl 2-(6-chloroimidazo[1,2-b]pyridazin-2-yl)-2-methylpropionate 0.863 g of 2-(6-chloroimidazo[1,2-b]pyridazin-2-yl)-2-methylpropionic acid was suspended in 10 ml of toluene; 2.6 ml of N,N-dimethylformamide di-tert-butylacetal was added, followed by stirring at 80° C. for 1 hour. After cooling, the mixture was diluted with ethyl acetate, washed with an aqueous solution of sodium hydrogen carbonate and dried with magnesium sulfate. After the dry product was concentrated under reduced pressure, ethyl ether was added to the residue; the crystal separated was collected and dried to yield 0.52 g of the title compound.

$^1$H-NMR (CDCl$_3$) δ ppm: 1.43 (9H, s), 1.64 (6H, s), 7.02, 7.87 (each 1H, d, J=9 Hz), 7.84 (1H, s).

Reference Example 12

Production of 6-chloro-2-methoxyimidazo[1,2-b]pyridazine 2.69 g of 6-chloro-2-hydroxyimidazo[1,2-b]pyridazine was suspended in 30 ml of N,N-dimethylformamide; 838 mg of a 60% sodium hydride dispersion in mineral oil was added little by little, followed by stirring at room temperature for 30 minutes. Under ice water cooling conditions, 1.2 ml of methyl iodide was added, followed by stirring at room temperature for 3 days. Ice water was added, followed by extraction with ethyl acetate; the extract was washed with saline and dried with magnesium sulfate. After the dry product was concentrated under reduced pressure, the residue was subjected to silica gel column chromatography and eluted with hexane:ethyl acetate (5:1). The desired fraction was collected and concentrated to yield 1.05 g of the title compound.

Melting point: 134–136° C.

Elemental analysis (for $C_7H_6N_3OCl$):

Calculated (%): C, 45.79; H, 3.29; N, 22.89

Found (%): C, 45.68; H, 3.27; N, 22.79

Reference Example 13

Production of 4-(diphenylmethoxy)-1-piperidinepentanamine 3.70 g of potassium phthalimide was dissolved in 20 ml of N,N-dimethylformamide; 5.4 ml of 1,5-dichloropentane was added, followed by stirring at room temperature for 15 hours. Ice water was added to the reaction mixture, followed by extraction with ethyl acetate; the extract was washed with saline and dried with magnesium sulfate. The dry product was concentrated under reduced pressure; the residue was subjected to silica gel column chromatography and eluted with hexane-ethyl acetate (4:1). The desired fraction was collected to yield 4.68 g of N-(5-bromopentyl)phthalimide as an oily substance. 4.68 g of N-(5-bromopentyl) phthalimide and 4.25 g of 4-(diphenylmethoxy)piperidine were dissolved in 30 ml of N,N-dimethylformamide; 2.42 g of potassium carbonate was added, followed by stirring at room temperature for 15 hours. Ice water was added to the reaction mixture, followed by extraction with ethyl acetate; the extract was washed with saline and dried with magnesium sulfate. The dry product was concentrated under reduced pressure; the residue was subjected to silica gel column chromatography and eluted with hexane-ethyl acetate-triethylamine (50:50:1). The desired fraction was collected to yield 6.67 g of N-[5-[4-(diphenylmethoxy)piperidino]pentyl]phthalimide as an oily substance. 6.6 g of N-[5-[4-(diphenylmethoxy)piperidino]pentyl]phthalimide was dissolved in 30 ml of ethanol; 0.694 ml of hydrazine monohydrate was added, followed by thermal refluxing for 3 hours. After cooling, the mixture was concentrated under reduced pressure; ethyl acetate was added to the residue; the crystal precipitated was collected, dissolved in 15 ml of a 1 N aqueous solution of sodium hydroxide and 20 ml of water and extracted with ethyl acetate; the extract was washed with saline and dried with sodium sulfate. The dry product was concentrated under reduced pressure; the crystal obtained was collected to yield 3.29 g of the title compound.

$^1$H-NMR (CDCl$_3$) δ ppm: 1.2–2.9 (18H, m), 3.3–3.6 (1H, m), 5.52 (1H, s), 7.1–7.4 (10H, m).

Reference Example 14

Production of 3-[4-(diphenylmethoxy)piperidino]-2-hydroxypropylamine 3.70 g of potassium phthalimide was dissolved in 20 ml of N,N-dimethylformamide; 2.58 ml of epibromohydrin was added, followed by stirring at room temperature for 15 hours. Ice water was added to the reaction mixture, followed by extraction with ethyl acetate; the extract was washed with saline and dried with magnesium sulfate. The dry product was concentrated under reduced pressure; ethyl ether was added to the residue; the crystal precipitated was collected to yield 3.7 g of N-(oxylane-2-methyl)phthalimide. 0.61 g of N-(oxylane-2-methyl)phthalimide and 0.802 g of 4-(diphenylmethoxy) piperidine were dissolved in 10 ml of ethanol, followed by thermal refluxing for 2 hours. The reaction mixture was concentrated under reduced pressure; the residue was subjected to silica gel column chromatography and eluted with ethyl acetate. The desired fraction was collected to yield 1.30 g of N-[3-[4-(diphenylmethoxy) piperidino-2-hydroxypropyl]phthalimide as an oily substance. This oily substance was dissolved in 10 ml of ethanol; 0.14 ml of hydrazine monohydrate was added, followed by thermal refluxing for 3 hours. After cooling, the mixture was concentrated under reduced pressure; ethanol was added to the residue; the crystal precipitated was collected, dissolved in 3 ml of a 1 N aqueous solution of sodium hydroxide and 10 ml of water and extracted with ethyl acetate; the extract was washed with saline and dried with sodium sulfate. The dry product was concentrated under reduced pressure; the crystal obtained was collected to yield 0.76 g of the title compound.

$^1$H-NMR (CDCl$_3$) δ ppm: 1.2–3.0 (12H, m), 3.3–3.55 (1H, m), 3.55–3.8 (1H, m), 5.52 (1H, s), 7.1–7.5 (10H, m).

Reference Example 15

Production of 4-[bis(4-fluorophenyl)methoxy]-1-piperidinepropanamine 25 g of 4,4'-difluorobenzophenone was dissolved in ethanol-tetrahydrofuran (180 ml–60 ml); 2.16 g of sodium borohydride was added under ice cooling conditions, followed by stirring at room temperature for 30 minutes. The mixture was concentrated under reduced pressure; the residue was diluted with ice water and extracted with ethyl acetate; the extract was washed with saline and dried with magnesium sulfate. The dry product was concentrated under reduced pressure; the oily substance obtained was dissolved in 800 ml of toluene; 11.6 g of 4-hydroxypiperidine and 23.7 g of p-toluenesulfonic acid monohydrate were added, followed by thermal refluxing for 2 hours. After cooling, the mixture was concentrated under reduced pressure; ice water and 130 ml of a 1 N aqueous solution of sodium hydroxide were added, followed by extraction with ethyl acetate; the extract was washed with saline and dried with magnesium sulfate. The dry product was concentrated under reduced pressure; the oily substance obtained (34.5 g) was dissolved in 100 ml of N,N-dimethylformamide; 16.3 g of N-(3-bromopropyl)phthalimide and 10.5 g of potassium carbonate were added, followed by stirring at room temperature for 20 hours. Ice water was added to the reaction mixture, followed by extraction with ethyl acetate; the extract was washed with saline and dried with magnesium sulfate. The dry product was concentrated under reduced pressure; the residue was subjected to silica gel column chromatography and eluted with hexane-ethyl acetate (1:2). The desired fraction was collected to yield 20.5 g of N-[3-[4-[bis(4-fluorophenyl)methoxy]piperidino]propyl]-phthalimide as an oily substance. 20.5 g of this oily substance was dissolved in 150 ml of ethanol; 2.02 ml of hydrazine monohydrate was added, followed by thermal refluxing for 3 hours. After cooling, the mixture was concentrated under reduced pressure; ethanol was added to the residue; the crystal precipitated was collected, dissolved in 40 ml of a 1 N aqueous solution of sodium hydroxide and extracted with ethyl acetate-tetrahydrofuran (2:1); the extract was washed with saline and dried with sodium sulfate. The dry product was concentrated under reduced pressure to yield 12.07 g of the title compound as an oily substance.

$^1$H-NMR (CDCl$_3$) δ ppm: 1.5–2.2 (10H, m), 2.36 (2H, d, J=7 Hz), 2.74 (2H, d, J=7 Hz), 3.3–3.5 (1H, m), 5.47 (1H, s), 6.9–7.4 (8H, m).

Reference Example 16

Production of 4-[bis(4-methylphenyl)methoxy]-1-piperidinepropanamine 25 g of 4,4'-dimethylbenzophenone was dissolved in ethanol-tetrahydrofuran (180 ml–60 ml); 2.23 g of sodium borohydride was added under ice cooling conditions, followed by stirring at room temperature for 24 hours. The mixture was concentrated under reduced pressure; ice water was added to the residue; the crystal precipitated was collected and dried; the crystal obtained (30.5 g) was dissolved in 800 ml of toluene; 11.9 g of 4-hydroxypiperidine and 24.9 g of p-toluenesulfonic acid monohydrate were added, followed by thermal refluxing for 3 hours. After cooling, the mixture was concentrated under reduced pressure; 100 ml of ice water and 140 ml of a 1 N aqueous solution of sodium hydroxide were added, followed by extraction with ethyl acetate; the extract was washed with saline and dried with sodium sulfate. The dry product was concentrated under reduced pressure; the residue was subjected to silica gel column chromatography and eluted with ethyl acetate-methanol-triethylamine (90;10:1). The desired fraction was collected to yield 32.8 g of 4-[bis(4-methylphenyl)methoxy]piperidine as an oily substance. 16.4 g of 4-[bis(4-methylphenyl)methoxylpiperidine was dissolved in 100 ml of N,N-dimethylformamide; 14.2 g of N-(3-bromopropyl)phthalimide and 8.15 g of potassium carbonate were added, followed by stirring at room temperature for 16 hours. Ice water was added to the reaction mixture, followed by extraction with ethyl acetate; the extract was washed with saline and dried with magnesium sulfate. The dry product was concentrated under reduced pressure; the residue was subjected to silica gel column chromatography and eluted with hexane-ethyl acetate (1:2). The desired fraction was collected to yield 21.2 g of N-[3-[4-[bis(4-methylphenyl)methoxy]piperidino]propyl] phthalimide as an oily substance. 20.5 g of this oily substance was dissolved in 150 ml of ethanol; 2.18 ml of hydrazine monohydrate was added, followed by thermal refluxing for 3 hours. After cooling, the mixture was concentrated under reduced pressure; ethanol was added to the residue; the crystal precipitated was collected, dissolved in 40 ml of a 1 N aqueous solution of sodium hydroxide and extracted with ethyl acetate-tetrahydrofuran (2:1); the extract was washed with saline and dried with sodium sulfate. The dry product was concentrated under reduced pressure to yield 10.5 g of the title compound as an oily substance.

$^1$H-NMR (CDCl$_3$) δ ppm: 1.4–2.9 (14H, m), 2.31 (6H, s), 3.3–3.50 (1H, m), 5.46 (1H, s), 7.11, 7.22 (each 4H, d, J=8 Hz).

Reference Example 17

Production of N-(6-chloroimidazo[1,2-b]pyridazine-2-carbonyl]glycine ethyl ester 0.593 g of 6-chloroimidazo[1,2-b]pyridazine-2-carboxylic acid was suspended in 7.5 ml of N,N-dimethylformamide; 0.535 g of N,N'-carbonyldiimidazole and 0.46 g of glycine ethyl ester hydrochloride were added, followed by stirring at room temperature for 30 minutes. To this mixture, 0.457 ml of triethylamine was added, followed by further stirring for 1 hour. Ice water was added to the reaction mixture; the crystal precipitated was collected by filtration, washed with water and dried to yield 0.749 g of the title compound.

Melting point: 190–191° C.
Elemental analysis (for C$_{11}$H$_{11}$N$_4$O$_3$Cl):
Calculated (%): C, 46.74; H, 3.92; N, 19.82
Found (%): C, 46.70; H, 4.03; N, 19.75

Reference Example 18

Production of 2-(6-chloroimidazo[1,2-b]pyridazin-2-yl)-2-methylpropionamide 1.20 g of 2-(6-chloroimidazo[1,2-b]pyridazin-2-yl)-2-methylpropionic acid was dissolved in 8 ml of N,N- dimethylformamide; 0.892 g of N,N'-carbonyldiimidazole was added, followed by stirring at room temperature for 30 minutes. To this mixture, 0.321 g of ammonium chloride and 0.832 ml of triethylamine were added under ice cooling conditions, followed by stirring at room temperature for 3 hours. Ice water was added to the reaction mixture; the crystal precipitated was collected by filtration, washed with water and dried to yield 0.697 g of the title compound.

Melting point: 194–195° C.
Elemental analysis (for $C_{10}H_{11}N_4OCl$);
Calculated (%): C, 50.32; H, 4.65; N, 23.47
Found (%): C, 50.34; H, 4.60; N, 23.43

Reference Example 19

Production of N,N-dimethyl 2-(6-chloroimidazo[1,2-b]pyridazin-2-yl)-2-methylpropionamide 0.959 g of 2-(6-chloroimidazo[1,2-b]pyridazin-2-yl)-2-methylpropionic acid was dissolved in 6 ml of N,N-dimethylformamide; 0.714 g of N,N'-carbonyldiimidazole was added, followed by stirring at room temperature for 60 minutes. To this mixture, 0.392 g of dimethylamine hydrochloride and 0.665 ml of triethylamine were added under ice cooling conditions, followed by stirring at room temperature for 3 hours. Saline was added to the reaction mixture, followed by extraction with ethyl acetate; the extract was washed with saline and dried with magnesium sulfate. The dry product was concentrated under reduced pressure; the residue was subjected to silica gel column chromatography and eluted with ethyl acetate:methanol (95:5). The desired fraction was collected and concentrated; the crystal obtained was collected by filtration to yield 0.608 g of the title compound.

Melting point: 149–151° C.
Elemental analysis (for $C_{12}H_{15}N_4OCl$):
Calculated (%): C, 54.04; H, 5.67; N, 21.01
Found (%): C, 53.90; H, 5.85; N, 21.04

Reference Example 20

Production of 2-(6-chloroimidazo[1,2-b]pyridazin-2-yl)-2-methylpropanol 0.719 g of 2-(6-chloroimidazo[1,2-b]pyridazin-2-yl)-2-methylpropionic acid was dissolved in 15 ml of tetrahydrofuran; 0.535 g of N,N'-carbonyldiimidazole was added, followed by stirring at room temperature for 60 minutes. To this mixture, 1.15 g of tetra-n-butylammonium borohydride was added under ice cooling conditions, followed by stirring at room temperature for 1 hour. 2 ml of 5 N hydrochloric acid was added to the reaction mixture, followed by concentration under reduced pressure. The residue was ajusted to pH 7 by the addition of aqueous sodium carbonate and extracted with ethyl acetate; the extract was washed with saline and dried with magnesium sulfate. The dry product was concentrated under reduced pressure; the residue was subjected to silica gel column chromatography and eluted with ethyl acetate. The desired fraction was collected and concentrated; the crystal obtained was collected by filtration to yield 0.488 g of the title compound.

$^1$H-NMR (CDCl$_3$) δ ppm: 1.39 (6H, s), 3.72 (2H, s), 7.04, 7.82 (each 1H, d, J=9.5 Hz), 7.76 (1H, s).

Reference Example 21

Production of N-(6-chloroimidazo[1,2-b]pyridazine-2-carbonyl)-2,2-dimethylglycine ethyl ester 1.28 g of 6-chloroimidazo[1,2-b]pyridazine-2-carboxylic acid was suspended in 12 ml of N,N-dimethylformamide; 1.16 g of N,N'-carbonyldiimidazole was added, followed by stirring at room temperature for 30 minutes. To the reaction mixture, 1.20 g of 2-aminoisobutyric acid ethyl ester hydrochloride and 1.00 ml of triethylamine were added, followed by stirring at room temperature for 16 hours. Water was added, the crystal precipitated was collected by filtration; the filtrate was extracted with ethyl acetate; the extract was washed with saturated saline and dried with magnesium sulfate. The dry product was concentrated under reduced pressure; the residue was combined with the above crystal collected by filtration and subjected to silica gel column chromatography and eluted with hexane:ethyl acetate (2:1). The desired fraction was collected and concentrated under reduced pressure to yield 1.20 g of the title compound.

$^1$H-NMR (CDCl$_3$) δ ppm: 1.28 (3H, t, J=7.2 Hz), 1.70 (6H, s), 4.25 (2H, q, J=7.0 Hz), 7.13 (1H, d, J=9.4 Hz), 7.87 (1H, brs), 7.89 (1H, d, J=9.6 Hz), 8.41 (1H, s).

Reference Example 22

Production of ethyl 2-(3,6-dichloroimidazo[1,2-b]pyridazin-2-yl]-2-methylpropionate 4.07 g of ethyl 2-(6-chloroimidazo[1,2-b]pyridazin-2-yl)-2-methylpropionate was suspended in 60 ml of ethyl acetate; 2.13 g of N-chlorosuccinimide was added, followed by thermal refluxing for 4 hours. After cooling, water was added, followed by extraction with ethyl acetate; the extract was washed with saturated saline and dried with magnesium sulfate. The dry product was concentrated under reduced pressure; the residue was subjected to silica gel column chromatography and eluted with hexane:ethyl acetate (5:1). The desired fraction was collected and concentrated under reduced pressure to yield 4.48 g of the title compound.

Melting point: 66–67° C.
Elemental analysis (for $C_{12}H_{13}N_3O_2Cl_2$):
Calculated (%): C, 47.70; H, 4.34; N, 13.91
Found (%): C, 47.67; H, 4.23; N, 13.93

Reference Example 23

Production of methyl 2-(6-chloro-7-methylimidazo[1,2-b]pyridazin-2-yl)-2-methylpropionate Process A: Production of methyl 6-chloro-7-methylimidazo[1,2-b]pyridazin-2-acetate 15.3 g of 6-amino-3-chloro-4-methylpyridazine was suspended in 200 ml of methanol; 25.0 ml of methyl 4-chloroacetoacetate was added, followed by thermal refluxing for 36 hours. After cooling, the mixture was concentrated under reduced pressure; the residue was ajusted to pH 7 by the addition of an aqueous solution of sodium hydrogen carbonate and extracted with ethyl acetate; the extract was washed with saline and dried with magnesium sulfate. The dry product was concentrated under reduced pressure; the residue was subjected to silica gel column chromatography and eluted with hexane:ethyl acetate (1:4). The desired fraction was collected to yield 14.3 g of the title compound.

Melting point: 98–99° C.
Elemental analysis (for $C_{10}H_{10}N_3O_2Cl$):
Calculated (%): C, 50.12; H, 4.21; N, 17.53
Found (%): C, 50.07; H, 4.25; N, 17.74

Process B 4.8 g of a 60% dispersion of sodium hydride in mineral oil was suspended in 150 ml of N,N-dimethylformamide; while this suspension was stirred under ice cooling conditions, 11.4 g of methyl 6-chloro-7-methylimidazo[1,2-b]pyridazin-2-acetate was added little by little; followed by stirring at room temperature for 30 minutes. Under ice cooling conditions, 7.5 ml of methyl iodide was added, followed by stirring at room temperature for 6 hours. Ice water was poured, followed by extraction with ethyl acetate; the extract was washed with saline and dried with magnesium sulfate. The dry product was concentrated under reduced pressure; the residue was subjected to silica gel column chromatography and eluted with hexane:ethyl acetate (1:1). The desired fraction was collected and concentrated to yield 9.17 g of the title compound.

Melting point: 109–110° C.
Elemental analysis (for $C_{12}H_{14}N_3O_2Cl$):
Calculated (%): C, 53.84; H, 5.27; N, 15.70
Found (%): C, 53.96; H, 5.19; N, 15.86

Reference Example 24

Production of isopropyl 1-(6-chloroimidazo[1,2-b]pyridazin-2-yl)cyclopentanecarboxylate Process A: Production of methyl 1-(6-chloroimidazo[1,2-b]pyridazin-2-yl)cyclopentanecarboxylate 5.48 g of methyl 6-chloroimidazo[1,2-b]pyridazin-2-acetate was dissolved in 42 ml of N,N-dimethylformamide; while this solution was stirred under ice cooling conditions, 1.07 g of a 60% dispersion of sodium hydride in mineral oil was added little by little; followed by stirring at room temperature for 1.5 hours. Under ice cooling conditions, 3.19 ml of 1,4-dibromobutane was added drop by drop, followed by stirring at room temperature for 18 hours. Ice water was poured, followed by extraction with ethyl acetate; the extract was washed with saturated saline and dried with magnesium sulfate. The dry product was concentrated under reduced pressure; the residue was subjected to silica gel column chromatography and eluted with ethyl acetate:hexane (1:3). The desired fraction was collected and concentrated under reduced pressure to yield 1.72 g of the title compound.

$^1$H-NMR (CDCl$_3$) δ ppm: 1.63–1.85 (4H, m), 2.10–2.38 (2H, m), 2.42–2.68 (2H, m), 3.69 (3H, s), 7.02 (1H, d, J=9.4 Hz), 7.84 (1H, s), 7.86 (1H, d, J=8.6 Hz).
Process B In 30 ml of 2-propanol, 0.81 ml of concentrated sulfuric acid was dissolved; 1.7 of methyl 1-(6-chloroimidazo[1,2-b]pyridazin-2-yl)cyclopentanecarboxylate was added, followed by thermal refluxing for 7.5 hours. After cooling, the mixture was concentrated under reduced pressure, neutralized by the addition of aqueous sodium bicarbonate and extracted with ethyl acetate. The extract was washed with saturated saline and dried with magnesium sulfate. The dry product was concentrated under reduced pressure; the crystal precipitated was collected by filtration, washed with n-hexane and dried to yield 1.30 g of the title compound. The filtrate was concentrated under reduced pressure; the residue was subjected to silica gel column chromatography and eluted with hexane:ethyl acetate (3:1). The desired fraction was collected, concentrated under reduced pressure and dried to yield 356 mg of the title compound.

$^1$H-NMR (CDCl$_3$) δ ppm: 1.18 (3H, s), 1.21 (3H, s), 1.68–1.85 (4H, m), 2.13–2.32 (2H, m), 2.45–2.60 (2H, m), 4.94–5.13 (1H, m), 7.02 (1H, d, J=9.6 Hz), 7.83 (1H, s), 7.86 (1H, d, J=9.4 Hz).

Reference Example 25

Production of isopropyl 1-(6-chloroimidazo[1,2-b]pyridazin-2-yl)cyclopropanecarboxylate Process A: Production of methyl 1-(6-chloroimidazo[1,2-b]pyridazin-2-yl)cyclopropanecarboxylate 5.93 g of methyl 6-chloroimidazo[1,2-b]pyridazin-2-acetate was dissolved in 45 ml of N,N-dimethylformamide; while this solution was stirred under ice cooling conditions, 2.31 g of a 60% dispersion of sodium hydride in mineral oil was added little by little; followed by stirring at room temperature for 40 minutes. Under ice cooling conditions, 2.49 ml of 1,2-dibromoethane was added drop by drop, followed by stirring at room temperature for 14 hours. Ice water was poured, followed by extraction with ethyl acetate; the extract was washed with saturated saline and dried with magnesium sulfate. The dry product was concentrated under reduced pressure; the residue was subjected to silica gel column chromatography and eluted with hexane:ethyl acetate (2:1). The desired fraction was collected and concentrated under reduced pressure to yield 3.67 g of the title compound.

$^1$H-NMR (CDCl$_3$) δ ppm: 1.60–1.68 (2H, m), 1.70–1.85 (2H, m), 3.75 (3H, s), 7.00 (1H, d, J=9.6 Hz), 7.77 (1H, d, J=9.6 Hz), 8.28 (1H, s).
Process B In 70 ml of 2-propanol, 1.82 ml of concentrated sulfuric acid was dissolved; 3.44 g of methyl 1-(6-chloroimidazo[1,2-b]pyridazin-2-yl)cyclopropanecarboxylate was added, followed by thermal refluxing for 7.5 hours. After cooling, the mixture was concentrated under reduced pressure, neutralized by the addition of aqueous sodium bicarbonate and extracted with ethyl acetate. The extract was washed with saturated saline and dried with magnesium sulfate. The dry product was concentrated under reduced pressure; the crystal precipitated was collected by filtration, washed with ether and hexane and dried to yield 1.98 g of the title compound. The filtrate was concentrated under reduced pressure; the residue was subjected to silica gel column chromatography and eluted with hexane:ethyl acetate (5:1). The desired fraction was collected, concentrated under reduced pressure and dried to yield 650 mg of the title compound.

Melting point: 112–114° C.
Elemental analysis (for $C_{13}H_{14}N_3O_2Cl$):
Calculated (%): C, 55.82; H, 5.04; N, 15.02
Found (%): C, 55.75; H, 5.17; N, 14.99

Reference Example 26

Production of ethyl 2-(6-chloro-3-methylimidazo[1,2-b]pyridazin-2-yl)-2-methylpropionate Process A: Production of ethyl 6-chloro-3-methylimidazo[1,2-b]pyridazin-2-acetate 2.44 g of 3-amino-6-chloropyridazine was suspended in 37 ml of ethanol; 8.40 g of ethyl 4-bromo-3-oxopentanoate was added, followed by thermal refluxing for 18 hours. After cooling, the mixture was concentrated under reduced pressure; the residue was ajusted to pH 7 by the addition of aqueous sodium bicarbonate; ethyl ether was added; the precipitated was collected by filtration and extracted with ethyl ether; the extract was washed with saturated saline and dried with magnesium sulfate. The dry product was concentrated under reduced pressure; the residue was subjected to silica gel column chromatography and eluted with hexane:ethyl acetate (1:1). The desired fraction was collected to yield 2.63 g of the title compound.

$^1$H-NMR (CDCl$_3$) δ ppm: 1.27 (3H, t, J=7.1 Hz), 2.54 (3H, s), 3.85 (2H, s), 4.19 (2H, q, J=7.1 Hz), 6.99 (1H, d, J=9.6 Hz), 7.82 (1H, d, J=9.6 Hz).
Process B 5.41 g of ethyl 6-chloro-3-methylimidazo[1,2-b]pyridazin-2-acetate was dissolved in 40 ml of N,N-dimethylformamide; while this solution was stirred under ice cooling conditions, 1.87 g of a 60% dispersion of sodium hydride in mineral oil was added little by little; followed by stirring at room temperature for 40 minutes. Under ice cooling conditions, 3.32 ml of methyl iodide was added, followed by stirring at room temperature for 15 hours. Ice water was poured, followed by extraction with ethyl acetate; the extract was washed with saturated saline and dried with magnesium sulfate. The dry product was concentrated under reduced pressure; the residue was subjected to silica gel column chromatography and eluted with hexane:ethyl acetate (3:1). The desired fraction was collected and concentrated under reduced pressure to yield 2.69 g of the title compound.

$^1$H-NMR (CDCl$_3$) δ ppm: 1.21 (3H, t, J=7.2 Hz), 1.69 (6H, s), 2.48 (3H, s), 4.47 (2H, q, J=7.2 Hz), 7.21 (1H, d, J=9.6 Hz), 7.88 (1H, d, J=9.6 Hz).

Reference Example 27

Production of ethyl 6-chloro-2-methylimidazo[1,2-b]pyridazine-3-carboxylate 12.9 g of 3-amino-6-chloropyridazine was suspended in 250 ml of ethanol; 18.1 g of ethyl 2-chloro-3-oxobutanoate was added, followed by thermal refluxing for 6 hours. After cooling, the mixture was concentrated under reduced pressure; the residue was ajusted to pH 7 by the addition of aqueous sodium bicarbonate; ethyl ether was added; the precipitated was collected by filtration and extracted with ethyl ether; the extract was washed with saturated saline and dried with magnesium sulfate. The dry product was concentrated under reduced pressure; ethanol-1 N aqueous solution of sodium hydroxide (1:1) was added; the crystal precipitated was collected by filtration; the filtrate was concentrated again. The residue was crystallized by the addition of ethyl acetate and collected by filtration to yield 3.09 g of the title compound.

$^1$H-NMR (CDCl$_3$) δ ppm: 1.45 (3H, t, J=7.2 Hz), 2.74 (3H, s), 4.18 (2H, q, J=7.2 Hz), 6.97 (1H, d, J=9.4 Hz), 7.85 (1H, d, J=9.6 Hz).

Reference Example 28

Production of N-(6-chloro[1,2,4]triazolo[1,5-b]pyridazine-2-carbonyl)glycine ethyl ester 2.86 g of 6-chloro[1,2,4]triazolo[1,5-b]pyridazine-2-carboxylic acid and 2.72 ml of N-ethyldiisopropylamine were suspended in 30 ml of N,N-dimethylformamide; 2.63 g of N,N'-carbonyldiimidazole was added, followed by stirring at room temperature for 1 hour. To the reaction mixture, 2.21 g of glycine ethyl ester hydrochloride was added, followed by stirring at room temperature for 5 hours. Water was added; the crystal precipitated was collected by filtration, washed with water and ether and dried to yield 2.93 g of the title compound.

Melting point: 175–177° C.
Elemental analysis (for C$_{10}$H$_{10}$N$_5$O$_3$Cl):
Calculated (%): C, 42.34; H, 3.55; N, 24.69
Found (%): C, 42.40; H, 3.56; N, 24.76

Reference Example 29

Production of ethyl 2-(6-chloroimidazo[1,2,b]pyridazin-2-yl)-2-ethylbutanoate

Process A: Production of ethyl 4-bromo-2,2-diethyl-3-oxobutanoate 11.5 g of ethyl 2,2-diethyl-3-oxobutanoate was dissolved in acetic acid; 1 ml of a 25% solution of hydrobromic acid in 50 ml of acetic acid was added; a solution of 3.50 ml of bromine in 10 ml of acetic acid was added drop by drop in a water bath. After stirring at room temperature for 3 hours, the mixture was concentrated under reduced pressure; the residue was dissolved in hexane, washed with water, saturated aqueous sodium bicarbonate and saturated saline, and dried with magnesium sulfate. The dry product was concentrated under reduced pressure to yield 16.4 g of the title compound.

$^1$H-NMR (CDCl$_3$) δ ppm: 0.65–0.90 (6H, m), 1.28 (3H, t, J=7.2 Hz), 1.80–2.15 (4H, m), 4.09 (2H, s), 4.22 (2H, q, J=7.2 Hz).

Process B 13.2 g of ethyl 4-bromo-2,2-diethyl-3-oxobutanoate, 5.89 g of 3-amino-6-chloropyridazine and 5.76 g of sodium bicarbonate were suspended in 33 ml of ethanol, followed by thermal refluxing for 1 day. After cooling, water was added, followed by extraction with diisopropyl ether; the extract was washed with saturated saline and dried with magnesium sulfate. The dry product was concentrated under reduced pressure; the residue was subjected to silica gel column chromatography and eluted with hexane:ethyl acetate (4:1). The desired fraction was collected and concentrated under reduced pressure to yield 5.20 g of the title compound.

Melting point: 68–70° C.
Elemental analysis (for C$_{14}$H$_{18}$N$_3$O$_2$Cl):
Calculated (%): C, 55.85; H, 6.13; N, 14.21
Found (%): C, 55.86; H, 6.07; N, 13.99

Reference Example 30

Production of 4-(diphenylmethylamino)-1-piperidinepropanamine

Process A: Production of N-[3-[4-(diphenylaminomethyl)piperidino]propyl]phthalimide 7.38 g of N-(3-bromopropyl)phthalimide and 7.07 g of 4-(diphenylmethylamino)piperidine were dissolved in 80 ml of N,N-dimethylformamide; 4.04 g of potassium carbonate was added, followed by stirring at room temperature for 17 hours. Ice water was added to the reaction mixture, followed by extraction with ethyl acetate; the extract was washed with saline and dried with magnesium sulfate. The dry product was concentrated under reduced pressure; the residue was subjected to silica gel column chromatography and eluted with hexane:ethyl acetate:triethylamine (50:50:2). The desired fraction was collected and concentrated under reduced pressure to yield 9.65 g of the title compound as an oily substance.

$^1$H-NMR (CDCl$_3$) δ ppm: 1.08–1.30 (2H, m), 1.42–1.64 (2H, m), 1.74–1.92 (4H, m), 2.25–2.42 (1H, m), 2.34 (2H, t, J=7.2 Hz), 2.65–2.83 (2H, m), 3.73 (2H, t, J=6.9 Hz), 4.96 (1H, s), 7.12–7.40 (10H, m), 7.65–7.73 (2H, m), 7.78–7.88 (2H, m).

Process B 9.65 g of N-[3-[4-(diphenylaminomethyl)piperidino]propyl]phthalimide was dissolved in 40 ml of ethanol; 1.08 ml of hydrazine monohydrate was added, followed by thermal refluxing for 3.5 hours. After cooling, diisopropyl ether was added to the reaction mixture; the crystal precipitated was collected, washed with diisopropyl ether, dissolved in 45 ml of a 1 N aqueous solution of sodium hydroxide, 20 ml of tetrahydrofuran and 20 ml of water, and extracted with ethyl acetate. The extract was washed with water and saturated saline and dried with sodium sulfate. The dry product was concentrated under reduced pressure to yield 4.02 g of the title compound.

$^1$H-NMR (CDCl$_3$) δ ppm: 1.23–1.67 (4H, m), 1.82–1.98 (4H, m), 2.29–2.36 (2H, m), 2.32–2.52 (1H, m), 3.73 (2H, t, J=7.4 Hz), 2.71 (2H, d, J=6.8 Hz), 2.73–2.9 (2H, brm), 5.02 (1H, s), 7.10–7.57 (10H, m).

Reference Example 31

Production of N-(3,6-dichloroimidazo[1,2-b]pyridazine-2-carbonyl)glycine ethyl ester 0.86 g of N-(6-chloroimidazo[1,2-b]pyridazine-2-carbonyl)glycine ethyl ester was suspended in 30 ml of ethyl acetate; 1.2 g of N-chlorosuccinimide was added, followed by thermal refluxing for 20 hours. After cooling, 30 ml of tetrahydrofuran was added; the mixture was washed with an aqueous solution of sodium thiosulfate and saline and dried with magnesium sulfate. The dry product was concentrated under reduced pressure; ethyl ether was added to the residue; the crystal precipitated was collected by filtration, washed with ethyl ether and dried to yield 0.552 g of the title compound.

$^1$H-NMR (CDCl$_3$) δ ppm: 1.32 (3H, t, J=7.2 Hz), 4.27 (2H, d, J=5.6 Hz), 4.27 (2H, q, J=7.2 Hz), 7.21, 7.91 (each 1H, d, J=9.6 Hz), 7.82 (1H, t, J=5.6 Hz).

Reference Example 32

Production of N-(6-chloroimidazo[1,2-b]pyridazine-2-carbonyl)β-alanine ethyl ester 1.98 g of 6-chloroimidazo[1,2-b]pyridazine-2-carboxylic acid was suspended in 25 ml of N,N-dimethylformamide; 1.78 g of N,N'-dicarbonylimidazole was added, followed by stirring at room temperature for 1 hour. To this mixture, 1.69 g of β-alanine ethyl ester hydrochloride and 1.53 ml of triethylamine were added, followed by further stirring for 3 hours. Ice water was added to the reaction mixture; the crystal precipitated was collected by filtration, washed with water and dried to yield 2.57 g of the title compound.

Melting point: 132–134° C.
Elemental analysis (for C$_{12}$H$_{13}$N$_4$O$_3$Cl):
Calculated (%): C, 48.58; H, 4.42; N, 18.88
Found (%): C, 48.43; H, 4.33; N, 18.68

Reference Example 33

Production of ethyl 6-chloro-3-methylimidazo[1,2-b]pyridazine-2-carboxylate 5.83 g of 3-amino-6-chloropyridazine was suspended in 70 ml of ethanol; 9.75 g of methyl 3-bromo-2-oxobutyrate and 8.6 ml of N-ethyldiisopropylamine were added, followed by thermal refluxing for 5 hours. After cooling, the mixture was concentrated under reduced pressure; the residue was ajusted to pH 7 by the addition of an aqueous solution of sodium hydrogen carbonate and extracted with ethyl acetate-tetrahydrofuran (1:1); the extract was washed with saline and dried with magnesium sulfate. The dry product was concentrated under reduced pressure; ethyl acetate was added to the residue; the crystal precipitated was collected by filtration, washed with ethyl acetate and dried to yield 3.9 g of the title compound.

Melting point: 170–171° C.
Elemental analysis (for C$_{10}$H$_{10}$N$_3$O$_2$Cl):
Calculated (%): C, 50.12; H, 4.21; N, 17.53
Found (%): C, 50.28; H, 4.18; N, 17.23

Reference Example 34

Production of N-(6-chloro-3-methylimidazo[1,2-b]pyridazine-2-carbonyl)glycine ethyl ester 3.9 g of ethyl 6-chloro-3-methylimidazo[1,2-b]pyridazine-2-carboxylate was suspended in 40 ml of tetrahydrofuran; 30 ml of a 1 N aqueous solution of sodium hydroxide was added, followed by stirring at room temperature for 3 hours. The mixture was concentrated under reduced pressure; the residue was ajusted to pH 4 by the addition of 50 ml of water and 1 N hydrochloric acid; the crystal precipitated was collected by filtration and dried to yield 2.55 g of 6-chloro-3-methylimidazo[1,2-b]pyridazine-2-carboxylic acid. 1.27 g of this carboxylic acid was dissolved in 20 ml of N,N-dimethylformamide; 1.07 g of N,N'-carbonyldiimidazole was added, followed by stirring at room temperature for 30 minutes. To this mixture, 0.922 g of glycine ethyl ester hydrochloride and 0.915 ml of triethylamine were added, followed by further stirring for 3 hours. 60 ml of ice water was added to the reaction mixture; the crystal precipitated was collected by filtration, washed with water and dried to yield 1.18 g of the title compound.

Melting point: 192–195° C.
Elemental analysis (for C$_{12}$H$_{13}$N$_4$O$_3$Cl):
Calculated (%): C, 48.58; H, 4.42; N, 18.88
Found (%): C, 48.65; H, 4.13; N, 18.93

Reference Example 35

Production of 6-chloro-2-isopropylimidazo[1,2-b]pyridazine

To a solution of 3-methyl-2-butanone (5.17 g) in methanol (60 ml), bromine (3.1 ml) was added under ice cooling conditions, followed by stirring for 45 minutes. To this mixture, water (30 ml) was added, followed by stirring at room temperature for 30 minutes. To this mixture, water and hexane were added; the organic layer was separated; the water layer was extracted with hexane. The organic layers combined were washed with water and a saturated aqueous solution of sodium hydrogen carbonate, dried over magnesium sulfate, filtered and concentrated under reduced pressure. The residue was dissolved in ethanol (20 ml); 3-amino-6-chloropyridazine (5.18 g) and sodium hydrogen carbonate (6.30 g) were added, followed by thermal refluxing for 3 hours. Water and ethyl acetate were added to the reaction mixture; the insoluble substances were filtered off; the organic layer was separated; the water layer was extracted with ethyl acetate. The organic layers combined were washed with water, treated with activated charcoal, filtered and concentrated under reduced pressure. The residue was dissolved in ethyl acetate; the insoluble substances were filtered and concentrated under reduced pressure. The residue was subjected to silica gel column chromatography (hexane:ethyl acetate 3:1) and recrystallized from hexane to yield the title compound (1.37 g).

Melting point: 106–108° C.
Elemental analysis (for C$_9$H$_{10}$N$_3$Cl):
Calculated (%): C, 55.25; H, 5.15; N, 21.48; Cl, 18.12
Found (%): C, 55.35; H, 5.10; N, 21.50; Cl, 18.03

Reference Example 36

Production of isopropyl 6-chloro[1,2,4]triazolo[1,5-b]pyridazine-2-carboxylate 2.14 g of 6-chloro[1,2,4]triazolo[1,5-b]pyridazine-2-carboxylic acid and 5.57 ml of N-ethyldiisopropylamine were dissolved in 30 ml of N,N-dimethylformamide; 3.23 ml of isopropyl iodide was added, followed by stirring at room temperature for 10 hours and at 50° C. for 3 hours. After cooling, water was added, followed by extraction with ethyl acetate; the extract was washed with saturated saline and dried with magnesium sulfate. The dry product was concentrated under reduced pressure; the residue was subjected to silica gel column chromatography and eluted with ethyl acetate. The desired fraction was collected and concentrated under reduced pressure to yield 2.21 g of the title compound.

$^1$H-NMR (CDCl$_3$) δ ppm: 1.46 (3H, s), 1.49 (3H, s), 5.33–5.53 (1H, m), 7.52 (1H, d, J=9.6 Hz), 8.19 (1H, d, J=9.6 Hz).

Reference Example 37

Production of N-(6-chloro[1,2,4]triazolo[1,5-b] pyridazine-2-carbonyl)-2,2-dimethylglycine ethyl ester 1.52 g of 6-chloro[1,2,4]triazolo[1,5-b]pyridazine-2-carboxylic acid and 1.45 ml of N-ethyldiisopropylamine were suspended in 15 ml of N,N-dimethylformamide; 1.37 g of N,N'-carbonyldiimidazole was added, followed by stirring at room temperature for 3 hours. To the reaction mixture, 1.41 g of 2-aminoisobutyric acid ethyl ester hydrochloride was added, followed by stirring at room temperature for 4 hour. Water was added, followed by extraction with ethyl acetate-tetrahydrofuran (1:1); the extract was washed with saturated saline and dried with magnesium sulfate. The dry product was concentrated under reduced pressure; the crystal precipitated was washed with ethyl ether, collected by filtration and dried to yield 1.48 g of the title compound. The filtrate was concentrated under reduced pressure; the residue was subjected to silica gel column chromatography and eluted with ethyl acetate. The desired fraction was collected and concentrated under reduced pressure to yield 450 mg of the title compound.

$^1$H-NMR (CDCl$_3$) δ ppm: 1.29 (3H, t, J=7.1 Hz), 1.73 (6H, s), 4.26 (2H, q, J=7.2 Hz), 7.52 (1H, d, J=9.4 Hz), 7.94 (1H, brs), 8.16 (1H, d, J=9.4 Hz).

Reference Example 38

Production of isopropyl 2-(6-chloroimidazo[1,2-b] pyridazin-2-yl)-2-methylpropionate In 18 ml of isopropanol, 995 mg of concentrated sulfuric acid was dissolved; 1.0 of methyl 2-(6-chloroimidazo[1,2-b]pyridazin-2-yl)-2-methylpropionate was added, followed by thermal refluxing for 40 hours. After cooling, the mixture was concentrated under reduced pressure, neutralized by the addition of aqueous sodium bicarbonate and extracted with ethyl acetate. The extract was washed with saturated saline and dried with magnesium sulfate. The dry product was concentrated under reduced pressure; the crystal precipitated was collected, washed with hexane and dried to yield 794 mg of the title compound. The filtrate was concentrated under reduced pressure; the residue was subjected to silica gel column chromatography and eluted with hexane:ethyl acetate (5:1). The desired fraction was collected and dried to yield 215 mg of the title compound.

Melting point: 100–101° C.

Elemental analysis (for $C_{13}H_{16}N_3O_2Cl$):

Calculated (%): C, 55.42; H, 5.72; N, 14.91

Found (%): C, 55.46; H, 5.53; N, 14.94

Experimental Example 1

Effect on histamine-induced skin reactions in guinea pigs

Male Hartley guinea pigs weighing about 500 g were used. After the dorsal hair was shaved under ether anesthesia, 1 ml of a 2.5% pontamine sky blue solution was injected intravenously administered, and then 0.1 ml of histamine at 3 μg/ml was injected intradermally into 2 sites (left and right) in the back. Thirty minutes after the injection of histamine, animals were killed by bleeding and the skin was removed. Two perpendicular diameters (mm) of each blue spot on the inside of the skin were measured and multiplied; the mean for the two products was taken as the microvascular permeability index. Test compounds were suspended in a 5% gum arabic solution and orally administered in a volume of 0.2 ml/100 g body weight 1 hour before histamine administration. Animals in the control group received the same volume of a 5% gum arabic solution. The suppression rate of the sample for the title reaction was calculated using Equation 1.

Inhibition (%) of histamine-induced skin reactions=100×(1−vascular permeability index in the presence of drug/vascular permeability index in control group)  Equation 1

The results are given in Table 1.

TABLE 1

Effects on Histamine-induced Skin Reactions

| Compound | Inhibition (%) of Histamine-induced Skin Reactions, 3 mg/kg Oral Administration |
|---|---|
| Example 6 | 91 |
| Example 12 | 91 |
| Example 18 | 91 |
| Example 20 | 92 |
| Example 21 | 91 |
| Example 37 | 92 |
| Example 41 | 92 |
| Example 45 | 91 |

Experimental Example 2

1) Preparation of Guinea Pig Eosinophils

To male Hartley guinea pigs, 2 ml of equine serum (Bio-Whittaker, Inc.) was intraperitoneally administered once weekly for 8 consecutive weeks. At 48 hours after final administration, 75 ml of physiological saline was intraperitoneally injected, after which the saline was recovered and centrifuged at 400×g for 5 minutes. The resulting sediment was suspended in 5 ml of Percoll solution (density (d)=1.07) and layered on top of the multiple layers of different densities of Percoll solution (density(d)=1.112, 5 ml; d=1.095, 10 ml; d=1.090, 10 ml; d=1.085, 5 ml), followed by centrifugation at 1,000×g for 25 minutes (20° C.). The cell layer formed at the interface between densities 1.112 and 1.095 was collected. Erythrocytes present in the collected cell sediment were removed by hypotonic treatment (suspended in water for 30 seconds).

The cell sediment was washed 3 times with Hanks' solution containing 10 mM Hepes (Dojin Kagaku) (Hanks-Hepes) and suspended in a Hanks-Hepes solution containing 2% human serum albumin (Wako Pure Chemical Industry or Sigma) (Hanks-Hepes-HSA) to a final concentration of 5.56×10$^6$ cells/ml. Eosinophil purity was 90%, viability being over 98%.

2) Determination of Chemotactic Reaction Suppression

To a 24-well petri dish, which serves as a lower chamber, 600 μl of Hanks-Hepes-HSA solution containing LTB$_4$ (final concentration $10^{-8}$ M, Cascade Biochemical Ltd.), was transferred, followed by incubation at 37° C. for 30 minutes in a carbon dioxide incubator. Separately, 200 μl of eosinophil suspension ($5\times10^6$ cells/ml), previously incubated at 37° C. for 15 minutes, was added to Chemotaxicell (polycarbonate membrane, pore size 3 μm, thickness 10 μm), which serves as an upper chamber, after the upper chamber was attached to the 24-well petri dish. After 2 hours of reaction in the $CO_2$ incubator, the Chemotaxicell was removed; 60 μl of a 2% (w/v) solution of EDTA in physiological saline was added to the liquid in the lower chamber. After the mixture was on cooled ice, the cells migrating into the lower chamber were counted using a blood cell counter [Coulter Counter (trade name)]. The test drug, dissolved in N,N-dimethyl formamide (DMF), was added to both the upper and lower chambers to a final concentration of $10^{-5}$ M.

Chemotactic reaction suppression rate=[1−(number of migrating cells in the presence of drug/number of migrating cells in the absence of drug)]×100  Equation 2 suppression rates of $LTB_4$-induced chemotactic reaction by test substances ($1\times10^{-5}$ M) were calculated using the above equation. The results are shown in Table 2.

TABLE 2

Action on $LTB_4$-induced Chemotactic Reaction in Guinea Pig Eosinophils

| Compound | Suppression Rate (%) |
|---|---|
| Example 2 | 54 |
| Example 6 | 64 |
| Example 20 | 61 |
| Example 34 | 50 |
| Example 35 | 52 |
| Example 36 | 64 |
| Example 47 | 54 |
| Example 51 | 80 |
| Example 59 | 54 |
| Example 61 | 50 |
| Example 62 | 52 |

Preparation Example 1

| (1) Compound of Example 6 | 10.0 mg |
|---|---|
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 6, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

Preparation Example 2

| (1) Compound of Example 6 | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 6 and 3.0 mg of magnesium stearate were mixed and granulated, using 0.07 ml of an aqueous solution of soluble starch (containing 7.0 mg of soluble starch). The resulting granules were dried and mixed with 70.0 mg of lactose and 50.0 mg of corn starch, followed by compression, to yield tablets.

Preparation Example 3

| (1) Compound of Example 6 | 5.0 mg |
|---|---|
| (2) Sodium chloride | 20.0 mg |
| (3) Distilled water was added to reach a total quantity of 2 ml. | |

5.0 mg of the compound obtained in Example 6 and 20.0 mg of sodium chloride were dissolved in distilled water, and diluted with water to reach a total quantity of 2.0 ml. The resulting solution was filtered and aseptically packed in a 2 ml ampule, which was sterilized and sealed to yield a solution for injection.

INDUSTRIAL APPLICABILITY

Exhibiting excellent anti-allergic activity, anti-histaminic activity, anti-inflammatory activity, eosinophil chemotaxis-inhibiting activity and other activities, the compound (I) of the present invention or a salt thereof is useful as an agent for treating or preventing asthma, allergic rhinitis, atopic dermatitis, allergic conjunctivitis, chronic urticaria etc.

What is claimed is:

1. A compound represented by the formula:

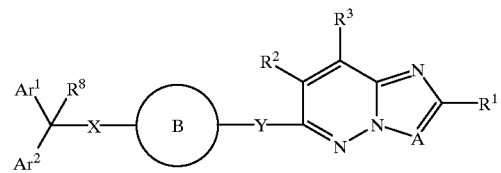

wherein $Ar^1$ and $Ar^2$ are independently (i) a $C_{6-14}$ single cyclic or condensed cyclic aromatic hydrocarbon group which may be substituted, (ii) a 5 to 8 membered single cyclic group containing 1 to 4 hetero atoms selected from a nitrogen atom, a sulfur atom and an oxygen atom other than carbon atoms, which may be substituted, or (iii) a condensed cyclic group formed by a 5 to 8 membered single cyclic group of (ii) and a $C_{6-14}$ single cyclic or condensed cyclic aromatic hydrocarbon group of (i), with a hydrogen atom removed, which may be substituted, and $Ar^1$ and $Ar^2$ may form a condensed cyclic group with an adjacent carbon atom;

ring B is a 3 to 13 membered nitrogen-containing heterocycle containing at least one nitrogen atom which may contain 1 to 3 hetero atoms selected from a nitrogen atom, an oxygen atom and a sulfur atom, which may be substituted;

X and Y are the same or different and are independently a bond, an oxygen atom, S(O)p where p is an integer of 0 to 2, $NR^4$ wherein $R^4$ is a hydrogen atom or a lower alkyl group, or a bivalent linear lower hydrocarbon group which may contain 1 to 3 hetero atoms and the bivalent linear lower hydrogen group may be substituted;

A is a nitrogen atom or $CR^7$ wherein $R^7$ is a hydrogen atom, a halogen atom, a hydrocarbon which may be substituted, an acyl group represented by the formula: —(C=O)—$R^9$, —SO—$R^9$, 13 $SO_2$—$R^9$, —(C=O)$NR^{10}R^9$, —(C=O)O—$R^9$, —(C=S)O—$R^9$ or —(C=S)$NR^{10}R^9$ is a hydrogen atom, a hydrocarbon group which may be substituted or a hydroxy group which may be substituted by a hydrocarbon group which may be substituted and $R^{10}$ is a hydrogen atom or a lower alkyl group, or a hydroxy group which may be substituted;

$R^1$, $R^2$ and $R^3$, are the same or different and are independently a hydrogen atom, a halogen atom, a hydrocarbon group which may be substituted, an acyl group represented by the formula: —(C=O)—$R^9$, —SO—$R^9$, —$SO_2$—$R^9$, —(C=O)$NR^9R^{10}$, —C(C=O)O—$R^9$, —(C=S)O—$R^9$, —(C=S)$NR^9R^{10}$ or a hydroxy group which may be substituted;

$R^8$ is a hydrogen atom, a hydroxy group which may be substituted by lower alkyl or a carbonyl group, or a salt thereof, provided that ring B is not

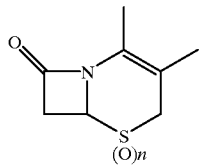

wherein n is 0 or 1.

2. A compound represented by the formula:

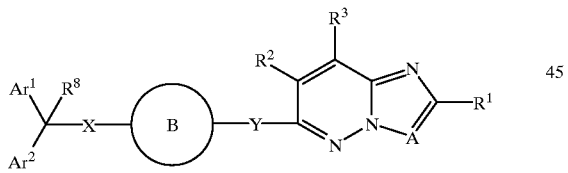

wherein $Ar^1$ and $Ar^2$ are independently (i) a $C_{6-14}$ single cyclic or condensed cyclic aromatic hydrocarbon group which may be substituted, (ii) a 5 to 8 membered single cyclic group containing 1 to 4 hetero atoms selected from a nitrogen atom, a sulfur atom and an oxygen atom other than carbon atoms, which may be substituted, or (iii) a condensed cyclic group formed by a 5 to 8 membered single cyclic group of (ii) and a $C_{6-14}$ single cyclic or condensed cyclic aromatic hydrocarbon group of (i), and the $C_{6-14}$ single cyclic or condensed cyclic aromatic hydrocarbon group, the 5 to 8 membered single cyclic group and the group formed by the 5 to 8 membered aromatic heterocyclic group and the $C_{6-14}$ aromatic hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo; and $Ar^1$, $Ar^2$ and the adjacent carbon atom may form a condensed cyclic group represented by the formula:

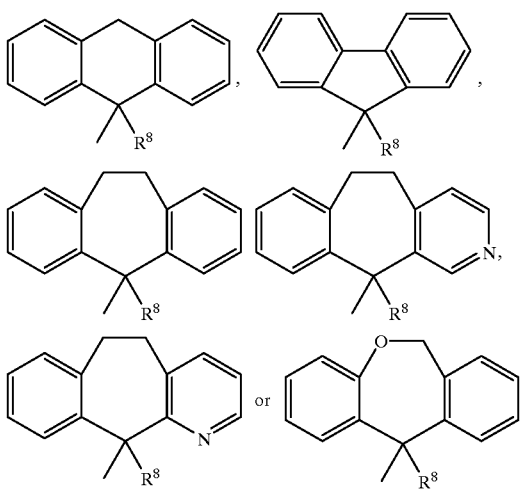

wherein $R^8$ is a hydrogen atom, a hydroxy group which may be substituted by $C_{1-6}$ alkyl or a carboxyl group, and the condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) C6–10 aryl, (xxvi) $C_{6-10}$ aryloxy, (xxvii) $C_{7-16}$ aralkyl-oxy and (xxviii) oxo;

the ring B is a 3 to 9 membered nitrogen-containing heterocycle containing at least one nitrogen atom which may contain 1 to 3 hetero atoms selected by a nitrogen atom, an oxygen atom and a sulfur atom, and the 3 to 9 membered nitrogen-containing heterocycle may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo;

X and Y are same or different (a) a bond, (b) an oxygen atom, (c) S(O)p wherein p is an integer of 0 to 2, (d) $NR^4$ wherein $R^4$ is a hydrogen atom or a linear or branched $C_{1-6}$ alkyl group or (e) a bivalent linear $C_{1-6}$ hydrocarbon group which may contain 1 to 3 hetero atoms selected by an oxygen atom and a sulfur atom, and the bivalent linear $C_{1-6}$ hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo;

A is a nitrogen atom or $CR^7$ wherein $R^7$ is
  (a) a hydrogen atom,
  (b) a halogen atom,
  (c) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo,
  (d) an acyl group represented by the formula: —(C=O)—$R^9$, —$SO_2$—$R^9$, —SO—$R^9$, —(C=O)$NR^{10}R^9$, —(C=O)O—$R^9$, —(C=S)O—$R^9$ or —(C=S)$NR^{10}R^9$ wherein $R^9$ is (a') a hydrogen atom, (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo, $R^{10}$ is a hydrogen atom or a $C_{1-6}$ alkyl group, or
  (e) a group represented by the formula: —$OR^{12}$ wherein $R^{12}$ is (a') a hydrogen atom or (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo;

$R^1$, $R^2$ and $R^3$ are the same or different and are independently (a) a hydrogen atom, (b) a halogen atom, (c) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo, (d) an acyl group represented by the formula: —(C=O)—$R^{13}$, —$SO_2$—$R^{13}$, —SO—$R^{13}$, —(C=O)$NR^{14}R^{13}$, —(C=O)O—$R^{13}$, —(C=S)O—$R^{13}$ or —(C=S)$NR^{14}R^{13}$ wherein $R^{13}$ is (a') a hydrogen atom, (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo or (c') a group represented by the formula: —$OR^{15}$ wherein $R^{15}$ is (a") a hydrogen atom or (b") a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo, $R^{14}$ is a hydrogen atom or a $C_{1-6}$ alkyl group; or (e) a group represented by the formula: —$OR^{16}$ wherein $R^{16}$ is (a') a hydrogen atom or (b') a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenredioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy which may be substituted by 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) mono-$C_{1-6}$ alkyl-carbamoyl, (xxi) di-$C_{1-6}$ alkyl-carbamoyl, (xxii) $C_{6-10}$ aryl-carbamoyl, (xxiii) sulfo, (xxiv) $C_{1-6}$ alkyl sulfonyl, (xxv) $C_{6-10}$ aryl, (xxvi) $C_{6-10}$ aryloxy, (xxvii) $C_{7-16}$ aralkyl-oxy and (xxviii) oxo;

$R^8$ is a hydrogen atom, a hydroxy group which may be substituted by $C_{1-6}$ alkyl or a carboxyl group, or a salt thereof, provided that the ring B is not

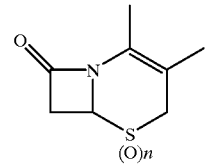

wherein n is 0 or 1.

3. The compound as claimed in claim 1 or 2 wherein $Ar^1$ and $Ar^2$ are independently a $C_{6-14}$ single cyclic or condensed cyclic aromatic hydrocarbon group which may be substituted.

4. The compound as claimed in claim 1 or 2 wherein $Ar^1$ and $Ar^2$ are independently a phenyl group which may be substituted.

5. The compound as claimed in claim 1 or 2 wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms.

6. The compound as claimed in claim 1 or 2 wherein the ring B is a ring represented by the formula:

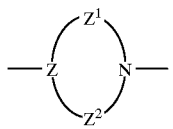

wherein Z is a nitrogen atom or a methyne group; $Z^1$ and $Z^2$ are independently a linear $C_{1-4}$ alkylene group which may be substituted by hydroxy, oxo or $C_{1-6}$ alkyl.

7. The compound as claimed in claim 6 wherein $Z^1$ and $Z^2$ are independently a linear $C_{1-2}$ alkylene group.

8. The compound as claimed in claim 1 or 2 wherein X is a bond, an oxygen atom or NH.

9. The compound as claimed in claim 1 or 2 wherein X is a bond or an oxygen atom.

10. The compound as claimed in claim 1 or 2 wherein Y is a group represented by the formula:

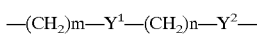

wherein $Y^1$ and $Y^2$ are the same or different and are independently a bond, an oxygen atom, S(O)p wherein p is an integer of 0 to 2, $NR^4$ wherein $R^4$ is a hydrogen atom or a lower alkyl group, a carbonyl group, a carbonyloxy group or a group represented by the formula:

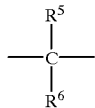

wherein $R^5$ and $R^6$ are the same or different and are independently a hydroxy group or a $C_{1-4}$ alkyl group; m and n are an integer of 0 to 4, and sum of m and n is not more than 6.

11. The compound as claimed in claim 1 or 2 wherein Y is (i) a $CH_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3.

12. The compound as claimed in claim 1 or 2 wherein $R^1$, $R^2$, $R^3$ and $R^7$ are the same or different and are independently (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group or (v) a carboxyl group.

13. The compound as claimed in claim 1 or 2 wherein $R^1$ is (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) a $C_{3-6}$ cycloalkyl group which may be substituted by $C_{1-6}$ alkoxy-carbonyl.

14. The compound as claimed in claim 1 or 2 wherein $R^2$ is a hydrogen atom, a $C_{1-6}$ alkyl group, a $C_{1-6}$ alkoxy-carbonyl group or a carboxyl group.

15. The compound as claimed in claim 1 or 2 wherein $R^3$ is a hydrogen atom.

16. The compound as claimed in claim 1 or 2 wherein $R^7$ is a hydrogen atom, a halogen atom, a $C_{1-6}$ alkyl group, a $C_{1-6}$ alkoxy-carbonyl group or a carboxyl group.

17. The compound as claimed in claim 1 or 2 wherein $R^8$ is a hydrogen atom or a hydroxy group.

18. The compound as claimed in claim 1 or 2 wherein A is a nitrogen atom.

19. The compound as claimed in claim 1 or 2 wherein A is $CR^{7'}$ wherein $R^{7'}$ is a hydrogen atom, a halogen atom, a $C_{1-6}$ alkyl group, a $C_{1-6}$ alkoxy-carbonyl group or a carboxyl group.

20. The compound as claimed in claim 1 or 2 wherein A is CH.

21. The compound as claimed in claim 1 or 2 wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms; the ring B is a ring represented by the formula:

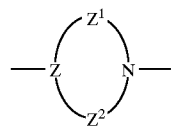

wherein Z is a nitrogen atom or a methyne group; $Z^1$ and $Z^2$ is independently a linear $C_{1-4}$ alkylene group which may be substituted by hydroxy, oxo or $C_{1-6}$ alkyl; X is a bond, an oxygen atom or NH; Y is (i) a $C_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^1$ is (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) a $C_{3-6}$ cycloalkyl group which may be substituted by $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group.

22. The compound as claimed in claim 1 or 2 wherein $Ar^1$ and $Ar^2$ are independently a phenyl group; the ring B is a ring represented by the formula:

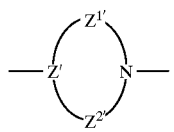

wherein $Z'$ is a methyne group; $Z^{1'}$ and $Z^{2'}$ are an ethylene group; X is an oxygen atom or NH; Y is —$(CH_2)_{p^1}$NH— wherein $p^1$ is an integer of 1 to 6; A is $CR^{7''}$ wherein $R^{7''}$ is a hydrogen atom or a $C_{1-6}$ alkyl group; $R^1$ is (i) a hydrogen atom, (ii) a $C_{1-6}$ alkyl group which may be substituted by carboxyl or $C_{1-6}$ alkoxy-carbonyl or (iii) a carbamoyl group which may be substituted by a $C_{1-6}$ alkyl group optionally having $C_{1-6}$ alkoxy-carbonyl; $R^2$ is a hydrogen atom; $R^3$ is a hydrogen atom; $R^8$ is a hydrogen atom.

23. Ethyl 2-[6-[3-[4-(diphenylmethoxy)piperidino]propyl-amino]imidazo[1,2-b]pyridazin-2-yl]-2-methylpropionate or a salt thereof.

24. 2-[6-[3-[4-(diphenylmethoxy)piperidino]propylamino]imidazo[1,2-b]pyridazin-2-yl]-2-methylpropionic acid or a salt thereof.

25. Ethyl N-[6-[3-[4-(diphenylmethoxy)piperidino]propyl-amino]imidazo[1,2-b]pyridazine-2-carbonyl]glycinate or a salt thereof.

26. Ethyl 2-[6-[3-[4-(diphenylmethoxy)piperidino]propyl-amino]-3-methylimidazo[1,2-b]pyridazin-2-yl]-2-methylpropionate or a salt thereof.

27. Ethyl 2-[6-[3-[4-(diphenylmethylamino)piperidino]propylamino]imidazo[1,2-b]pyridazin-2-yl]-2-methylpropionate or a salt thereof.

28. The compound as claimed in claim 1, wherein the ring B is a 3 to 6 nitrogen-containing heterocycle which may be substituted.

29. A pharmaceutical composition which comprises the compound as claimed in claim 1, or a salt thereof, and a pharmaceutically acceptable carrier.

30. A method for suppressing a histamine or an eosinophil chemotaxis comprising administering an effective amount of the compound as claimed in claim 1 or a salt thereof to mammals.

31. A method for treating asthma, allergic conjunctivitis, allergic rhinitis, chronic urticaria or atopic dermatitis comprising administering an effective amount of the compound as claimed in claim 1 or a salt thereof to mammals.

32. A method for producing a compound as claimed in claim 1 or 2, or a salt thereof, which comprises reacting a compound represented by the formula:

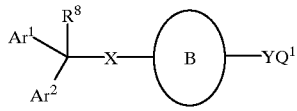

wherein $Q^1$ is a leaving group selected from a hydrogen atom or an alkali metal, and other symbols are the same as defined in claim 1 or 2, or a salt thereof with a compound represented by the formula:

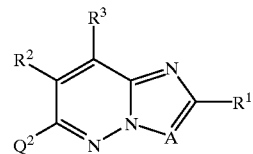

wherein $Q^2$ is a leaving group selected from a halogen atom, a $C_{6-10}$ arylsulfonyloxy group or a $C_{1-4}$ alkylsulfonyloxy group, and other symbols are the same as defined in claim 1 or 2, or a salt thereof.

33. A method of making a medicament comprising formulating the medicament with a pharmaceutically effective amount of the compound of claim 1.

* * * * *

UNITED STATES PATENT AND TRADEMARK OFFICE
CERTIFICATE OF CORRECTION

PATENT NO. : 6,248,740 B1
DATED : June 19, 2001
INVENTOR(S) : Yasuhiko Kawano, Hideaki Nagaya and Michiyo Gyoten It is certified that error appears in the above-identified patent and that said Letters Patent is hereby corrected as shown below:

Column 4,
Line 17, please insert
-- The present invention provides:
(1) A compound represented by the formula: --
Lines 27-28, please delete
"The present invention provides:
(1) A compound represented by the formula:"

Column 107,
Line 11, please delete "13"
Line 13, "-(C=S)NR$^{10}$R$^9$ is a hydrogen atom," should read instead -- -(C=S)NR$^{10}$R$^9$, wherein R$^9$ is a hydrogen atom,"

Column 108,
Line 54, "C6-10" should read instead -- C$_{6-10}$ --

Signed and Sealed this

Ninth Day of July, 2002

Attest:

JAMES E. ROGAN
Attesting Officer    Director of the United States Patent and Trademark Office